US008093389B2

(12) United States Patent  
Iino et al.

(10) Patent No.: US 8,093,389 B2  
(45) Date of Patent: Jan. 10, 2012

(54) SUBSTITUTED SPIROCHROMANONE DERIVATIVES

(75) Inventors: Tomoharu Iino, Tsukuba (JP); Hideki Jona, Moriya (JP); Jun Shibata, Tsukuba (JP); Tadashi Shimamura, Tsukuba (JP); Takeru Yamakawa, Tsukuba (JP); Lihu Yang, Edison, NJ (US)

(73) Assignees: Merck Sharp & Dohme Corp., Rahway, NJ (US); MSD K.K., Tokyo (JP)

( * ) Notice: Subject to any disclaimer, the term of this patent is extended or adjusted under 35 U.S.C. 154(b) by 1038 days.

(21) Appl. No.: 12/007,000

(22) Filed: Jan. 8, 2008

(65) Prior Publication Data

US 2008/0171761 A1    Jul. 17, 2008

Related U.S. Application Data

(60) Provisional application No. 60/880,302, filed on Jan. 12, 2007.

(51) Int. Cl.
  *C07D 413/06*   (2006.01)
  *C07D 405/04*   (2006.01)
  *A61K 31/438*   (2006.01)
(52) U.S. Cl. ......... 546/18; 514/278; 544/111; 544/126
(58) Field of Classification Search ............ 546/18; 514/278, 232.8; 544/111, 126
  See application file for complete search history.

(56) References Cited

U.S. PATENT DOCUMENTS

| 4,261,988 A | 4/1981 | Widdig et al. |
| 5,206,240 A | 4/1993 | Baldwin et al. |
| 5,633,247 A | 5/1997 | Baldwin et al. |
| 5,688,997 A | 11/1997 | Baldwin et al. |
| 5,885,999 A | 3/1999 | Elliott et al. |
| 2001/0039286 A1 | 11/2001 | Dinnell et al. |
| 2007/0021453 A1 | 1/2007 | Yamakawa et al. |

FOREIGN PATENT DOCUMENTS

| EP | 0 431 943 B1 | 12/1990 |
| EP | 0 518 805 A1 | 6/1992 |
| GB | 2 309 458 A | 1/1997 |
| JP | 2005119987 | 5/2005 |
| WO | WO 94/17045 | 8/1994 |
| WO | WO 95/30642 | 11/1995 |
| WO | WO 96/39140 | 12/1996 |
| WO | WO 97/16569 | 5/1997 |
| WO | WO 97/16729 | 5/1997 |
| WO | WO 02/20509 A2 | 3/2002 |
| WO | WO 02/20509 A3 | 3/2002 |
| WO | WO 2004/058727 A1 | 7/2004 |
| WO | WO 2004/092179 | 10/2004 |
| WO | WO2005/003128 A1 | 1/2005 |
| WO | WO 2006/040329 A1 | 4/2006 |
| WO | WO 2006/055752 A2 | 5/2006 |
| WO | WO 2006/055752 A3 | 5/2006 |
| WO | WO 2006/117669 A1 | 11/2006 |
| WO | WO 2007/011809 A1 | 1/2007 |
| WO | WO 2007/011811 A1 | 1/2007 |
| WO | WO 2008/065508 A1 | 6/2008 |

OTHER PUBLICATIONS

Database Chemcats Abstract—XP-002477903—Accession No. 2029653204—CAS Registry No. 887467-90-5, Publication Date Sep. 6, 2007.

(Continued)

*Primary Examiner* — Rita Desai  
(74) *Attorney, Agent, or Firm* — Janet E. Fair; John C. Todaro

(57) ABSTRACT

The invention relates to a compound of a general formula (I):

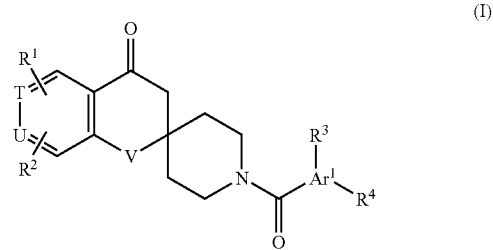

wherein $Ar^1$ represents a group formed from an aromatic ring selected from a group consisting of indole, 1H-indazole, 2H-indazole, 1H-thieno[2,3-c]pyrazole, 1H-pyrazolo[3,4-b]pyridine, benzo[b]furan, benzimidazole, benzoxazole, 1,2-benzisoxazole and imidazo[1,2-a]pyridine; $R^1$ and $R^2$ each represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of $-Q^1-N(R^a)-Q^2-R^b$; an optionally-substituted C1-C6 alkyl, aryl or heterocyclic group; or a C1-C6 alkyl or C2-C6 alkenyl group having the aryl or heterocyclic group; $R^3$ and $R^4$ each represent a hydrogen atom, a halogen atom, a nitro group, a cyclo-C3-C6 alkyl group, a carbamoyl group optionally substituted with a C1-C6 alkyl or cyclo-C3-C6 alkyl group, or a group of $-N(R^e)R^f$; an optionally-substituted C2-C7 alkanoyl, C1-C6 alkoxy, C2-C7 alkoxycarbonyl, cyclo-C3-C6 alkyloxycarbonyl, C1-C6 alkylsulfonyl, C1-C6 alkylthio, cyclo-C3-C6 alkyloxy, cyclo-C3-C6 alkyl-C1-C6 alkoxy, cyclo-C3-C6 alkylsulfonyl, cyclo-C3-C6 alkylthio or cyclo-C3-C6 alkyl-C1-C6 alkylthio group; or an optionally-substituted C1-C6 alkyl group; T and U each represent a nitrogen atom or a methine group; and V represents an oxygen atom or a sulfur atom.

The compound of the invention is useful as therapeutical agents for various ACC-related diseases.

15 Claims, No Drawings

OTHER PUBLICATIONS

Abu-Elheiga, L.et al., "Continuous Fatty Acid Oxidation and Reduced Fat Storage in Mice Lacking Acetyl-CoA Carboxylase 2" Science, vol. 294, pp. 2613-2616, 2001.

Abu-Elheiga, L. et al., "Human acetyl-CoA carboxylase: Characterizzation, molecular cloning, and evidence for two isoforms" Proc. Natl. Acad. Sci., vol. 92, pp. 4011-4015, 1995.

Beckers, A. et al., "Chemical Inhibition of Acetyl-CoA Carboxylase Induces Growth Arrest and Cytotoxicity Selectively in Cancer Cells" Cancer Res, vol. 67, No. 17, pp. 8180-8187, 2007.

Elliott, J. M. et al., "4-Oxospiro[benzopyran-2,4'-piperidines] as Class III Antiarrhythmic Agents . . . " J. Med. Chem, vol. 35, pp. 3973-3976, 1992.

Freiberg, C. et al., "Identification and Characterization of the First Class of Potent Bacterial Acetyl-CoA Carboxylase Inhibitors with Antibacterial Activitiy" The Journal of Biological Chemistry, vol. 279, No. 25, pp. 26066-26066, 2004.

Harwood, H. J, Jr. et al., "Isozyme-nonselective N-Substituted Bipiperidylcarboxamide Acetyl-CoA Carboxylase Inhibitors . . . " The Journal of Biological Chemistry, vol. 278, No. 39, pp. 37099-37111, 2003.

Quaglia, W. et al., "1'-Benzyl-3,4-dihydrospiro[2H-1-benzothiopyran-2,4'-piperidine](Spipethiane), a Potent and Highly Selective Ligand" Journal of Medicinal Chemistry, vol. 41, No. 10, pp. 1557-1560, 1998.

Savage, D. B. et al., "Reversal of diet-induced hepatic steatosis and hepatic insulin resistance by antisense oligonucleotide inhibitors of acetyl-CoA carboxylases 1 and 2" The Journal of Clinical Investigation, pp. 1-8, Dec. 2005.

Wilson, R. A. et al., "Synthesis and derivatisation of a nove spiro[1-benzofuran-2,4'-piperidin]-3-one scaffold" Org. Biomol. Chem., vol. 3, pp. 3228-3235, 2005.

Xu, A. et al., "The fat-derived hormone adiponectin alleviates alcoholic and nonalcoholic fatty liver diseases in mice" The Journal of Clinical Investigation, vol. 112, No. 1, pp. 91-100, 2003.

Database Chemcats Abstract, XP002407688, CAS-registry No. 877811-12-6, 877811-11-5 & "Interchim Intermediates", Jan. 18, 2005.

Office Action dated Jul. 31, 2007 for U.S. Appl. No. 11/487,029 dated Oct. 16, 2007.

Response to Office Action dated Jul. 31, 2007 for U.S. Appl. No. 11/487,029.

Nakamuta, M.et al., "Evaluation of fatty acid metabolism-related gene expression in nonalcoholic fatty liver disease", International Journal of Molecular Medicine, vol. 16, pp. 631-635, 2005.

SUBSTITUTED SPIROCHROMANONE DERIVATIVES

CROSS-REFERENCE TO RELATED APPLICATIONS

This application claims priority from and the benefit of U.S. Provisional Application No. 60/880,302, filed Jan. 12, 2007.

BACKGROUND OF THE INVENTION

Acetyl CoA carboxylase (hereinafter this may be abbreviated to ACC) is an enzyme that carboxylates acetyl CoA to produce malonyl CoA, and mammals have two isozymes of ACC1 and ACC2 in their own bodies. Malonyl CoA produced by ACC may be a starting material for long-chain fatty acids or neutral fats, and in addition, it may negatively control carnitine palmitoyl transferase-1 (CPT-1) that participates in oxidative decomposition of fatty acids. Of the above isozymes, ACC1 exists in cytoplasm and is considered as a rate-limiting enzyme in biosynthesis of long-chain fatty acids, while, ACC2 exists predominantly on mitochondria and is said to participate principally in oxidation of fatty acids. Accordingly, compounds capable of inhibiting ACC1 and/or ACC2 are expected not only to inhibit synthesis of fatty acids but also to reduce accumulated fats. In fact, it is shown that, as compared with normal mice, ACC2-knocked out mice hardly get fat (see *Proceedings of the National Academy of Sciences of the United States of America*, 100 (18), pp. 10207-10212, 2003).

An excess of accumulated fats may cause, for example, insulin resistance, diabetes, hypertension, hyperlipemia and obesity, and it is known that a plurality of those factors, as combined, lead to an extremely higher risk of arteriosclerosis, and the symptom is referred to as a metabolic syndrome. Further, it is known that hypertriglyceridemia or obesity leads to a higher risk of, for example, pancreatitis, liver dysfunction, cancers such as breast cancer, uterine cancer, ovarian cancer, colon cancer and prostate cancer, emmeniopathy, arthritis, gout, cholecystitis, gastroesophageal reflux, pickwickian syndrome, sleep apnea syndrome. It is well known that diabetes often causes, for example, cardiac angina, heart failure, stroke, claudication, retinopathy, eyesight failure, renal failure, neuropathy, skin ulcer, infectious diseases (see *The Merck Manual of Medical Information*, second home edition, Merck & Co., 2003). Accordingly, ACC inhibitors are useful for the treatment and/or prevention of such disorders.

ACC exists also in plants, parasites, bacteria and fungi, and it is known that it participates in the growth of cells. For example, aryloxyphenoxypropionic acid-type herbicides represented by diclofop, and cyclohexanedione-type herbicides represented by sethoxydim exert their activity by inhibiting ACC in plants (see *Biochemical Society of Transaction*, 22(3), p. 616 (1994)), and the aryloxyphenoxypropionic acids also exhibit a growth-inhibiting effect on parasites (see *Journal of Biological Chemistry*, 277 (26), pp. 23208-23215 (2002)). In addition, sorafen and moiramide B known as ACC inhibitors exhibit an antibacterial effect and an antifungal effect (see *Current Genetics*, 25 (2), pp. 95-100 (1994); *Journal of Biological Chemistry*, 279 (25), pp. 26066-26073 (2004)).

Tumor cells generally show an increased synthesis of fatty acids, and it is reported that some fatty acid synthesis inhibitors exhibit a cell growth-inhibiting effect.

Based on the above-mentioned information, ACC inhibitors are expected to be useful for the treatment and/or prevention of disorders such as hyperlipemia, fatty liver, dyslipidemia, hepatic dysfunction, obesity, diabetes, insulin resistance, metabolic syndrome, arteriosclerosis, hypertension, cardiac angina, heart failure, cardiac infarction, stroke, claudication, retinopathy, eyesight failure, renal failure, electrolyte metabolism disorder, neuropathy, skin ulcer, bulimia, pancreatitis, emmeniopathy, arthritis, gout, cholecystitis, gastroesophageal reflux, pickwickian syndrome, sleep apnea syndrome, neoplasm, infectious diseases, such as parasite infection, bacterial infection, viral infection and fungal infection, and also as herbicides.

Up to the present, for example, those described in a pamphlet of WO 2003/094912, a pamphlet of WO 2003/072197, a pamphlet of WO 2003/059886, a pamphlet of WO 2003/059871 are known as compounds capable of inhibiting ACC, but the compounds described in these references are totally different from the compounds of the present invention in point of their structures.

On the other hand, various compounds having the same spirochromanone skeleton as that of the compounds of the present invention are disclosed in a pamphlet of WO 95/30642, EP 431973A or a pamphlet of WO 2004/092179. However, these references do neither disclose nor suggest the ACC-inhibiting effect of those compounds or the compounds of the present invention.

SUMMARY OF THE INVENTION

The present invention is useful in the field of medicines. More precisely, substituted spirochromanone derivatives of the invention are acetyl CoA carboxylase inhibitors useful as therapeutical agents for various vascular diseases, nervous system diseases, metabolic diseases, genital diseases, digestive system diseases, respiratory diseases, neoplasm and infectious diseases. In addition, they are also useful as herbicides.

DETAILED DESCRIPTION OF THE INVENTION

The present invention provides compounds of the following general formula (I), and salts and esters thereof, which have a strong ACC-inhibiting effect:

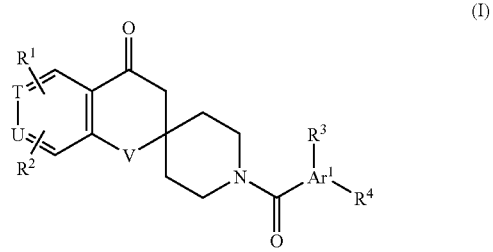

(I)

wherein, $Ar^1$ represents a group formed from an aromatic ring selected from a group consisting of indole, 1H-indazole, 2H-indazole, 1H-thieno[2,3-c]pyrazole, 1H-pyrazolo[3,4-b]pyridine, benzo[b]furan, benzimidazole, benzoxazole, 1,2-benzisoxazole and imidazo[1,2-a]pyridine, having $R^3$ and $R^4$, and optionally having a substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a carboxyl group and a carbamoyl group;

$R^1$ and $R^2$ each independently represent a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of $-Q^1-N(R^a)-Q^2-R^b$;

a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;

an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a C1-C6 alkyl group or a C2-C6 alkenyl group having the aryl or heterocyclic group;

$R^3$ and $R^4$ each independently represent a hydrogen atom, a halogen atom, a nitro group, a cyclo-C3-C6 alkyl group, a carbamoyl group optionally substituted with a C1-C6 alkyl or cyclo-C3-C6 alkyl group, or a group of —N($R^e$)$R^f$;

a C2-C7 alkanoyl group, a C1-C6 alkoxy group, a C2-C7 alkoxycarbonyl group, a cyclo-C3-C6 alkyloxycarbonyl group, a C1-C6 alkylsulfonyl group, a C1-C6 alkylthio group, a cyclo-C3-C6 alkyloxy group, a cyclo-C3-C6 alkyl-C1-C6 alkoxy group, a cyclo-C3-C6 alkylsulfonyl group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxycarbonyl group, the cyclo-C3-C6 alkyloxy group, the cyclo-C3-C6 alkyl-C1-C6 alkoxy group, the cyclo-C3-C6 alkylsulfonyl group, the cyclo-C3-C6 alkylthio group or the cyclo-C3-C6 alkyl-C1-C6 alkylthio group may be interrupted by an oxygen atom, a sulfur atom or an imino group; or a C1-C6 alkyl group optionally having a substituent selected from a group consisting of a halogen atom, a hydroxyl group and a cyclo-C3-C6 alkyl group;

$Q^1$ and $Q^2$ each independently represent a single bond, or a group of —CO—, —SO$_2$— or —C($R^g$)($R^h$)—;

$R^a$ and $R^b$ each independently represent a hydrogen atom, a C2-C6 alkenyl group, a C1-C6 alkoxy group, a cyclo-C3-C6 alkyloxy group, a halo-C1-C6 alkoxy group, a cyclo-C3-C6 alkyl group, an aralkyloxy group, a carbamoyl group, a C2-C7 alkoxycarbonyl group, or a group of —N($R^i$)$R^j$;

a C1-C6 alkyl group optionally having a substituent selected from a group consisting of a halogen atom, a C1-C6 alkoxy group, a carbamoyl group and a C2-C7 alkoxycarbonyl group; or a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group;

$R^c$, $R^d$, $R^g$, $R^h$, $R^i$ and $R^j$ each independently represent a hydrogen atom, a C1-C6 alkyl group, or a halo-C1-C6 alkyl group;

$R^e$ and $R^f$ each independently represent a hydrogen atom, a C1-C6 alkyl group, or a halo-C1-C6 alkyl group, or taken together, they may form a C2-C5 alkylene group optionally interrupted by an oxygen atom, a sulfur atom or an imino group;

T and U each independently represent a nitrogen atom or a methine group; and

V represents an oxygen atom or a sulfur atom.

The compounds (I) of the invention have an ACC-inhibiting effect and are useful as therapeutical agents for various ACC-related disorders, for example, vascular diseases such as hypertension, cardiac angina, heart failure, cardiac infarction, stroke, claudication, diabetic nephropathy, diabetic retinopathy, eyesight failure, electrolyte metabolism disorder, arteriosclerosis; nervous system diseases such as bulimia, diabetic neuropathy; metabolic diseases such as metabolic syndrome, obesity, diabetes, insulin resistance, hyperlipemia, hypercholesterolemia, hypertriglyceridemia, dyslipidemia, nonalcoholic fatty liver, hormone secretion failure, gout, and hepatic steatosis; genital diseases such as emmeniopathy, sexual dysfunction; digestive system diseases such as liver dysfunction, pancreatitis, cholecystitis, gastroesophageal reflux; respiratory diseases such as obesity-hypoventilation syndrome (pickwickian syndrome), sleep apnea syndrome; infectious diseases caused by bacteria, fungi or parasites; malignant neoplasm; and inflammatory diseases such as arthritis and skin ulcer. The compounds are also useful as herbicides.

In particular, the compounds (I) of the invention are useful as therapeutical agents, for example, for metabolic syndrome, fatty liver, hyperlipemia, obesity, diabetes, bulimia, malignant neoplasm and infectious diseases.

The invention relates to the compounds of formula (I), and their salts and esters, and to their production and use.

The meanings of the terms used herein are mentioned below, and the invention is described in more detail hereinunder.

"Halogen atom" includes a fluorine atom, a chlorine atom, a bromine atom, and an iodine atom.

"C1-C6 alkyl group" means a linear or branched alkyl group having from 1 to 6 carbon atoms, and it includes, for example, a methyl group, an ethyl group, a propyl group, an isopropyl group, a butyl group, an isobutyl group, a sec-butyl group, a tert-butyl group, a pentyl group, an isopentyl group, a hexyl group, and an isohexyl group.

"Halo-C1-C6 alkyl group" means the above-mentioned C1-C6 alkyl group which is substituted with the above-mentioned halogen atom(s) of the same type or different types and which has one or two or more, but preferably from 1 to 3 unlimited substitutable positions, and it includes, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, and an iodomethyl group.

"Hydroxy-C1-C6 alkyl group" means the above-mentioned C1-C6 alkyl group which is substituted with hydroxyl group(s) and which has one or two or more, but preferably one or two unlimited substitutable positions, and it includes, for example, a hydroxymethyl group, a 2-hydroxyethyl group, a 1-hydroxy-1-methylethyl group, a 1,2-dihydroxyethyl group, and a 3-hydroxypropyl group.

"Cyclo-C3-C6 alkyl group" means a cycloalkyl group having from 3 to 6 carbon atoms, and it includes a cyclopropyl group, a cyclobutyl group, a cyclopentyl group, and a cyclohexyl group.

"C2-C6 alkenyl group" means a linear or branched alkenyl group having from 2 to 6 carbon atoms, and it includes, for example, a vinyl group, a 1-propenyl group, a 2-propenyl group, an isopropenyl group, a 3-butenyl group, a 2-butenyl group, a 1-butenyl group, a 1-methyl-2-propenyl group, a 1-methyl-1-propenyl group, a 1-ethyl-1-ethenyl group, a 2-methyl-2-propenyl group, a 2-methyl-1-propenyl group, a 3-methyl-2-butenyl group, and a 4-pentenyl group.

"C1-C6 alkoxy group" means a linear or branched alkoxy group having from 1 to 6 carbon atoms, and it includes, for example, a methoxy group, an ethoxy group, a propoxy group, an isopropoxy group, a butoxy group, a sec-butoxy group, an isobutoxy group, a tert-butoxy group, a pentyloxy group, an isopentyloxy group, a hexyloxy group, and an isohexyloxy group.

"Halo-C1-C6 alkoxy group" means the above-mentioned C1-C6 alkoxy group which is substituted with the above-mentioned halogen atom(s) of the same type or different types and which has one or two or more, but preferably from 1 to 3 unlimited substitutable positions, and it includes, for example, a fluoromethoxy group, a difluoromethoxy group, a trifluoromethoxy group, a 2-fluoroethoxy group, a 1,2-difluoroethoxy group, a 2,2,2-trifluoroethoxy group, a chloromethoxy group, a 2-chloroethoxy group, a 1,2-dichloroethoxy group, a bromomethoxy group, and an iodomethoxy group.

"C1-C6 alkylthio group" means a linear or branched alkylthio group having from 1 to 6 carbon atoms, and it includes, for example, a methylthio group, an ethylthio group, a propylthio group, an isopropylthio group, a butylthio group, a sec-butylthio group, an isobutylthio group, a tert-butylthio group, a pentylthio group, an isopentylthio group, a hexylthio group, and an isohexylthio group.

"C2-C7 alkanoyl group" means an alkanoyl group having the above-mentioned C1-C6 alkyl group, or that is, an alkanoyl group having from 2 to 7 carbon atoms, and it includes, for example, an acetyl group, a propionyl group, a butyryl group, an isobutyryl group, a valeryl group, an isovaleryl group, and a pivaloyl group.

"Halo-C2-C7 alkanoyl group" means the above-mentioned C2-C7 alkanoyl group which is substituted with the above-mentioned halogen atom(s) of the same type or different types and which has one or two or more, but preferably from 1 to 3 unlimited substitutable positions, and it includes, for example, a chloroacetyl group, a dichloroacetyl group, a fluoroacetyl group, a difluoroacetyl group, a 3-chloropropionyl group, and a 3-fluoropropionyl group.

"C2-C7 alkoxycarbonyl group" means an alkoxycarbonyl group having the above-mentioned C1-C6 alkoxy group, or that is, an alkoxycarbonyl group having from 2 to 7 carbon atoms, and it includes, for example, a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, and a pentyloxycarbonyl group.

"Halo-C2-C7 alkoxycarbonyl group" means a haloalkoxycarbonyl group having the above-mentioned halo-C1-C6 alkoxy group, and it includes, for example, a 2,2-difluoroethoxycarbonyl group.

"Carbamoyl-C1-C6 alkoxy group" means the above-mentioned C1-C6 alkoxy group substituted with one or two or more, preferably one carbamoyl group at the substitutable position thereof, and it includes, for example, a carbamoylmethoxy group, a 1-carbamoylethoxy group, a 2-carbamoylethoxy group, a 2-carbamoylpropoxy group, and a 3-carbamoylpropoxy group.

"Carboxy-C2-C6 alkenyl group" means the above-mentioned C2-C6 alkenyl group substituted with one or two or more, preferably one carboxyl group at any substitutable position thereof, and it includes, for example, a 1-carboxyvinyl group, a 2-carboxyvinyl group, a 2-carboxy-1-propenyl group, a 3-carboxy-1-propenyl group, a 3-carboxy-2-propenyl group, a 4-carboxy-3-butenyl group, and a 4-carboxy-2-butenyl group.

"C2-C7 alkanoyloxy group" means an alkanoyloxy group having the above-mentioned C2-C7 alkanoyl group, and it includes, for example, an acetyloxy group, a propionyloxy group, a butyryloxy group, an isobutyryloxy group, a valeryloxy group, an isovaleryloxy group, and a pivaloyloxy group.

"C1-C6 alkylsulfonyl group" means a linear or branched alkylsulfonyl group having from 1 to 6 carbon atoms, and it includes, for example, a methylsulfonyl group, an ethylsulfonyl group, a propylsulfonyl group, an isopropylsulfonyl group, a butylsulfonyl group, a sec-butylsulfonyl group, an isobutylsulfonyl group, a tert-butylsulfonyl group, a pentylsulfonyl group, an isopentylsulfonyl group, a hexylsulfonyl group, and an isohexylsulfonyl group.

"Cyclo-C3-C6 alkylsulfonyl group" means a cycloalkylsulfonyl group having the above-mentioned cyclo-C3-C6 alkyl group, or that is a cycloalkylsulfonyl group having from 3 to 6 carbon atoms, and it includes, for example, a cyclopropylsulfonyl group, a cyclobutylsulfonyl group, and a cyclopentylsulfonyl group.

"C2-C7 alkanoyloxy-C1-C6 alkyl group" means the above-mentioned C1-C6 alkyl group substituted with one or two or more, preferably one above-mentioned C2-C7 alkanoyloxy group at any substitutable position thereof, and it includes, for example, an acetyloxymethyl group, a propionyloxymethyl group, a butyryloxymethyl group, an isobutyryloxymethyl group, a valeryloxymethyl group, an isovaleryloxymethyl group, and a pivaloyloxymethyl group.

"Aryl group" includes, for example, a phenyl group, a 1-naphthyl group, and a 2-naphthyl group.

"Aralkyl group" means the above-mentioned alkyl group which is substituted by the above-mentioned aryl group and which has one or two or more, but preferably one unlimited substitutable position, and it includes, for example, a benzyl group, a 1-phenylethyl group, a phenethyl group, a 1-naphthylmethyl group, and a 2-naphthylmethyl group.

"Aralkyloxy group" means an aralkyloxy group having the above-mentioned aralkyl group, and it includes, for example, a benzyloxy group, a 1-phenylethyloxy group, a phenethyloxy group, a 1-naphthylmethyloxy group, and a 2-naphthylmethyloxy group.

"Aralkyloxycarbonyl group" means an aralkyloxycarbonyl group having the above-mentioned aralkyloxy group, and it includes, for example, a benzyloxycarbonyl group, a 1-phenylethyloxycarbonyl group, a phenethyloxycarbonyl group, a 1-naphthylmethyloxycarbonyl group, and a 2-naphthylmethyloxycarbonyl group.

"Heteroaromatic group" means a 5-membered or 6-membered monocyclic aromatic heterocyclic group which has one or two or more, but preferably from 1 to 3 and the same or different hetero atoms selected from a group consisting of oxygen, nitrogen and sulfur atoms, or means a condensed-cyclic aromatic heterocyclic group which is constructed through condensation of the monocyclic aromatic heterocyclic group and the above-mentioned aryl group or through condensation of those, same or different monocyclic aromatic heterocyclic groups; and it includes, for example, a pyrrolyl group, a furyl group, a thienyl group, an imidazolyl group, a pyrazolyl group, a thiazolyl group, an isothiazolyl group, an oxazolyl group, an isoxazolyl group, a triazolyl group, a tetrazolyl group, an oxadiazolyl group, a 1,2,3-thiadiazolyl group, a, 1,2,4-thiadiazolyl group, a 1,3,4-thiadiazolyl group, a pyridyl group, a pyrazinyl group, a pyrimidinyl group, a pyridazinyl group, a 1,2,4-triazinyl group, a 1,3,5-triazinyl group, an indolyl group, a benzofuranyl group, a benzothienyl group, a benzimidazolyl group, a benzoxazolyl group, a benzisoxazolyl group, a benzothiazolyl group, a benzisothiazolyl group, an indazolyl group, a purinyl group, a quinolyl group, an isoquinolyl group, a phthalazinyl group, a naphthyridinyl group, a quinoxalinyl group, a quinazolinyl group, a cinnolinyl group, a pteridinyl group, and a pyrido[3,2-b]pyridyl group.

"Heterocyclic group" means a 3- to 7-membered monocyclic heterocyclic group which has one or two or more, but preferably from 1 to 3 and the same or different hetero atoms selected from a group consisting of oxygen, nitrogen and sulfur atoms, or means a condensed-cyclic heterocyclic group which is constructed through condensation of the monocyclic heterocyclic group and a 3- to 7-membered carbocyclic group or through condensation of those, same or different monocyclic heterocyclic groups; and it includes the above-mentioned heteroaromatic groups. Its examples are, in addition to those listed hereinabove for the above-mentioned heteroaromatic group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a piperidyl group, a piperazinyl group, a morpholinyl group, and a thiomorpholinyl group.

"Carbamoyl group optionally substituted with a C1-C6 alkyl group or a cyclo-C3-C6 alkyl group" means a carbamoyl group which may be substituted with the above-mentioned C1-C6 alkyl group and/or the above-mentioned cyclo-C3-C6 alkyl group, and it includes, for example, a carbamoyl group, a methylcarbamoyl group, a dimethylcarbamoyl group, a cyclopropylcarbamoyl group, and a cyclopropyl(methyl)carbamoyl group.

"Cyclo-C3-C6 alkyloxy group" means a cycloalkyloxy group having the above-mentioned cyclo-C3-C6 alkyl group, and it includes a cyclopropyloxy group, a cyclobutyloxy group, a cyclopentyloxy group, and a cyclohexyloxy group.

"Cyclo-C3-C6 alkyloxycarbonyl group" means a cycloalkyloxycarbonyl group having the above-mentioned cyclo-C3-C6 alkyloxy group, and it includes, for example, a cyclopropyloxycarbonyl group, a cyclobutyloxycarbonyl group.

"Cyclo-C3-C6 alkyl-C1-C6 alkoxy group" means the above-mentioned C1-C6 alkoxy group which is substituted by the above-mentioned cyclo-C3-C6 alkyl group and which has one or two or more, but preferably one unlimited substitutable position, and it includes, for example, a cyclopropylmethoxy group, a cyclobutylmethoxy group, a cyclopentylmethoxy group, a cyclopropylethoxy group, a cyclobutylethoxy group, and a cyclopropylpropoxy group.

"Cyclo-C3-C6 alkylthio group" means a cycloalkylthio group having the above-mentioned cyclo-C3-C6 alkyl group, and it includes a cyclopropylthio group, a cyclobutylthio group, a cyclopentylthio group, and a cyclohexylthio group.

"Cyclo-C3-C6 alkyl-C1-C6 alkylthio group" means the above-mentioned C1-C6 alkylthio group substituted with one or two or more, preferably one above-mentioned cyclo-C3-C6 alkyl group at any substitutable position thereof, and it includes, for example, a cyclopropylmethylthio group, a cyclobutylmethylthio group, a cyclopentylmethylthio group, a cyclopropylethylthio group, a cyclobutylethylthio group, and a cyclopropylpropylthio group.

"Cyclo-C3-C6 alkyl group optionally interrupted by an oxygen atom, a sulfur atom or an imino group" means that the cyclo-C3-C6 alkyl group is the above-mentioned cyclo-C3-C6 alkyl group, or means that the carbon atom(s) constituting the cyclo-C3-C6 alkyl group is/are replaced with one or two or more, preferably one oxygen atom, sulfur atom or imino group so that the cyclo-C3-C6 alkyl group is interrupted by it. The group includes, for example, those listed hereinabove as the above-mentioned cyclo-C3-C6 alkyl group, and in addition to these, an oxiranyl group, an oxetanyl group, a tetrahydrofuranyl group, a tetrahydro-2H-pyranyl group, a thioranyl group, a thietanyl group, a tetrahydrothienyl group, a tetrahydro-2H-thiopyranyl group, an aziridinyl group, an azetidinyl group, a pyrrolidinyl group, and a piperidyl group.

"C1-C6 alkylene group" means a linear or branched alkylene group having from 1 to 6 carbon atoms, and it includes, for example, a methylene group, an ethylene group, a trimethylene group, a tetramethylene group, a pentamethylene group, and a hexamethylene group.

"C2-C5 alkylene group optionally interrupted by an oxygen atom, a sulfur atom or an imino group" means an alkylene group having from 2 to 5 carbon atoms, which is interrupted or not by one or two or more, but preferably one oxygen atom, sulfur atom or imino group at any position of the alkylene chain thereof capable of being interrupted by it, and this includes, for example, an ethylene group, a trimethylene group, a tetramethylene group, a pentamethylene group, a 2-oxatetramethylene group, a 2-oxapentamethylene group, 3-oxapentamethylene group, a 2-thiatetramethylene group, a 2-thiapentamethylene group, a 3-thiapentamethylene group, a 2-azatetramethylene group, 2-azapentamethylene group, and a 3-azapentamethylene group.

"Salts" of the compound of formula (I) means pharmaceutically acceptable and common salts, including, for example, base addition salts of the compound having a carboxyl group, a hydroxyl group or an acidic heterocyclic group such as a tetrazolyl group, with a base added to the carboxyl group, the hydroxyl group or the acidic heterocyclic group of the compound; and acid addition salts of the compound having an amino group or a basic heterocyclic group, with an acid added to the amino group or the basic heterocyclic group of the compound.

The base addition salts include, for example, alkaline metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

The acid addition salts include, for example, inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

"Esters" of the compound of formula (I) mean those of the compound having a carboxyl group, which are esterified at the carboxyl group of the compound and which are pharmaceutically acceptable and common esters, including, for example, esters with a C1-C6 (cyclo)alkyl group such as a methyl group, an ethyl group, a propyl group, an isopropyl group, a butyl group, a sec-butyl group, a tert-butyl group, a pentyl group, an isopentyl group, a neopentyl group, a cyclopropyl group, a cyclobutyl group or cyclopentyl group; esters with an aralkyl group such as a benzyl group or a phenethyl group; esters with a C2-C6 alkenyl group such as an allyl group (2-propenyl group), or a 2-butenyl group; esters with a C1-C6 alkoxy-C1-C6 alkyl group such as a methoxymethyl group, a 2-methoxyethyl group or a 2-ethoxyethyl group;

esters with a C2-C7 alkanoyloxy-C1-C6 alkyl group such as an acetoxymethyl group, a pivaloyloxymethyl group or a 1-pivaloyloxyethyl group; esters with a C2-C7 alkoxycarbonyl-C1-C6 alkyl group such as a methoxycarbonylmethyl group or an isopropoxycarbonylmethyl group; esters with a carboxy-C1-C6 alkyl group such as a carboxymethyl group; esters with a C2-C7 alkoxycarbonyloxy-C1-C6 alkyl group such as a 1-(ethoxycarbonyloxy)ethyl group or a 1-(cyclohexyloxycarbonyloxy)ethyl group; esters with a carbamoyloxy-C1-C6 alkyl group such as a carbamoyloxymethyl group; esters with a phthalidyl group; and esters with a (5-substituted-2-oxo-1,3-dioxol-4-yl)methyl group such as a (5-methyl-2-oxo-1,3-dioxol-4-yl)methyl group.

"Therapeutical agent" means a medicine used for the treatment and/or prevention of various disorders.

For more concrete disclosure of the compounds of formula (I) of the invention, the symbols used in formula (I) are described in detail hereinunder with reference to their preferred examples.

$Ar^1$ represents a group formed from an aromatic ring selected from a group consisting of indole, 1H-indazole, 2H-indazole, 1H-thieno[2,3-c]pyrazole, 1H-pyrazolo[3,4-b]pyridine, benzo[b]furan, benzimidazole, benzoxazole, 1,2-benzisoxazole and imidazo[1,2-a]pyridine, having $R^3$ and $R^4$, and optionally having a substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a carboxyl group and a carbamoyl group.

"Group formed from an aromatic ring selected from a group consisting of indole, 1H-indazole, 2H-indazole, 1H-thieno[2,3-c]pyrazole, 1H-pyrazolo[3,4-b]pyridine, benzo[b]furan, benzimidazole, benzoxazole, 1,2-benzisoxazole and imidazo[1,2-a]pyridine" means an atomic group formed by formally removing the hydrogen atom from the ring-constituting atoms of the aromatic ring. The group includes an at least tri-substituted group, necessarily bonding to the adjacent carbonyl group and to $R^3$ and $R^4$, and as the case may be, it may have an additional substituent, and may include a 4-substituted or 5-substituted or more poly-substituted group, bonding to the substituent. Each independently, $R^3$ and $R^4$ may be a hydrogen atom, and therefore, the group includes a mono-substituted or di-substituted group.

The substituent which the group may additionally have may be one or two or more, preferably one selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a carboxyl group and a carbamoyl group.

$Ar^1$ is especially preferably a 3-substituted or 4-substituted group, which is formed from an aromatic ring such as indole, 1H-thieno[2,3-c]pyrazole, benzo[b]furan, benzimidazole or imidazo[1,2-a]pyridine, more preferably indole.

$R^3$ and $R^4$ may bond each independently to any bondable position on $Ar^1$.

The substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a carboxyl group and a carbamoyl group may be on any desired and substitutable position of $Ar^1$ except the position at which the above mentioned $R^3$ and $R^4$ bond.

The halogen atom for the substituent is, for example, preferably a fluorine atom, a chlorine atom, a bromine atom.

The C1-C6 alkyl group for the substituent is, for example, preferably a methyl group, an ethyl group.

The halo-C1-C6 alkyl group for the substituent is, for example, preferably a fluoromethyl group, a difluoromethyl group, a trifluoromethyl group.

The hydroxy-C1-C6 alkyl group for the substituent is, for example, preferably a hydroxymethyl group, a 1-hydroxyethyl group, a 2-hydroxyethyl group.

The cyclo-C3-C6 alkyl group for the substituent is, for example, preferably a cyclopropyl group.

The C2-C6 alkenyl group for the substituent is, for example, preferably a 2-propenyl group, an isopropenyl group.

The C1-C6 alkoxy group for the substituent is, for example, preferably a methoxy group, an ethoxy group.

The halo-C1-C6 alkoxy group for the substituent is, for example, preferably a difluoromethoxy group.

The C1-C6 alkylthio group for the substituent is, for example, preferably a methylthio group, an ethylthio group.

The substituent is, for example, preferably a halogen atom, a hydroxyl group, a C1-C6 alkyl group, a halo-C1-C6 alkyl group, a hydroxy-C1-C6 alkyl group, a cyclo-C1-C6 alkyl group, a C1-C6 alkoxy group, a halo-C1-C6 alkoxy group and carbamoyl group.

$R^3$ and $R^4$ each independently represent a hydrogen atom, a halogen atom, a nitro group, a cyclo-C3-C6 alkyl group, a carbamoyl group optionally substituted with a C1-C6 alkyl or cyclo-C3-C6 alkyl group, or a group of —N($R^e$)$R^f$;

a C2-C7 alkanoyl group, a C1-C6 alkoxy group, a C2-C7 alkoxycarbonyl group, a cyclo-C3-C6 alkyloxycarbonyl group, a C1-C6 alkylsulfonyl group, a C1-C6 alkylthio group, a cyclo-C3-C6 alkyloxy group, a cyclo-C3-C6 alkyl-C1-C6 alkoxy group, a cyclo-C3-C6 alkylsulfonyl group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxycarbonyl group, the cyclo-C3-C6 alkyloxy group, the cyclo-C3-C6 alkyl-C1-C6 alkoxy group, the cyclo-C3-C6 alkylsulfonyl group, the cyclo-C3-C6 alkylthio group or the cyclo-C3-C6 alkyl-C1-C6 alkylthio group may be interrupted by an oxygen atom, a sulfur atom or an imino group; or a C1-C6 alkyl group optionally having a substituent selected from a group consisting of a halogen atom, a hydroxyl group and a cyclo-C3-C6 alkyl group.

The halogen atom for $R^3$ and $R^4$ is, for example, preferably a fluorine atom, a chlorine atom.

The cyclo-C3-C6 alkyl group for $R^3$ and $R^4$ is, for example, preferably a cyclopropyl group.

The carbamoyl group optionally substituted with a C1-C6 alkyl group or a cyclo-C3-C6 alkyl group for $R^3$ and $R^4$ is, for example, preferably a carbamoyl group, a methylcarbamoyl group, a dimethylcarbamoyl group.

In the group of —N($R^e$)$R^f$ for $R^3$ and $R^4$, $R^e$ and $R^f$ each independently represent a hydrogen atom, a C1-C6 alkyl group or a halo-C1-C6 alkyl group, or taken together, they may form a C2-C5 alkylene group optionally interrupted by an oxygen atom, a sulfur atom or an imino group.

The C1-C6 alkyl group for $R^e$ and $R^f$ is, for example, preferably a methyl group, an ethyl group.

The halo-C1-C6 alkyl group for $R^e$ and $R^f$ is, for example, preferably a fluoromethyl group, a difluoromethyl group.

The C2-C5 alkylene group optionally interrupted by an oxygen atom, a sulfur atom or an imino group, which is formed by $R^e$ and $R^f$ taken together, is for example, preferably a tetramethylene group, a pentamethylene group, a 3-oxapentamethylene group. The group form, along with the adjacent nitrogen atom, a 1-pyrrolidinyl group, a piperidino group, a morpholino group, etc.

Preferably, for example, $R^e$ and $R^f$ each are a C1-C6 alkyl group, or taken together, form the above-mentioned C2-C5 alkylene group.

Accordingly, the group of —N($R^e$)$R^f$ for is, for example, more concretely a dimethylamino group, a 1-pyrrolidinyl group, or a morpholino group.

In "a C2-C7 alkanoyl group, a C1-C6 alkoxy group, a C2-C7 alkoxycarbonyl group, a cyclo-C3-C6 alkyloxycarbonyl group, a C1-C6 alkylsulfonyl group, a C1-C6 alkylthio group, a cyclo-C3-C6 alkyloxy group, a cyclo-C3-C6 alkyl-C1-C6 alkoxy group, a cyclo-C3-C6 alkylsulfonyl group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxycarbonyl group, the cyclo-C3-C6 alkyloxy group, the cyclo-C3-C6 alkyl-C1-C6 alkoxy group, the cyclo-C3-C6 alkylsulfonyl group, the cyclo-C3-C6 alkylthio group or the cyclo-C3-C6 alkyl-C1-C6 alkylthio group may be interrupted by an oxygen atom, a sulfur atom or an imino group" for $R^3$ and $R^4$, the halogen atom for the substituent is, for example, preferably a fluorine atom, a chlorine atom.

The C2-C7 alkanoyl group optionally substituted with a halogen atom or a hydroxyl group for $R^3$ and $R^4$ is, for example, preferably an acetyl group, a propanoyl group, a trifluoroacetyl group, a hydroxyacetyl group, more preferably an acetyl group, a hydroxyacetyl group.

The C1-C6 alkoxy group optionally substituted with a halogen atom or a hydroxyl group for $R^3$ and $R^4$ is, for example, preferably a methoxy group, an ethoxy group, a propoxy group, an isopropoxy group, a difluoromethoxy group, a 2,2-difluoroethoxy group, a 2-hydroxyethoxy group, more preferably a methoxy group, an ethoxy group.

The C2-C7 alkoxycarbonyl group optionally substituted with a halogen atom or a hydroxyl group for $R^3$ and $R^4$ is, for example, preferably a methoxycarbonyl group, an ethoxycarbonyl group, a propoxycarbonyl group, an isopropoxycarbonyl group, a difluoromethoxycarbonyl group, a 2,2-difluoroethoxycarbonyl group, a 2-hydroxyethoxycarbonyl group, more preferably a methoxycarbonyl group, an ethoxycarbonyl group.

The cyclo-C3-C6 alkyloxycarbonyl group optionally substituted with a halogen atom or a hydroxyl group for $R^3$ and $R^4$ is, for example, preferably a cyclopropyloxycarbonyl group, a difluorocyclopropyloxycarbonyl group, more preferably a cyclopropyloxycarbonyl group.

The C1-C6 alkylsulfonyl group optionally substituted with a halogen atom or a hydroxyl group for $R^3$ and $R^4$ is, for example, preferably a methylsulfonyl group, an ethylsulfonyl group, a difluoromethylsulfonyl group, a trifluoromethylsulfonyl group, a 2-hydroxyethylsulfonyl group.

The C1-C6 alkylthio group optionally substituted with a halogen atom or a hydroxyl group for $R^3$ and $R^4$ is, for example, preferably a methylthio group, an ethylthio group, a difluoromethylthio group, a 2-hydroxyethylthio group.

The cyclo-C3-C6 alkyloxy group optionally substituted with a halogen atom or a hydroxyl group for $R^3$ and $R^4$ is, for example, preferably a cyclopropyloxy group, a 3-tetrahydrofuranyloxy group.

The cyclo-C3-C6 alkyl-C1-C6 alkoxy group optionally substituted with a halogen atom or a hydroxyl group for $R^3$ and $R^4$ is, for example, preferably a cyclopropylmethoxy group, a 3-tetrahydrofuranylmethoxy group.

The cyclo-C3-C6 alkylsulfonyl group optionally substituted with a halogen atom or a hydroxyl group for $R^3$ and $R^4$ is, for example, preferably a cyclopropylsulfonyl group.

The cyclo-C3-C6 alkylthio group optionally substituted with a halogen atom or a hydroxyl group for $R^3$ and $R^4$ is, for example, preferably a cyclopropylthio group, a 3-tetrahydrothienylthio group.

The cyclo-C3-C6 alkyl-C1-C6 alkylthio group optionally substituted with a halogen atom or a hydroxyl group for $R^3$ and $R^4$ is, for example, preferably a cyclopropylmethylthio group, a 3-tetrahydrothienylmethylthio group.

Of the C2-C7 alkanoyl group, the C1-C6 alkoxy group, the C2-C7 alkoxycarbonyl group, the cyclo-C3-C6 alkyloxycarbonyl group, the C1-C6 alkylsulfonyl group, the C1-C6 alkylthio group, cyclo-C3-C6 alkyloxy group, the cyclo-C3-C6 alkyl-C1-C6 alkoxy group, the cyclo-C3-C6 alkylsulfonyl group, the cyclo-C3-C6 alkylthio group or the cyclo-C3-C6 alkyl-C1-C6 alkylthio group, optionally substituted with a halogen atom or a hydroxyl group, for $R^3$ and $R^4$, for example, preferred is a C1-C6 alkoxy group optionally substituted with a halogen atom or a hydroxyl group.

"C1-C6 alkyl group optionally having a substituent selected from a group consisting of a halogen atom, a hydroxyl group and a cyclo-C3-C6 alkyl group" for $R^3$ and $R^4$, means the above-mentioned, unsubstituted C1-C6 alkyl group, or the above-mentioned C1-C6 alkyl group having a substituent at any substitutable position thereof, in which the substituent is one or two or more, the same or different, preferably one or two groups selected from a halogen atom, a hydroxyl group and a cyclo-C3-C6 alkyl group.

The halogen atom for the substituent is, for example, preferably a fluorine atom, a chlorine atom.

The cyclo-C3-C6 alkyl group for the substituent is, for example, preferably a cyclopropyl group.

The C1-C6 alkyl group optionally having the substituent for $R^3$ and $R^4$ is, for example, preferably a methyl group, an ethyl group, an isopropyl group, a fluoromethyl group, a difluoromethyl group, a trifluoromethyl group, a 2-fluoroethyl group, a 2,2-difluoroethyl group, a hydroxymethyl group, a 2-hydroxyethyl group, a cyclopropylmethyl group.

$R^3$ and $R^4$ are, for example, preferably a nitro group, a cyclo-C3-C6 alkyl group, a carbamoyl group, a C1-C6 alkoxy group optionally substituted with a hydroxyl group, or a C1-C6 alkyl group optionally substituted with a hydroxyl group; more preferably, $R^3$ is a C1-C6 alkoxy group optionally substituted with a hydroxyl group, and $R^4$ is a cyclo-C3-C6 alkyl group, a C1-C6 alkoxy group or a C1-C6 alkyl group.

Accordingly, in the compounds of the invention, the group of the following formula:

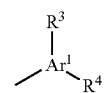

is preferably formed through combination of the above-mentioned preferred groups; for example, it is preferably a 1-cyclopropyl-7-methoxy-5-indolyl group, a 1-cyclopropyl-7-ethoxy-5-indolyl group, a 3-chloro-1-cyclopropyl-7-ethoxy-5-indolyl group, a 1-ethyl-4-nitro-6-indolyl group, a 1-ethyl-4-methoxy-6-indolyl group, a 1-ethyl-4-(2-hydroxyethyl)-6-indolyl group, a 1-ethyl-4-(2-hydroxyethoxy)-6-indolyl group, a 1-(2-hydroxyethyl)-4-methoxy-6-indolyl group, a 1,4-dimethoxy-6-indolyl group, a 1-ethoxy-4-methoxy-6-indolyl group, a 4-ethoxy-1-methoxy-6-indolyl group, a 1,4-diethoxy-6-indolyl group, a 3-chloro-1,4-dimethoxy-6-indolyl group, a 1,4-dimethoxy-3-methyl-6-indolyl group, a 1-cyclopropyl-4-methoxy-6-indolyl group, a 1-cyclopropyl-4-ethoxy-6-indolyl group, a 1-cyclopropyl-4-(2-hydroxyethoxy)-6-indolyl group, a 3-chloro-1-cyclopropyl-4-methoxy-6-indolyl group, a 3-chloro-1-cyclopropyl-4-ethoxy-6-indolyl group, a 3-bromo-1-cyclopropyl-4-ethoxy-6-indolyl group, a 1-cyclopropyl-3-methyl-4-methoxy-6-indolyl group, a 1-cyclopropyl-4-ethoxy-3-methyl-6-indolyl group, a 3-carboxy-1-cyclopropyl-4-ethoxy-6-indolyl group, a 3-carbamoyl-1-cyclopropyl-6-indolyl group, a 3-carbamoyl-1-cyclopropyl-4-ethoxy-6-indolyl group, a 1-cyclopropyl-4-ethoxy-3-methylcarbamoyl-6-indolyl group, a 1-ethyl-4-morpholino-6-indolyl group, a 1-ethyl-4-methoxy-1H-indazol-6-yl group, a 2-ethyl-4-methoxy-2H-indazol-6-yl group, a 1-ethyl-3-methyl-1H-thieno[2,3-c]pyrazol-5-yl group, a 7-methoxy-3-methyl-1H-pyrazolo[3,4-b]pyridin-5-yl group, a 4-acetyl-7-methoxybenzo[b]furan-2-yl group, a 1-ethyl-7-methoxybenzimidazol-5-yl group, a 3-ethyl-7-methoxybenzimidazol-5-yl group, a 3-cyclopropyl-7-methoxybenzimidazol-5-yl group, a 1,3-diethyl-7-methoxy-2-oxo-1,2-dihydrobenzimidazol-5-yl group, a 2-cyclopropyl-7-ethoxybenzoxazol-5-yl group, a 3-cyclopropyl-7-ethoxy-1,2-benzisoxazol-5-yl group, a 3-cyclopropyl-8-methoxyimidazo[1,2-a]pyridin-6-yl group; above all, more preferably a 1-ethyl-4-(2-hydroxyethoxy)-6-indolyl group, a 1,4-dimethoxy-6-indolyl group, a 1,4-diethoxy-6-indolyl group, a 1-cyclopropyl-4-methoxy-6-indolyl group, a 1-cyclopropyl-4-ethoxy-6-indolyl group, a 1-cyclopropyl-4-(2-hydroxyethoxy)-6-indolyl group, a 3-chloro-1-cyclopropyl-4-methoxy-6-indolyl group, a 3-chloro-1-cyclopropyl-4-ethoxy-6-indolyl group, a 1-cyclopropyl-3-methyl-4-methoxy-6-indolyl group, a 1-cyclopropyl-4-ethoxy-3-methyl-6-indolyl group, a 1-ethyl-3-methyl-1H-thieno[2,3-c]pyrazol-5-yl group, a 4-acetyl-7-methoxybenzo[b]furan-2-yl group, a 3-ethyl-7-methoxybenzimidazol-5-yl group, a 3-cyclopropyl-7-ethoxy-1,2-benzisoxazol-5-yl group, a 3-cyclopropyl-8-methoxyimidazo[1,2-a]pyridin-6-yl group; even more preferably a 1-cyclopropyl-4-methoxy-6-indolyl group or a 1-cyclopropyl-3-methyl-4-methoxy-6-indolyl group.

$R^1$ and $R^2$ each independently represent a hydrogen atom, a halogen atom, a cyano group, a C2-C6 alkenyl group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group, or a group of -$Q^1$-N($R^a$)-$Q^2$-$R^b$; a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;
an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a C1-C6 alkyl group or a C2-C6 alkenyl group having the aryl or heterocyclic group.

The halogen atom for $R^1$ and $R^2$ is, for example, preferably a chlorine atom, a bromine atom.
The C2-C6 alkenyl group for $R^1$ and $R^2$ is, for example, preferably a 2-propenyl group, an isopropenyl group.
The C1-C6 alkoxy group for $R^1$ and $R^2$ is, for example, preferably a methoxy group, an ethoxy group, a propoxy group.
The halo-C1-C6 alkoxy group for $R^1$ and $R^2$ is, for example, preferably a fluoromethoxy group, a difluoromethoxy group.
The cyclo-C3-C6 alkyloxy group for $R^1$ and $R^2$ is, for example, preferably a cyclopropyloxy group.
The C2-C7 alkanoyl group for $R^1$ and $R^2$ is, for example, preferably an acetyl group, a propionyl group.
The halo-C2-C7 alkanoyl group for $R^1$ and $R^2$ is, for example, preferably a fluoroacetyl group, a 3-fluoropropionyl group.
The C2-C7 alkoxycarbonyl group for $R^1$ and $R^2$ is, for example, preferably a methoxycarbonyl group, an ethoxycarbonyl group.
The halo-C2-C7 alkoxycarbonyl group for $R^1$ and $R^2$ is, for example, preferably a fluoromethoxycarbonyl group, a difluoromethoxycarbonyl group.
The cyclo-C3-C6 alkyloxycarbonyl group for $R^1$ and $R^2$ is, for example, preferably a cyclopropyloxycarbonyl group.
The aralkyloxycarbonyl group for $R^1$ and $R^2$ is, for example, preferably a benzyloxycarbonyl group.
The carbamoyl-C1-C6 alkoxy group for $R^1$ and $R^2$ is, for example, preferably a carbamoylmethoxy group, a 2-carbamoylethoxy group.
The carboxy-C2-C6 alkenyl group for $R^1$ and $R^2$ is, for example, preferably a 2-carboxyvinyl group, a 3-carboxy-1-propenyl group, a 3-carboxy-2-propenyl group.
In the group of -$Q^1$-N($R^a$)-$Q^2$-$R^b$ for $R^1$ and $R^2$, $Q^1$ and $Q^2$ each independently represent a single bond, or a group of —CO—, —SO$_2$— or —C($R^g$)($R^h$)—; $R^a$ and $R^b$ each independently represent a hydrogen atom, a C2-C6 alkenyl group, a C1-C6 alkoxy group, a cyclo-C3-C6 alkyloxy group, a halo-C1-C6 alkoxy group, a cyclo-C3-C6 alkyl group, an aralkyloxy group, a carbamoyl group, a C2-C7 alkoxycarbonyl group, or a group of —N($R^i$)$R^j$;
a C1-C6 alkyl group optionally having a substituent selected from a group consisting of a halogen atom, a C1-C6 alkoxy group, a carbamoyl group and a C2-C7 alkoxycarbonyl group; or
a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group.
In the group of —C($R^g$)($R^h$)— for $Q^1$ and $Q^2$, $R^g$ and $R^h$ each independently represent a hydrogen atom, a C1-C6 alkyl group, or a halo-C1-C6 alkyl group.
$R^g$ and $R^h$ are, for example, preferably a hydrogen atom, a methyl group, an ethyl group.
$Q^1$ is, for example, preferably a single bond, or a group of —CO— or —C($R^g$)($R^h$)—; and $Q^2$ is, for example, preferably a single bond, or a group of —CO— or —C($R^g$)($R^h$)—.
The group of —C($R^g$)($R^h$)— for $Q^1$ is more preferably —C(CH$_3$)$_2$—; and the group of —C($R^g$)($R^h$)— for $Q^2$ is more preferably —CH$_2$—.
The C2-C6 alkenyl group for $R^a$ and $R^b$ is, for example, preferably a vinyl group, a 2-propenyl group.
The C1-C6 alkoxy group for $R^a$ and $R^b$ is, for example, preferably a methoxy group, an ethoxy group.
The cyclo-C3-C6 alkyloxy group for $R^a$ and $R^b$ is, for example, preferably a cyclopropyloxy group.

The halo-C1-C6 alkoxy group for $R^a$ and $R^b$ is, for example, preferably a fluoromethoxy group, a difluoromethoxy group, a trifluoromethoxy group, a chloromethoxy group, a dichloromethoxy group.

The cyclo-C3-C6 alkyl group for $R^a$ and $R^b$ is, for example, preferably a cyclopropyl group.

The aralkyloxy group for $R^a$ and $R^b$ is, for example, preferably a benzyloxy group.

The C2-C7 alkoxycarbonyl group for $R^a$ and $R^b$ is, for example, preferably a methoxycarbonyl group, an ethoxycarbonyl group, a tert-butoxycarbonyl group.

In the group of —N($R^i$)$R^j$ for $R^a$ and $R^b$, $R^i$ and $R^j$ each independently represent a hydrogen atom, a C1-C6 alkyl group or a halo-C1-C6 alkyl group.

$R^i$ and $R^j$ are, for example, preferably a hydrogen atom, a methyl group or a 2,2,2-trifluoroethyl group.

The group of —N($R^i$)$R^j$ for $R^a$ and $R^b$ is, for example, preferably an amino group, a dimethylamino group, or a 2,2,2-trifluoroethylamino group.

"C1-C6 alkyl group optionally having a substituent selected from a group consisting of a halogen atom, a C1-C6 alkoxy group, a carbamoyl group and a C2-C7 alkoxycarbonyl group" for $R^a$ and $R^b$ means the above-mentioned unsubstituted C1-C6 alkyl group, or the above-mentioned C1-C6 alkyl group having a substituent at any substitutable position thereof, in which the substituent may be the same or different, one or two or more, preferably from 1 to 3 substituents selected from a group consisting of a halogen atom, a C1-C6 alkoxy group, a carbamoyl group and a C2-C7 alkoxycarbonyl group.

The halogen atom for the substituent is, for example, preferably a fluorine atom, a chlorine atom.

The C1-C6 alkoxy group for the substituent is, for example, preferably a methoxy group, an ethoxy group.

The C2-C7 alkoxycarbonyl group for the substituent is, for example, preferably a methoxycarbonyl group, an ethoxycarbonyl group, a tert-butoxycarbonyl group.

The substituent is, for example, preferably a halogen atom, a carbamoyl group, a C2-C7 alkoxycarbonyl group.

"C1-C6 alkyl group" itself of the above-mentioned, optionally-substituted C1-C6 alkyl group for $R^a$ and $R^b$ is, for example, preferably a methyl group, an ethyl group, a propyl group, an isopropyl group.

The above-mentioned, optionally-substituted C1-C6 alkyl group for $R^a$ and $R^b$ is, for example, preferably a methyl group, a difluoromethyl group, a trifluoromethyl group, a methoxymethyl group, a carbamoylmethyl group, a tert-butoxycarbonylmethyl group, an ethyl group, a propyl group, an isopropyl group.

"Heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group" for $R^a$ and $R^b$ means the above-mentioned, unsubstituted heteroaromatic group, or the above-mentioned heteroaromatic group having "a C1-C6 alkyl group optionally having a substituent selected from a group consisting of a halogen atom, a C1-C6 alkoxy group, a carbamoyl group and a C2-C7 alkoxycarbonyl group" as a substituent at any substitutable position thereof, in which the substituent on the heteroaromatic group may be the same or different, one or two or more, preferably one or two selected from them.

Preferred examples of the substituent on the heteroaromatic group, "C1-C6 alkyl group optionally having a substituent selected from a group consisting of a halogen atom, a C1-C6 alkoxy group, a carbamoyl group and a C2-C7 alkoxycarbonyl group" may be the same as those mentioned hereinabove for the "optionally-substituted C1-C6 alkyl group" for $R^a$ and $R^b$.

"Heteroaromatic group" itself of the heteroaromatic group optionally substituted with the above-mentioned, optionally-substituted C1-C6 alkyl group for $R^a$ and $R^b$ is, for example, preferably a pyrrolyl group, a pyrazolyl group, an isoxazolyl group, a 1,2,4-triazolyl group, a pyrimidinyl group.

The heteroaromatic group optionally substituted with the above-mentioned, optionally-substituted C1-C6 alkyl group for $R^a$ and $R^b$ is, for example, preferably a 2-pyrrolyl group, a 1-methyl-2-pyrrolyl group, a 3-pyrazolyl group, a 1-methyl-3-pyrazolyl group, a 2-methyl-3-pyrazolyl group, a 2,5-dimethyl-3-pyrazolyl group, a 2-ethyl-3-pyrazolyl group, a 2-methoxymethyl-3-pyrazolyl group, a 5-methyl-3-isoxazolyl group, a 1,2,4-triazol-3-yl group, a 1-methyl-1,2,4-triazol-3-yl group, a 2-methyl-1,2,4-triazol-3-yl group, a 2-pyrimidinyl group, a 5-pyrimidinyl group.

$R^a$ and $R^b$ are, for example, preferably a hydrogen atom, a C1-C6 alkoxy group, an aralkyloxy group, a carbamoyl group, a C2-C7 alkoxycarbonyl group, a group of —N($R^i$)$R^j$, a C1-C6 alkyl group optionally having the above-mentioned substituent, or a heteroaromatic group optionally substituted with the above-mentioned, optionally-substituted C1-C6 alkyl group.

The group of -$Q^1$-N($R^a$)-$Q^2$-$R^b$ of $R^1$ and $R^2$ is, for example, preferably such that $Q^1$ and $Q^2$ are a single bond, $R^a$ is a hydrogen atom, and $R^b$ is a heteroaromatic group optionally substituted with a C1-C6 alkyl group optionally having a substituent selected from a group consisting of a halogen atom, a C1-C6 alkoxy group, a carbamoyl group and a C2-C7 alkoxycarbonyl group; more preferably, it is a 2-methyl-3-pyrazolylamino group;

such that $Q^1$ is a group of —CO—, $Q^2$ is a group of —C($R^g$)($R^h$)—, $R^a$ is a hydrogen atom, and $R^b$ is a carbamoyl group; more preferably, it is a (carbamoylmethyl)carbamoyl group; or such that $Q^1$ is a group of —CO—, $Q^2$ is a group of —C($R^g$)($R^h$)—, $R^a$ is a hydrogen atom, and $R^b$ is a C1-C6 alkyl group optionally having a substituent selected from a group consisting of a halogen atom, a C1-C6 alkoxy group, a carbamoyl group and a C2-C7 alkoxycarbonyl group.

Examples of the group of -$Q^1$-N($R^a$)-$Q^2$-$R^b$ for $R^1$ and $R^2$ include, for example, an isopropylamino group, a formylamino group, an acetylamino group, a methoxycarbonylamino group, a benzyloxycarbonylamino group, a carbamoylamino group, a 2,2,2-trifluoroethylcarbamoylamino group, a 2-pyrrolylcarbonylamino group, a 1-methyl-2-pyrrolylcarbonylamino group, a 3-pyrazolylamino group, a 1-methyl-3-pyrazolylamino group, a 2-methyl-3-pyrazolylamino group, a 2,5-dimethyl-3-pyrazolylamino group, a 2-ethyl-3-pyrazolylamino group, a 2-methoxymethyl-3-pyrazolylamino group, an N-methyl-N-(2-methyl-3-pyrazolyl)amino group, a 5-methyl-3-isoxazolylamino group, a 1,2,4-triazol-3-ylamino group, a 1-methyl-1,2,4-triazol-3-ylamino group, a 2-methyl-1,2,4-triazol-3-ylamino group, a 2-pyrimidinylamino group, a 5-pyrimidinylamino group, a carbamoyl group, a methylcarbamoyl group, a 2,2-difluoroethylcarbamoyl group, a 2,2,2-trifluoroethylcarbamoyl group, a (carbamoylmethyl)carbamoyl group, a (2-carbamoylethyl)carbamoyl group, a (1-carbamoyl-1-methylethyl)carbamoyl group, a (1-tert-butoxycarbonyl-1-methylethyl)carbamoyl group, a (2-tert-butoxycarbonylethyl)carbamoyl group, an aminosulfonyl group, a methylaminosulfonyl group, a dimethylaminosulfonyl group, an ethylaminosulfonyl group, a propylaminosulfonyl group, a butylaminosulfonyl group, an N-acetyl-N-methylaminosulfonyl group, an N-acetyl-N-ethylaminosulfonyl group, an N-acetyl-N-propylaminosulfonyl group, a 1-amino-1-methylethyl group, a 1-acetylamino-1-methylethyl group, a 1-(benzyloxycarbonylamino)-1-methylethyl group. Of those, for example, preferred are a 1-methyl-3-pyrazolylamino group, a 2-methyl-3-pyrazolylamino group, a 2,5-dimethyl-3-pyrazolylamino group, a 5-methyl-3-isoxazolylamino group, a carbamoyl group, a 2,2,2-trifluoroethylcarbamoyl group, a (carbamoylmethyl)carbamoyl group; more preferred are a 2-methyl-3-pyrazolylamino group, a (carbamoylmethyl)carbamoyl group.

"C1-C6 alkyl group optionally having a substituent selected from a group of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group" for $R^1$ and $R^2$ means the above-mentioned, unsubstituted C1-C6 alkyl group, or the above-mentioned C1-C6 alkyl group having the substituent at any substitutable position thereof, in which the substituent may be the same or different, one or two or more, preferably from 1 to 3 groups selected from a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group.

The halogen atom for the substituent is, for example, preferably a fluorine atom, a chlorine atom.

The C1-C6 alkoxy group for the substituent is, for example, preferably a methoxy group, an ethoxy group.

The halo-C1-C6 alkoxy group for the substituent is, for example, preferably a difluoromethoxy group.

The C1-C6 alkylthio group for the substituent is, for example, preferably a methylthio group, an ethylthio group.

The C2-C7 alkanoyloxy group for the substituent is, for example, preferably an acetyloxy group, a propionyloxy group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group, an ethylsulfonyl group.

The substituent is, for example, preferably a halogen atom, a hydroxyl group, a carboxyl group, a carbamoyl group, a C2-C7 alkoxycarbonyl group.

"C1-C6 alkyl group" itself of the above-mentioned, optionally-substituted C1-C6 alkyl group for $R^1$ and $R^2$ is, for example, preferably a methyl group, an ethyl group, a propyl group, an isopropyl group, a tert-butyl group.

The above-mentioned, optionally-substituted C1-C6 alkyl group for $R^1$ and $R^2$ is, for example, preferably a methyl group, a fluoromethyl group, a hydroxymethyl group, an azidomethyl group, a methoxymethyl group, a methylthiomethyl group, an acetyloxymethyl group, a methoxycarbonylmethyl group, a methylsulfonylmethyl group, an ethyl group, a 1-hydroxyethyl group, a 1-carboxy-1-methylethyl group, a 1-carbamoyl-1-methylethyl group, a 1-methoxycarbonyl-1-methylethyl group, a propyl group, an isopropyl group, a tert-butyl group.

"Aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$" for $R^1$ and $R^2$ means the above-mentioned unsubstituted aryl or heterocyclic group, or the above-mentioned aryl or heterocyclic group having the substituent at any substitutable position thereof, in which the substituent may be the same or different, one or two or more, preferably one or two groups selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$.

The halogen atom for the substituent is, for example, preferably a fluorine atom, a chlorine atom.

The C1-C6 alkyl for the substituent is, for example, preferably a methyl group, an ethyl group.

The halo-C1-C6 alkyl group for the substituent is, for example, preferably a fluoromethyl group, a difluoromethyl group, a trifluoromethyl group.

The hydroxy-C1-C6 alkyl group for the substituent is, for example, preferably a hydroxymethyl group, a 1-hydroxyethyl group, a 2-hydroxyethyl group.

The C2-C7 alkanoyloxy-C1-C6 alkyl group for the substituent is, for example, preferably an acetyloxymethyl group, a pivaloyloxymethyl group.

The C1-C6 alkoxy group for the substituent is, for example, preferably a methoxy group, an ethoxy group.

The halo-C1-C6 alkoxy group for the substituent is, for example, preferably a difluoromethoxy group.

The C2-C7 alkanoyl group for the substituent is, for example, preferably an acetyl group, a propionyl group.

The C2-C7 alkoxycarbonyl group for the substituent is, for example, preferably a methoxycarbonyl group, an ethoxycarbonyl group.

The C1-C6 alkylsulfonyl group for the substituent is, for example, preferably a methylsulfonyl group.

In the group of —CO—N($R^c$)$R^d$ for the substituent, $R^c$ and $R^d$ each independently represent a hydrogen atom, a C1-C6 alkyl group or a halo-C1-C6 alkyl group.

The C1-C6 alkyl group for $R^c$ and $R^d$ is, for example, preferably a methyl group, an ethyl group.

The group of —CO—N($R^c$)$R^d$ for the substituent is, for example, preferably a carbamoyl group, a dimethylcarbamoyl group.

The substituent is, for example, preferably an oxo group, a C1-C6 alkyl group, a formyl group, a carboxyl group, a C2-C7 alkoxycarbonyl group, a C1-C6 alkylsulfonyl group, a group of —CO—N($R^c$)$R^d$.

"Aryl group" itself of the above-mentioned optionally-substituted aryl or heterocyclic group for $R^1$ and $R^2$ is, for example, preferably a phenyl group; "heterocyclic group" itself thereof is, for example, preferably a pyrrolyl group, an imidazolyl group, a pyrazolyl group, a 1,2,4-triazolyl group, a tetrazolyl group, a pyridyl group, a pyrimidinyl group, a pyrrolidinyl group, a dihydro-1,2,4-triazolyl group, a dihydro-1,2,4-oxadiazolyl group, a dihydro-1,3,4-oxadiazolyl group, a dihydro-1,2,4-thiadiazolyl group, a dihydro-1,2,3,5-oxathiadiazolyl group, a dihydropyridyl group, a piperidyl group, a piperazinyl group, a morpholinyl group, a thiomorpholinyl group. Of those, more preferred are a pyrazolyl group, a 1,2,4-triazolyl group, a tetrazolyl group, a pyridyl group, a dihydro-1,2,4-triazolyl group, a dihydro-1,2,4-oxadiazolyl group; even more preferred are a phenyl group, a tetrazolyl group, a pyridyl group, a dihydro-1,2,4-oxadiazolyl group; still more preferred are a tetrazolyl group, a pyridyl group.

The above-mentioned, optionally-substituted aryl or heterocyclic group for $R^1$ and $R^2$ is, for example, preferably a phenyl group optionally substituted with a carboxyl group, a C2-C7 alkoxycarbonyl group or a group of —CO—N($R^c$)$R^d$; a pyrazolyl group optionally substituted with a C1-C6 alkyl group; a 1,2,4-triazolyl group; a tetrazolyl group optionally substituted with a C2-C7 alkanoyloxy-C1-C6 alkyl group; a pyridyl group optionally substituted with a halogen atom, a C1-C6 alkyl group, a C1-C6 alkoxy group, a carboxyl group, a C2-C7 alkoxycarbonyl group or a group of —CO—N($R^c$)$R^d$; a pyrimidinyl group; a dihydro-1,2,4-triazolyl group optionally substituted with an oxo group; a dihydro-1,2,4-oxadiazolyl group optionally substituted with an oxo group; or a dihydropyridyl group optionally substituted with an oxo group. Above all, more preferred are a phenyl group optionally substituted with a carboxyl group or a group of —CO—N($R^c$)$R^d$; a pyrazolyl group optionally substituted with a C1-C6 alkyl group; a 1,2,4-triazolyl group; a tetrazolyl group optionally substituted with a C2-C7 alkanoyloxy-C1-C6 alkyl group; a pyridyl group optionally substituted with a C1-C6 alkoxy group, a carboxyl group or a group of —CO—N($R^c$)$R^d$; a dihydro-1,2,4-triazolyl group optionally substituted with an oxo group; or a dihydro-1,2,4-oxadiazolyl group optionally substituted with an oxo group; even more preferred are a phenyl group optionally substituted with a carboxyl group or a group of —CO—N($R^c$)$R^d$; a tetrazolyl group optionally substituted with a C2-C7 alkanoyloxy-C1-C6 alkyl group; a pyridyl group optionally substituted with a C1-C6 alkoxy group, a carboxyl group or a group of —CO—N($R^c$)$R^d$; or a dihydro-1,2,4-oxadiazolyl group optionally substituted with an oxo group; still more preferred are a tetrazolyl group optionally substituted with a C2-C7 alkanoyloxy-C1-C6 alkyl group; or a pyridyl group optionally substituted with a C1-C6 alkoxy group, a carboxyl group or a group of —CO—N($R^c$)$R^d$, especially a pyridyl group substituted with a carboxyl group.

Examples of the aryl group or the heterocyclic group for $R^1$ and $R^2$ include, for example, a phenyl group, a 3-carboxyphenyl group, a 3-carbamoylphenyl group, a 4-carbamoylphenyl group, a 3-methoxycarbonylphenyl group, a 1-pyrrolyl group, a 1-imidazolyl group, a 3-pyrazolyl group, a 4-pyrazolyl group, a 1-methyl-4-pyrazolyl group, a 1,2,4-triazol-3-yl group, a 1,2,4-triazol-4-yl group, a 5-carbamoyl-1,2,4-triazol-3-yl group, a 1-tetrazolyl group, a 5-tetrazolyl group, a 1-methyl-5-tetrazolyl group, a 2-methyl-5-tetrazolyl group, a 2-pivaloyloxymethyl-5-tetrazolyl group, a 2-dimethylcarbamoyl-5-tetrazolyl group, a 2-pyridyl group, a 4-carboxy-2-pyridyl group, a 5-carboxy-2-pyridyl group, a 3-pyridyl group, a 5-bromo-3-pyridyl group, a 6-methoxy-3-pyridyl group, a 5-carboxy-3-pyridyl group, a 5-carboxy-6-methyl-3-pyridyl group, a 6-carboxy-3-pyridyl group, a 5-carbamoyl-2-pyridyl group, a 5-carbamoyl-3-pyridyl group, a 5-methoxycarbonyl-3-pyridyl group, a 4-pyridyl group, a 2-carboxy-4-pyridyl group, a 2-pyrimidinyl group, a 5-pyrimidinyl group, a 2-oxo-1-pyrrolidinyl group, a 5-oxo-4,5-dihydro-1,2,4-triazol-3-yl group, a 3-oxo-2,3-dihydro-1,2,4-triazol-4-yl group, a 5-oxo-4,5-dihydro-1,2,4-oxadiazol-3-yl group, a 5-thioxo-4,5-dihydro-1,2,4-oxadiazol-3-yl group, a 5-oxo-4,5-dihydro-1,3,4-oxadiazol-2-yl group, a 5-oxo-4,5-dihydro-1,2,4-thiadiazol-3-yl group, a 2-oxo-2,3-dihydro-1,2,3,5-oxathiadiazol-4-yl group, a 6-oxo-1,6-dihydro-3-pyridyl group, a 1-piperidyl group, a 4-oxo-1-piperidyl group, a 1-piperazinyl group, a 3-oxo-1-piperazinyl group, a 4-methyl-1-piperazinyl group, a 4-formyl-1-piperazinyl group, a 4-acetyl-1-piperazinyl group, a 4-methoxycarbonyl-1-piperazinyl group, a 4-carbamoyl-1-piperazinyl group, a 4-methylsulfonyl-1-piperazinyl group, a 4-morpholinyl group, a 1,1-dioxo-4-thiomorpholinyl group. Of those, preferred are a 3-carboxyphenyl group, a 4-pyrazolyl group, a 5-carbamoyl-1,2,4-triazol-3-yl group, a 5-tetrazolyl group, a 4-carboxy-2-pyridyl group, a 5-carboxy-3-pyridyl group, a 5-carboxy-6-methyl-3-pyridyl group, a 6-carboxy-3-pyridyl group, a 2-carboxy-4-pyridyl group, a 5-oxo-4,5-dihydro-1,2,4-triazol-3-yl group, a 5-oxo-4,5-dihydro-1,2,4-oxadiazol-3-yl group; more preferred are a 3-carboxyphenyl group, a 5-tetrazolyl group, a 4-carboxy-2-pyridyl group, a 5-carboxy-3-pyridyl group, a 6-carboxy-3-pyridyl group, a 2-carboxy-4-pyridyl group, a 5-oxo-4,5-dihydro-1,2,4-oxadiazol-3-yl group; even more preferred are a 5-tetrazolyl group, a 5-carboxy-3-pyridyl group.

"C1-C6 alkyl or C2-C6 alkenyl group having the aryl or heterocyclic group" for $R^1$ and $R^2$ means a C1-C6 alkyl or C2-C6 alkenyl group having the same or different, one or two or more, preferably one aryl or heterocyclic group selected from the above-mentioned "aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^{d"}$, and is, for example, preferably a 5-tetrazolylmethyl group, a 2-(5-tetrazolyl)ethyl group, a 2-(5-tetrazolyl)vinyl group, a 3-(5-tetrazolyl)-1-propenyl group.

Preferred embodiments of $R^1$ and $R^2$ are, for example, such that $R^1$ is a hydrogen atom, a halogen atom, a cyano group, a C2-C6 alkenyl group, a C1-C6 alkoxy group, a halo-C1-C6 alkoxy group, a cyclo-C3-C6 alkyloxy group, a C2-C7 alkanoyl group, a halo-C2-C7 alkanoyl group, a C2-C7 alkoxycarbonyl group, a halo-C2-C7 alkoxycarbonyl group, a cyclo-C3-C6 alkyloxycarbonyl group, an aralkyloxycarbonyl group, a carbamoyl-C1-C6 alkoxy group, a carboxy-C2-C6 alkenyl group or a group of -$Q^1$-N($R^a$)-$Q^2$-$R^b$;
a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group;
an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; a C1-C6 alkyl group or a C2-C6 alkenyl group having the aryl or heterocyclic group;
and $R^2$ is a hydrogen atom, a halogen atom, a C1-C6 alkyl group or a C1-C6 alkoxy group.

$R^1$ is, for example, preferably a group of -$Q^1$-N($R^a$)-$Q^2$-$R^b$; a C1-C6 alkyl group optionally having a substituent selected from a group consisting of a halogen atom, a hydroxyl group, an azido group, a C1-C6 alkoxy group, a halo-C1-C6 alkoxy group, a C1-C6 alkylthio group, a C2-C7 alkanoyloxy group, a carboxyl group, a carbamoyl group, a C2-C7 alkoxycarbonyl group and a C1-C6 alkylsulfonyl group; or an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$, especially a pyridyl group substituted with a carboxyl group.

T and U each independently represent a nitrogen atom or a methine group. In case where T or U is a methine group, the methine group may be substituted with $R^1$ or $R^2$.

T and U are preferably a methine group.

V represents an oxygen atom or a sulfur atom, and is preferably an oxygen atom.

In the compounds of formula (I), $R^1$ and $R^2$ may be positioned at any substitutable position of the skeleton of the following formula:

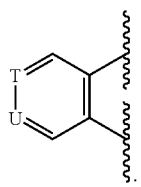

Preferred embodiments of the compounds of formula (I) are, for example, compounds of a general formula (I-1):

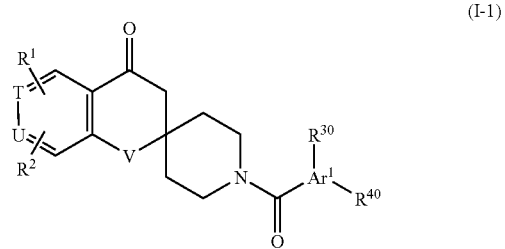

(I-1)

wherein $R^{30}$ and $R^{40}$ each independently represent a halogen atom, a nitro group, a cyclo-C3-C6 alkyl group, a carbamoyl group optionally substituted with a C1-C6 alkyl or cyclo-C3-C6 alkyl group, or a group of —N($R^e$)$R^f$;

a C2-C7 alkanoyl group, a C1-C6 alkoxy group, a C2-C7 alkoxycarbonyl group, a cyclo-C3-C6 alkyloxycarbonyl group, a C1-C6 alkylsulfonyl group, a C1-C6 alkylthio group, a cyclo-C3-C6 alkyloxy group, a cyclo-C3-C6 alkyl-C1-C6 alkoxy group, a cyclo-C3-C6 alkylsulfonyl group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxycarbonyl group, the cyclo-C3-C6 alkyloxy group, the cyclo-C3-C6 alkyl-C1-C6 alkoxy group, the cyclo-C3-C6 alkylsulfonyl group, the cyclo-C3-C6 alkylthio group or the cyclo-C3-C6 alkyl-C1-C6 alkylthio group may be interrupted by an oxygen atom, a sulfur atom or an imino group; or a C1-C6 alkyl group optionally having a substituent selected from a group consisting of a halogen atom, a hydroxyl group and a cyclo-C3-C6 alkyl group; $Ar^1$, $R^1$, $R^3$, $R^e$, $R^f$, T, U and V have the same meanings as above; or compounds of a general formula (I-2):

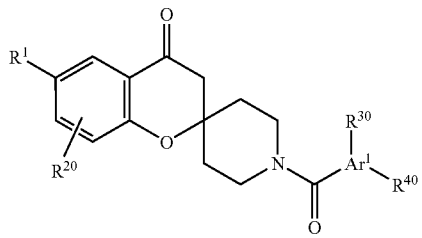

(I-2)

wherein $R^{20}$ represents a hydrogen atom, a halogen atom, a C1-C6 alkyl group or a C1-C6 alkoxy group; and $Ar^1$, $R^1$, $R^{30}$ and $R^{40}$ have the same meanings as above.

In formula (I-1), preferred embodiments of $Ar^1$ and $R^1$ are the same as those of $Ar^1$ and $R^1$ in formula (I). $R^{30}$ and $R^{40}$ correspond to $R^3$ and $R^4$, respectively in formula (I); but $R^{30}$ and $R^{40}$ are not a hydrogen atom. Preferred embodiments of $R^{30}$ and $R^{40}$ are the same as those of $R^3$ and $R^4$.

In formula (I-2), preferred embodiments of $Ar^1$ and $R^1$ are the same as those of $Ar^1$ and $R^1$ in formula (I). $R^{20}$ is preferably a hydrogen atom. $R^{30}$ and $R^{40}$ correspond to $R^3$ and $R^4$, respectively in formula (I); but $R^{30}$ and $R^{40}$ are not a hydrogen atom. Preferred embodiments of $R^{30}$ and $R^{40}$ are the same as those of $R^3$ and $R^4$.

"A substitutable position" and "a bondable position" mean a position of a group at which the group has a chemically-substitutable hydrogen atom on the carbon atom, the nitrogen atom, the oxygen atom and/or the sulfur atom thereof, and the substitution gives a chemically-stable compound; or mean that a chemical bond gives a chemically-stable compound not resulting from the substitution of the type.

Depending on the type of the substituents therein and on the form of their salts, the compounds of the invention include stereoisomers and tautomers such as optical isomers, diastereoisomers and geometrical isomers, and the compounds of the invention encompass all these stereoisomers and tautomers and their mixtures.

The invention encompasses various crystals, amorphous phases, salts, hydrates and solvates of the compounds of the invention.

Further, prodrugs of the compounds of the invention are also within the scope of the invention. In general, such prodrugs are functional derivatives of the compounds of the invention, and they can be readily converted into the compounds that are needed in bodies. Accordingly, the term "administer" as referred to herein for the method of treating various disorders includes not only the administration of a specific compound but also the administration of a compound which, after administered to patients, may be converted into the specific compound in bodies. General methods for selection and production of suitable prodrug derivatives are described, for example, in *Design of Prodrugs*, ed. H. Bundgaard, Elsevier, 1985; *Hydrolysis in Drug and Prodrug Metabolism, Chemistry, Biochemistry and Enzymology*, B. Testa and J. M. Mayer, Wiley-VCH, 2003; and their entire descriptions are referred to and incorporated herein as a part of the specification of the present application. Metabolites of these compounds include active compounds that are produced by leaving the compounds of the invention in a biological environment, and they are within a scope of the invention. Specific examples of the compounds of formula (I), and their salts and esters are, for example, as follows:

(1)  1-[(1-Ethyl-4-methoxy-1H-benzimidazol-6-yl)carbonyl]-6-(1H-tetrazol-5-yl)spiro[chroman-2,4'-piperidine]-4-one, (2) 1'-[(3-Cyclopropyl-8-methoxyimidazo[1,2-a]pyridin-6-yl)carbonyl]-6-(1H-tetrazol-5-yl)spiro[chroman-2,4'-piperidin]-4-one,
(3) 1'-[(1-Cyclopropyl-4-methoxy-1H-indol-6-yl)carbonyl]-6-(5-oxo-4,5-dihydro-1,2,4-oxadiazol-3-yl)spiro[chroman-2,4'-piperidin]-4-one,
(4) 1'-{[1-Ethyl-4-(2-hydroxyethoxy)-1H-indol-6-yl]carbonyl}-6-(1H-tetrazol-5-yl)spiro[chroman-2,4'-piperidin]-4-one,
(5) Sodium 3-{1'-[(1-cyclopropyl-4-methoxy-1H-indol-6-yl)carbonyl]-4-oxospiro[chroman-2,4'-piperidin]-6-yl}benzoate,
(6) 5-{1'-[(1-Cyclopropyl-4-methoxy-1H-indol-6-yl)carbonyl]-4-oxospiro[chroman-2,4'-piperidin]-6-yl}nicotinic acid,
(7) 5-{1'-[(1-Cyclopropyl-4-methoxy-1H-indol-6-yl)carbonyl]-4-oxo-3,4-dihydrospiro[chroman-2,4'-piperidin]-6-yl}nicotinic acid sodium salt,
(8) 1'-{[1,4-Dimethoxy-1H-indol-6-yl]carbonyl}-6-(1H-tetrazol-5-yl)spiro[chroman-2,4'-piperidin]-4-one,
(9) 1'-{[1,4-Dimethoxy-1H-indol-6-yl]carbonyl}-6-(1H-tetrazol-5-yl)spiro[chroman-2,4'-piperidin]-4-one sodium salt,
(10) 1'-[(1-Ethyl-4-methoxy-1H-indazol-6-yl)carbonyl]-6-(1H-tetrazol-5-yl)spiro[chroman-2,4'-piperidin]-4-one,
(11) 1'-[(1-Cyclopropyl-4-methoxy-1H-indol-6-yl)carbonyl]-6-(1H-tetrazol-5-yl)spiro[chroman-2,4'-piperidin]-4-one,
(12) 1'-[(1-Cyclopropyl-4-methoxy-1H-indol-6-yl)carbonyl]-6-(1H-tetrazol-5-yl)spiro[chroman-2,4'-piperidin]-4-one sodium salt,
(13) 1'-[(1-Cyclopropyl-4-ethoxy-1H-indol-6-yl)carbonyl]-6-(1H-tetrazol-5-yl)spiro[chroman-2,4'-piperidin]-4-one,
(14) 1'-[(1-Cyclopropyl-4-ethoxy-1H-indol-6-yl)carbonyl]-6-(1H-tetrazol-5-yl)spiro[chroman-2,4'-piperidin]-4-one sodium salt,
(15) 1'-[(1,4-Diethoxy-1H-indazol-6-yl)carbonyl]-6-(1H-tetrazol-5-yl)spiro[chroman-2,4'-piperidin]-4-one,
(16) 1'-[(3-Chloro-1-cyclopropyl-4-ethoxy-1H-indol-6-yl)carbonyl]-6-(1H-tetrazol-5-yl)spiro[chroman-2,4'-piperidin]-4-one,
(17) 1'-[(1-Cyclopropyl-4-ethoxy-3-methyl-1H-indol-6-yl)carbonyl]-6-(1H-tetrazol-5-yl)spiro[chroman-2,4'-piperidin]-4-one,
(18) 3-(1'-{[1-Cyclopropyl-4-(2-hydroxyethoxy)-1H-indol-6-yl]carbonyl}-4-oxo-spiro[chroman-2,4'-piperidin]-6-yl)benzoic acid,
(19) 5-{1'-[(1-Cyclopropyl-4-ethoxy-1H-indol-6-yl)carbonyl]-4-oxo-spiro[chroman-2,4'-piperidin]-6-yl}nicotinic acid sodium salt,
(20) 2-{1'-[(1-Cyclopropyl-4-methoxy-1H-indol-6-yl)carbonyl]-4-oxo-spiro[chroman-2,4'-piperidin]-6-yl}isonicotinic acid sodium salt,
(21) 4-{1'-[(1-Cyclopropyl-4-methoxy-1H-indol-6-yl)carbonyl]-4-oxo-spiro[chroman-2,4'-piperidin]-6-yl}pyridine-2-carboxylic acid sodium salt,
(22) 5-{1'-[(1-Cyclopropyl-4-methoxy-1H-indol-6-yl)carbonyl]-4-oxo-spiro[chroman-2,4'-piperidin]-6-yl}pyridine-2-carboxylic acid sodium salt,
(23) 5-{1'-[(1-Cyclopropyl-4-methoxy-3-methyl-1H-indol-6-yl)carbonyl]-4-oxo-spiro[chroman-2,4'-piperidin]-6-yl}nicotinic acid sodium salt,
(24) 5-{1'-[(3-Chloro-1-cyclopropyl-4-methoxy-1H-indol-6-yl)carbonyl]-4-oxo-spiro[chroman-2,4'-piperidin]-6-yl}nicotinic acid sodium salt,
(25) 1'-[(4-Acetyl-7-methoxy-1-benzofuran-2-yl)carbonyl]-6-(1H-tetrazol-5-yl)spiro[chroman-2,4'-piperidin]-4-one,
(26) 1'-[(1-Ethyl-3-methyl-1H-thieno[2,3-c]pyrazol-5-yl)carbonyl]-6-(1H-tetrazol-5-yl)spiro[chroman-2,4'-piperidin]-4-one,
(27) 5-{1'-[(1-Cyclopropyl-4-methoxy-3-methyl-1H-indol-6-yl)carbonyl]-4-oxo-spiro[chroman-2,4'-piperidin]-6-yl}nicotinic acid,
(28) 1'-[(4-Methoxy-1-methyl-1H-pyrazolo[3,4-b]pyridin-6-yl)carbonyl]-6-(1H-tetrazol-5-yl)spiro[chroman-2,4'-piperidin]-4-one,
(29) N-Carbamoylmethyl-1'-[(1-cyclopropyl-4-ethoxy-1H-indol-6-yl)carbonyl]-4-oxo-spiro[chroman-2,4'-piperidine]-6-carboxamide,
(30) 1'-[(3-Chloro-1-cyclopropyl-7-ethoxy-1H-indol-5-yl)carbonyl]-6-(1H-tetrazol-5-yl)spiro[chroman-2,4'-piperidin]-4-one,
(31) 1'-[(3-Cyclopropyl-7-ethoxy-1,2-benzisoxazol-5-yl)carbonyl]-6-(1H-tetrazol-5-yl)spiro[chroman-2,4'-piperidin]-4-one,
(32) 1'-[(2-Cyclopropyl-7-ethoxy-1,3-benzoxazol-5-yl)carbonyl]-6-(1H-tetrazol-5-yl)spiro[chroman-2,4'-piperidin]-4-one,
(33) 1-Cyclopropyl-4-ethoxy-6-{[4-oxo-6-(1H-tetrazol-5-yl)spiro[chroman-2,4'-piperidin]-1'-yl]carbonyl}-1H-indole-3-carboxamide,
(34) N-Carbamoylmethyl-1'-[(1-cyclopropyl-4-ethoxy-3-methyl-1H-indol-6-yl)carbonyl]-4-oxospiro[chroman-2,4'-piperidine]-6-carboxamide,
(35) N-Carbamoylmethyl-1'-[(1,4-diethoxy-1H-indol-6-yl)carbonyl]-4-oxospiro[chroman-2,4'-piperidine]-6-carboxamide,
(36) 1'-{[1-Cyclopropyl-4-(2-hydroxyethoxy)-1H-indol-6-yl]carbonyl}-6-(1H-tetrazol-5-yl)spiro[chroman-2,4'-piperidin]-4-one,
(37) 1-Cyclopropyl-4-ethoxy-N-methyl-6-{[4-oxo-6-(1H-tetrazol-5-yl)spiro[chroman-2,4'-piperidin]-1'-yl]carbonyl}-1H-indole-3-carboxamide,
(38) Methyl 3-(1'-{[3-carbamoyl-1-cyclopropyl-4-ethoxy-1H-indol-6-yl]carbonyl}-4-oxospiro[chroman-2,4'-piperidin]-6-yl)benzoate,
(39) 3-(1'-{[3-Carbamoyl-1-cyclopropyl-4-ethoxy-1H-indol-6-yl]carbonyl}-4-oxospiro[chroman-2,4'-piperidin]-6-yl)benzoic acid,
(40) 1-Cyclopropyl-4-ethoxy-6-{[4-oxo-6-(1H-pyrazol-4-yl)spiro[chroman-2,4'-piperidin]-1'-yl]carbonyl}-1H-indole-3-carboxylic acid,
(41) 1-Cyclopropyl-4-ethoxy-6-({6-[(1-methyl-1H-pyrazol-5-yl)amino]-4-oxospiro[chroman-2,4'-piperidin]-1'-yl}carbonyl)-1H-indole-3-carboxylic acid,
(42) 4-{1'-[(1-Cyclopropyl-4-methoxy-3-methyl-1H-indol-6-yl)carbonyl]-4-oxospiro[chroman-2,4'-piperidin]-6-yl}pyridine-2-carboxylic acid,
(43) 5-{1'-[(1-Cyclopropyl-4-methoxy-3-methyl-1H-indol-6-yl)carbonyl]-4-oxospiro[chroman-2,4'-piperidin]-6-yl}-2-methylnicotinic acid,
(44) 6-{1'-[(1-Cyclopropyl-4-methoxy-3-methyl-1H-indol-6-yl)carbonyl]-4-oxospiro[chroman-2,4'-piperidin]-6-yl}nicotinic acid,
(45) 5-{1'-[(1-Cyclopropyl-4-ethoxy-3-methyl-1H-indol-6-yl)carbonyl]-4-oxospiro[chroman-2,4'-piperidin]-6-yl}nicotinic acid,
(46) 4-{1'-[(1-Cyclopropyl-4-ethoxy-3-methyl-1H-indol-6-yl)carbonyl]-4-oxospiro[chroman-2,4'-piperidin]-6-yl}pyridine-2-carboxylic acid,
(47) 5-{1'-[(1-Cyclopropyl-4-ethoxy-3-methyl-1H-indol-6-yl)carbonyl]-4-oxo-spiro[chroman-2,4'-piperidin]-6-yl}nicotinic acid sodium salt,

(48) 5-{1'-[(1,4-Dimethoxy-3-methyl-1H-indol-6-yl)carbonyl]-4-oxospiro[chroman-2,4'-piperidin]-6-yl}nicotinic acid,
(49) 6-(5-Bromopyridin-3-yl)-1'-[(1-cyclopropyl-4-methoxy-3-methyl-1H-indol-6-yl)carbonyl]spiro[chroman-2,4'-piperidin]-4-one,
(50) Methyl 5-{1'-[(1-cyclopropyl-4-methoxy-3-methyl-1H-indol-6-yl)carbonyl]-4-oxospiro[chroman-2,4'-piperidin]-6-yl}nicotinate,
(51) 1'-[(1-Cyclopropyl-4-methoxy-1H-indol-6-yl)carbonyl]-6-(5-oxo-4,5-dihydro-1H-1,2,4-triazol-3-yl)spiro[chroman-2,4'-piperidin]-4-one,
(52) N-Carbamoylmethyl-1'-[(1-cyclopropyl-4-methoxy-1H-indol-6-yl)carbonyl]-4-oxo-spiro[chroman-2,4'-piperidine]-6-carboxamide,
(53) Sodium 5-{1'-[(1-cyclopropyl-4-ethoxy-3-methyl-1H-indol-6-yl)carbonyl]-4-oxospiro[chroman-2,4'-piperidin]-6-yl}-2-methylnicotinate,
(54) 1'-[(1-Ethyl-4-morpholin-4-yl-1H-indol-6-yl)carbonyl]-6-(1H-tetrazol-5-yl)spiro[chroman-2,4'-piperidin]-4-one,
(55) 1'-[(1-Cyclopropyl-4-methoxy-3-methyl-1H-indol-6-yl)carbonyl]-6-(1H-tetrazol-5-yl)spiro[chroman-2,4'-piperidin]-4-one,
(56) 1'-[(1-Ethyl-4-methoxy-1H-indol-6-yl)carbonyl]-6-(1H-tetrazol-5-yl)spiro[chroman-2,4'-piperidin]-4-one,
(57) 5-{1'-[(1-Cyclopropyl-4-methoxy-1H-indol-6-yl)carbonyl]-4-oxo-spiro[chroman-2,4'-piperidin]-6-yl}-4H-1,2,4-triazole-3-carboxamide,
(58) 1'-[(1,3-Diethyl-7-methoxy-2-oxo-2,3-dihydro-1H-benzimidazol-5-yl)carbonyl]-6-(1H-tetrazol-5-yl)spiro[chroman-2,4'-piperidin]-4-one,
(59) 5-{1'-[(6-Cyclopropyl-1-isopropyl-1H-pyrazolo[3,4-b]pyridin-4-yl)carbonyl]-4-oxo-spiro[chroman-2,4'-piperidin]-6-yl}nicotinic acid, or
(60) 1'-[(1-Cyclopropyl-4-methoxy-1H-benzimidazol-6-yl)carbonyl]-6-(1H-tetrazol-5-yl)spiro[chroman-2,4'-piperidin]-4-one.

In one embodiment of the present invention, the compounds are selected from the group consisting of:

3-{1'-[(1-cyclopropyl-4-methoxy-1H-indol-6-yl)carbonyl]-4-oxospiro[chroman-2,4'-piperidin]-6-yl}benzoic acid, or a salt or ester thereof;
5-{1'-[(1-cyclopropyl-4-methoxy-1H-indol-6-yl)carbonyl]-4-oxospiro[chroman-2,4'-piperidin]-6-yl}nicotinic acid, or a salt or ester thereof;
1'-[(1-cyclopropyl-4-methoxy-1H-indol-6-yl)carbonyl]-6-(1H-tetrazol-5-yl)spiro[chroman-2,4'-piperidin]-4-one, or a salt thereof;
1'-[(1-cyclopropyl-4-ethoxy-3-methyl-1H-indol-6-yl)carbonyl]-6-(1H-tetrazol-5-yl)spiro[chroman-2,4'-piperidin]-4-one, or a salt thereof; or
5-{1'-[(1-cyclopropyl-4-methoxy-3-methyl-1H-indol-6-yl)carbonyl]-4-oxo-spiro[chroman-2,4'-piperidin]-6-yl}nicotinic acid, or a salt or ester thereof.

Methods for producing the compounds of the invention are described below.

The compounds (I) of the invention may be produced according to the production method mentioned below, or according to the methods shown in Examples and Reference Examples given hereinunder. However, the production of the compounds (I) of the invention should not be restricted by these reaction examples.

Production Method

A compound protected with a suitable group (II in the following drawing) is deprotected, and then condensed with an aromatic carboxylic acid or its reactive derivative of a formula (III):

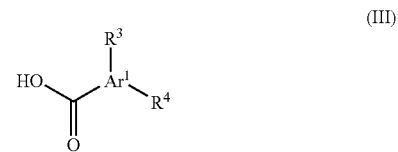

wherein $Ar^1$, $R^3$ and $R^4$ have the same meanings as above, according to a chemical process well known in the field of organic chemistry.

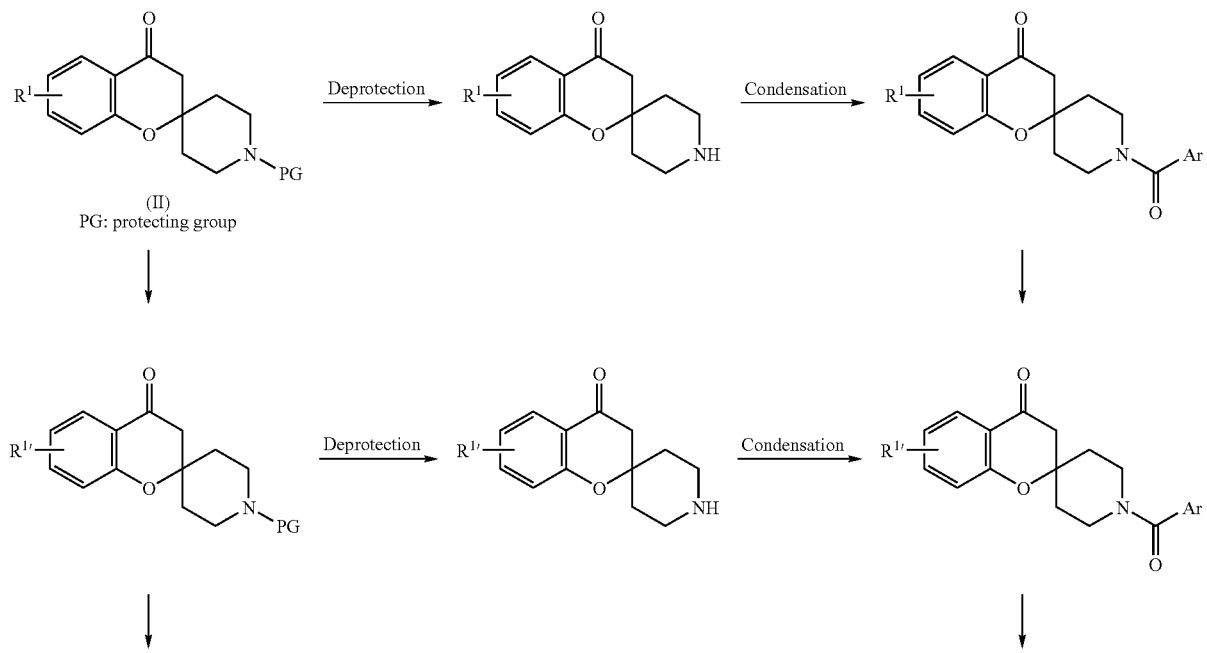

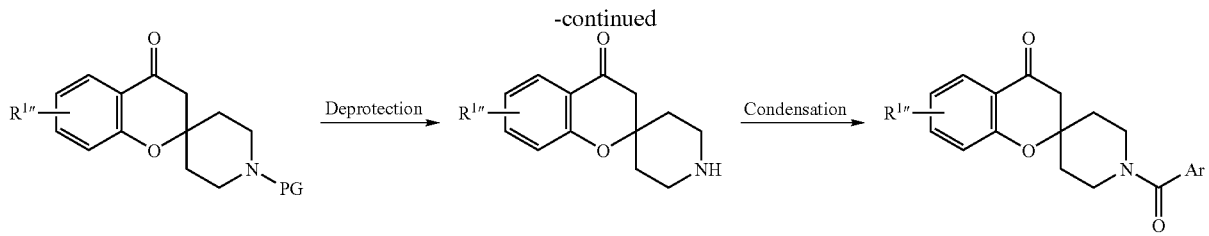

wherein Ar represents a group of the following formula:

and $Ar^1$, $R^3$ and $R^4$ have the same meanings as above.

The protective group (PG) may be, for example, a tert-butoxycarbonyl, benzyloxycarbonyl or benzoyl group, and may also be any other known protective group. For selecting suitable protective groups and their deprotection, for example, referred to is *Protective Groups in Organic Synthesis* (Theodora W. Greene & Peter G. M. Wuts, John Woley & Sons, 1999).

In the above series of reaction, the functional groups such as hydroxyl group, amino group, imino group and carboxyl group which are not concerned with the reaction may be suitably protected, if desired, and they may be deprotected after the reaction.

Not specifically defined, "protective group for hydroxyl group" may be any one having its function and includes, for example, a C1-C6 alkyl group such as a methyl group, an ethyl group, a propyl group, an isopropyl group, a tert-butyl group; a C1-C6 alkylsilyl group such as a trimethylsilyl group, a tert-butyldimethylsilyl group; a C1-C6 alkoxymethyl group such as a methoxymethyl group, a 2-methoxyethoxymethyl group; a tetrahydropyranyl group; a trimethylsilylethoxymethyl group, an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group. Especially preferred are a methyl group, a methoxymethyl group, a tetrahydropyranyl group, a trityl group, a trimethylsilylethoxymethyl group, a tert-butyldimethylsilyl group, an acetyl group.

Also not specifically defined, "protective group for amino group and imino group" may be any one having its function and includes, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group; a C2-C7 alkanoyl group such as a formyl group, an acetyl group, a propionyl group, a butyryl group, a pivaloyl group; a benzoyl group; an arylalkanyl group such as a phenylacetyl group, a phenoxyacetyl group; a C2-C7 alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a C1-C6 alkylsilyl group such as a trimethylsilyl group, a tert-butyldimethylsilyl group; a tetrahydropyranyl group; a trimethylsilylethoxymethyl group; a C1-C6 alkylsulfonyl group such as a methylsulfonyl group, an ethylsulfonyl group; an arylsulfonyl group such as a benzenesulfonyl group, a toluenesulfonyl group. Especially preferred are an acetyl group, a benzoyl group, a tert-butoxycarbonyl group, a benzyloxycarbonyl group, a trimethylsilylethoxymethyl group, a methylsulfonyl group.

Also not specifically defined, "protective group for carboxyl group" may be any one having its function and includes, for example, a C1-C6 alkyl group such as a methyl group, an ethyl group, a propyl group, an isopropyl group, a tert-butyl group; a halo-C1-C6 alkyl group such as a 2,2,2-trichloroethyl group; a C2-C6 alkenyl groups such as a 2-propenyl group; an aralkyl group such as a benzyl group, a p-methoxybenzyl group, a p-nitrobenzyl group, a benzhydryl group, a trityl group. Especially preferred are a methyl group, an ethyl group, a tert-butyl group, a 2-propenyl group, a benzyl group, a p-methoxybenzyl group, a benzhydryl group.

For the introduction and the removal of the protective groups, referred to are the above references.

The substituent $R^1$ may be converted into a group of any other type ($R^{1'}$, $R^{1''}$) in any suitable stage according to a chemical process per-se well known in the field of organic chemistry.

For example, when $R^1$ is a bromide group, then it may be converted into a cyano group and may be further into a tetrazolyl group. The conversion reaction may be attained according to a chemical process well known in the field of organic chemistry.

In the above drawing, the condensation of the amino compound derived from the compound of formula (II), with an aromatic carboxylic acid may be attained in the same manner. In general, from 0.5 mol to an excessive molar amount, preferably from 1 mol to 1.5 mols of an aromatic carboxylic acid is used relative to one mol of the amino compound.

The reaction may be attained generally in an inert solvent. The insert solvent is preferably methylene chloride, chloroform, tetrahydrofuran, dimethylformamide, pyridine or their mixtures.

Preferably, the reaction is effected in the presence of a condensing agent. The condensing agent includes, for example, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris(dimethylamino) phosphonium hexafluorophosphate, benzotriazol-1-yloxy-tris-pyrrolidinophosphonium hexafluorophosphate, bromotris(dimethylamino)phosphonium hexafluorophosphate, diphenylphosphoryl azide, 1,1'-carbonyldiimidazole.

The condensing agent may be used in an amount of from 1 mol to an excessive molar amount, preferably from 1 mol to 1.5 mols relative to 1 mol of the aromatic carboxylic acid.

The reaction temperature may be generally from −50° C. to 100° C., preferably from −20° C. to 50° C.

The reaction time may be generally from 30 minutes to 7 days, preferably from 1 hour to 24 hours.

In place of the aromatic carboxylic acid, a reactive derivative of the carboxylic acid may be reacted with the amino compound to produce the intended product.

The reactive derivative of the aromatic carboxylic acid usable herein includes, for example, acid halides, mixed acid anhydrides, active esters, and active amides.

The acid halide may be prepared by reacting the aromatic carboxylic acid with a halogenating agent in an ordinary manner. The halogenating agent includes, for example, thionyl chloride, phosphorus trichloride, phosphorus pentachloride, phosphorus oxychloride, phosphorus trichloride, oxalyl chloride, phosgene.

The mixed acid anhydride may be prepared by reacting the aromatic carboxylic acid with an alkyl chlorocarbonate such as ethyl chlorocarbonate or with an aliphatic carboxylic acid chloride such as pivaloyl chloride, in an ordinary manner.

The active ester may be prepared by reacting the aromatic carboxylic acid with an N-hydroxy compound such as N-hydroxysuccinimide, N-hydroxyphthalimide, and 1-hydroxybenzotriazole, or with a phenol compound such as 4-nitrophenol, 2,4-dinitrophenol, 2,4,5-trichlorophenol, and pentachlorophenol, in the presence of a condensing agent such as N,N'-dicyclohexylcarbodiimide and 1-(3-dimethylaminopropyl)-3-ethylcarbodiimide, in an ordinary manner.

The active amide may be prepared by reacting the aromatic carboxylic acid with, for example, 1,1'-carbonyldiimidazole or 1,1'-carbonylbis(2-methylimidazole) in an ordinary manner.

The reaction between the amino compound and the reactive derivative of the carboxylic acid may be attained, generally using from 0.5 mols to an excessive molar amount, preferably from 1 mol to 1.5 mols of the reactive derivative of the carboxylic acid, per 1 mol of the amino compound.

The reaction may be effected generally in an inert solvent. The inert solvent is, for example, preferably methylene chloride, chloroform, tetrahydrofuran, dimethylformamide, pyridine and their mixtures.

The reaction may go on in the absence of a base, but for more smoothly promoting it, the reaction is preferably effected in the presence of a base.

The base includes an organic base such as triethylamine, diisopropylethylamine, pyridine, and 4-dimethylaminopyridine; and inorganic base such as sodium hydroxide, potassium hydroxide, sodium carbonate, potassium carbonate and sodium hydrogencarbonate.

In general, the base is used preferably in an amount of from 1 mol to an excessive molar amount relative to 1 mol of the amino compound. When the base is liquid, then the base may serve also as a solvent.

The reaction temperature may be generally from −50° C. to 130° C., preferably from −20° C. to 100° C.

The reaction time may be generally from 5 minutes to 7 days, preferably from 30 minutes to 24 hours.

After the reaction, the system may be processed in an ordinary manner to give a crude product of the intended compound. The thus-obtained compound may be purified in an ordinary manner, or not purified, it may be subjected to the next reaction, if desired.

After the reaction, when the product has a protective group, then the protective group may be removed. When the product does not have a protective group, it may be processed in any ordinary manner, and the intended final product may be thus produced.

The compounds of formula (II) and (D) may be commercial products, or may be prepared according to a known method or according to a method similar to a known method, or with reference to the methods described in Examples and Reference Examples, suitably as combined, if desired.

The compounds of formula (I) may be administered orally or parenterally, and after formulation into preparations suitable for the intended administration route, they can be used as therapeutic agents, for example, for vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy, sexual dysfunction; digestive system diseases such as liver dysfunction, pancreatitis, cholecystitis and gastroesophageal reflux; respiratory diseases such as Pickwickian syndrome and sleep apnea syndrome; infectious diseases caused by bacteria, fungi or parasites; malignant neoplasm; and inflammatory diseases such as arthritis and skin ulcer.

The following "diabetes related disorders" are diseases, disorders and conditions that are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, ACC 1/2 inhibitors may also be useful to treat hypertension associated with this condition.

One aspect of the present invention provides a method for the treatment or prevention of disorders, diseases or conditions responsive to the modulation of ACC-1 or ACC-2 in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of disorders, diseases or conditions responsive to the modulation of ACC-1 or ACC-2 such as, but not limited to, metabolic syndrome, fatty liver, hyperlipemia, dyslipidemia, non-alcoholic fatty liver disease, obesity, diabetes, bulimia, malignant neoplasm or an infectious disease in a subject in need thereof which comprises administering to said subject a therapeutically or prophylactically effective amount of a compound of formula (I), or a pharmaceutically acceptable salt or ester thereof.

Another aspect of the present invention provides a method for the treatment of metabolic syndrome, fatty liver, hyperlipemia, obesity, diabetes, bulimia, malignant neoplasm or infectious diseases, which comprises administering to a subject in need thereof a therapeutically effective amount of the compound or its salt or ester of claim 1.

Another aspect of the present invention provides a method for the treatment and prevention of diabetes in a subject in need thereof which comprises administering to said subject a therapeutically or prophylactically effective amount of a compound of formula (I), or a pharmaceutically acceptable salt or ester thereof.

Another aspect of the present invention provides a method for the treatment and prevention of obesity in a subject in need thereof which comprises administering to said subject a therapeutically or prophylactically effective amount of a compound of formula (I), or a pharmaceutically acceptable salt or ester thereof.

Another aspect of the present invention provides a method for the treatment and prevention of fatty liver in a subject in need thereof which comprises administering to said subject a therapeutically or prophylactically effective amount of a compound of formula (I), or a pharmaceutically acceptable salt or ester thereof.

Another aspect of the present invention provides a method for the treatment or prevention of an obesity-related disorder selected from the group consisting of overeating, binge eating, hypertension, elevated plasma insulin concentrations, insulin resistance, hyperlipidemia, endometrial cancer, breast cancer, prostate cancer, colon cancer, kidney cancer, osteoarthritis, obstructive sleep apnea, heart disease, abnormal heart rhythms and arrythmias, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastro-esophageal reflux, Pickwickian syndrome, inflammation, systemic inflammation of the vasculature, arteriosclerosis, hypercholesterolemia, hyperuricaemia, lower back pain, gallbladder disease, gout, constipation, irritable bowel syndrome, inflammatory bowel syndrome, cardiac hypertrophy, left ventricular hypertrophy, in a subject in need thereof which comprises administering to the subject a therapeutically or prophylactically effective amount of a compound of formula (I), or a pharmaceutically acceptable salt or ester thereof.

Another aspect of the present invention provides a method for the treatment or prevention of hyperlipemia or dyslipidemia in a subject in need thereof which comprises administering to the subject a therapeutically or prophylactically effective amount of a compound of formula (I), or a pharmaceutically acceptable salt or ester thereof.

Another aspect of the present invention provides a method for caloric intake in a subject in need thereof which comprises administering to the subject a therapeutically or prophylactically effective amount of a compound of formula (I), or a pharmaceutically acceptable salt or ester thereof. Another aspect of the present invention provides a method for reducing food intake in a subject in need thereof which comprises administering to the subject a therapeutically or prophylactically effective amount of a compound of formula (I), or a pharmaceutically acceptable salt or ester thereof. Another aspect of the present invention provides a method for increasing satiety in a subject in need thereof which comprises administering to the subject a therapeutically or prophylactically effective amount of a compound of formula (I), or a pharmaceutically acceptable salt or ester thereof. Another aspect of the present invention provides a method for reducing appetite in a subject in need thereof which comprises administering to the subject a therapeutically or prophylactically effective amount of a compound of formula (I), or a pharmaceutically acceptable salt or ester thereof.

The present invention also relates to methods for treating or preventing obesity by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing diabetes by administering a compound of formula (I), or a pharmaceutically acceptable salt or ester thereof, in combination with a therapeutically or prophylactically effective amount of another agent known to be useful to treat or prevent the condition.

The present invention also relates to methods for treating or preventing hyperlipemia or dyslipidemia by administering a compound of formula (I), or a pharmaceutically acceptable salt or ester thereof, in combination with a therapeutically or prophylactically effective amount of another agent known to be useful to treat or prevent the condition.

Another aspect of the present invention provides a pharmaceutical composition comprising a compound of formula (I), or a pharmaceutically acceptable salt or ester thereof, and a pharmaceutically acceptable carrier.

Yet another aspect of the present invention relates to a compound of formula (I), or a pharmaceutically acceptable salt or ester thereof, for use in medicine.

Yet another aspect of the present invention relates to the use of a compound of formula (I), or a pharmaceutically acceptable salt or ester thereof, for the manufacture of a medicament useful for the treatment or prevention, or suppression of a disease mediated by ACC-1 or ACC-2 in a subject in need thereof.

Yet another aspect of the present invention relates to the use of a compound of formula (I), or a pharmaceutically acceptable salt or ester thereof, for the manufacture of a medicament useful for the treatment or prevention of metabolic syndrome, hyperlipemia, dyslipidemia, non-alcoholic fatty liver disease, obesity, diabetes, bulimia, malignant neoplasm or an infectious disease in a subject in need thereof.

Yet another aspect of the present invention relates to the use of a compound of formula (I), or a pharmaceutically acceptable salt or ester thereof, for the manufacture of a medicament useful for the treatment or prevention of obesity in a subject in need thereof.

Yet another aspect of the present invention relates to the use of a compound of formula (I), or a pharmaceutically acceptable salt or ester thereof, for the manufacture of a medicament useful for the treatment or prevention of diabetes in a subject in need thereof.

Yet another aspect of the present invention relates to the use of a compound of formula (I), or a pharmaceutically acceptable salt or ester thereof, for the manufacture of a medicament useful for the treatment or prevention of hyperlipemia or dyslipidemia in a subject in need thereof.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament useful for the treatment, control, or prevention of obesity, diabetes, a diabetes related disorder, or an obesity-related disorder in a subject in need of such treatment.

Yet another aspect of the present invention relates to the use of a therapeutically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagon-like peptide 1 agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof, for the manufacture of a medicament for treatment or prevention of obesity, diabetes, a diabetes related disorder, or an obesity-related disorder which comprises an effective amount of a compound of formula (I), or a pharmaceutically acceptable salt or ester thereof, and an effective amount of the agent, together or separately.

Yet another aspect of the present invention relates to a product containing a therapeutically effective amount of a compound of formula (I), or a pharmaceutically acceptable salt or ester thereof; and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanocortin 4 receptor agonist, a melanin-concentrating hormone receptor antagonist, a bombesin receptor subtype 3 agonist, a ghrelin receptor antagonist, PYY, $PYY_{3-36}$, and a NK-1 antagonist, or a pharmaceutically acceptable salt thereof, as a combined preparation for simultaneous, separate or sequential use in obesity, diabetes, a diabetes related disorder, or an obesity-related disorder.

Yet another aspect of the present invention relates to the use of a therapeutically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, taranabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)-benzonitrile, 3-((4-chlorophenyl) {3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[1-(3,5-difluorophenyl)-2-fluoro-2-methylpropyl]azetidin-1-yl}methyl)thiophene-3-carbonitrile, or a pharmaceutically acceptable salt or ester or prodrug thereof, for the manufacture of a medicament useful for the treatment, control, or prevention of obesity, diabetes, a diabetes related disorder, or an obesity-related disorder in a subject in need of such treatment.

Yet another aspect of the present invention relates to a method of treatment or prevention of disorders, diseases or conditions responsive to the modulation of ACC-1 or ACC-2 in a subject in need thereof which comprises administering to the subject a therapeutically or prophylactically effective amount of a compound of formula (I), or a pharmaceutically acceptable salt or ester thereof, and a therapeutically effective amount of an agent selected from the group consisting of an insulin sensitizer, an insulin mimetic, a sulfonylurea, an α-glucosidase inhibitor, a dipeptidyl peptidase 4 (DPP-4 or DP-IV) inhibitor, a glucagons like peptide 1 (GLP-1) agonist, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a melanocortin 4 receptor agonist, a bombesin receptor subtype 3 agonist, a ghrelin receptor antagonist, PYY, $PYY_{3-36}$, and a NK-1 antagonist, or a pharmaceutically acceptable salt thereof.

Yet another aspect of the present invention relates to a method of treatment or prevention of disorders, diseases or conditions responsive to the modulation of ACC-1 or ACC-2 in a subject in need thereof which comprises administering to the subject a therapeutically or prophylactically effective amount of a compound of formula (I), or a pharmaceutically acceptable salt or ester thereof, and a therapeutically effective amount of at least one agent selected from the group consisting of: simvastatin, mevastatin, ezetimibe, atorvastatin, sitagliptin, metformin, sibutramine, orlistat, Qnexa, topiramate, phentermine, losartan, losartan with hydrochlorothiazide, or a CB1 antagonist/inverse agonist selected from: rimonabant, taranabant, N-[3-(4-chlorophenyl)-2(S)-phenyl-1(S)-methylpropyl]-2-(4-trifluoromethyl-2-pyrimidyloxy)-2-methylpropanamide, N-[(1S,2S)-3-(4-chlorophenyl)-2-(3-cyanophenyl)-1-methylpropyl]-2-methyl-2-{[5-(trifluoromethyl)pyridin-2-yl]oxy}propanamide, N-[3-(4-chlorophenyl)-2-(5-chloro-3-pyridyl)-1-methylpropyl]-2-(5-trifluoromethyl-2-pyridyloxy)-2-methylpropanamide, 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]-azetidin-3-yl}-1-(3,5-difluorophenyl)-2-methylpropan-2-ol, 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)-benzonitrile, 3-((4-chlorophenyl) {3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[1-(3,5-difluorophenyl)-2-fluoro-2-methylpropyl]azetidin-1-yl}methyl)thiophene-3-carbonitrile, or a pharmaceutically acceptable salt or ester or prodrug thereof.

In clinical use of the compounds of the invention, pharmaceutically-acceptable additives may be added thereto to formulate various preparations in accordance with the intended administration route thereof, and the preparations may be administered. Various additives generally used in the field of pharmaceutical compositions may be used herein, including, for example, gelatin, lactose, sucrose, titanium oxide, starch, crystalline cellulose, methyl cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into various forms of preparations, for example, solid preparations such as tablets, capsules, granules, powders and suppositories; and liquid preparations such as syrups, elixirs and injections. These preparations can be produced in any method known in the field of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto.

The compounds of the invention are effective for animals including humans and other mammals and plants that require the treatment with the compound. For the mammals, humans are preferred and they may be either men or women. The mammals except humans are, for example, companion animals such as dogs and cats. The compounds of the invention are effective also for obesity and obesity-related disorders of dogs and cats. Any ordinary physicians, veterinarians and clinicians may readily determine the necessity, if any, of the treatment with the compound of the invention.

When the compound of the invention is, for example, put into clinical use, then its dose and its administration frequency may vary depending on the sex, the age, the body weight and the condition of the patient and on the type and the range of the necessary treatment with the compound. In oral administration, in general, the dose of the compound may be from 0.01 to 100 mg/kg of adult/day, preferably from 0.03 to 1 mg/kg of adult/day, and the administration frequency is preferably from one to a few times; and in parenteral administration, the dose may be from 0.001 to 10 mg/kg of adult/day, preferably from 0.001 to 1.1 mg/kg of adult/day, more preferably from 0.01 to 0.1 mg/kg of adult/day, and the administration frequency is preferably from one to a few times. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing obesity and/or diabetes mellitus and/or hyperlipemia and/or dyslipidemia and/or non-alcoholic fatty liver disease, or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Ordinary physicians, veterinarians and clinicians may readily determine the effective dose of the pharmaceutical compound necessary to treat, prevent, inhibit, retard or stop the intended disease, and may readily treat the diseased patient with the compound.

The preparation may contain the compound of the invention in an amount of from 1.0 to 100% by weight, preferably from 1.0 to 60% by weight of the preparation. The preparation may contain any other therapeutically-effective compound.

In their use, the compounds of the invention may be combined with any other therapeutic agents that are useful for the treatment of disorders, for example, vascular diseases such as hypertension, cardiac angina, heart failure, cardiac infarction, stroke, claudication, diabetic nephropathy, diabetic retinopathy, eyesight failure, electrolyte abnormality and arteriosclerosis; nervous system diseases such as bulimia and diabetic neuropathy; metabolic diseases such as metabolic syndrome, obesity, diabetes, pre-diabetes, insulin resistance, hyperlipemia, hypercholesterolemia, hypertriglyceridemia, dyslipidemia, non-alcoholic fatty liver disease, hormone secretion failure, gout and hepatic steatosis; genital diseases such as emmeniopathy and sexual dysfunction; digestive tract diseases such as liver dysfunction, pancreatitis, cholecystitis and gastroesophageal reflux; respiratory system diseases such as Pickwickian syndrome and sleep apnea syndrome; infectious diseases caused by bacteria, fungi or parasites; malignant neoplasm; and inflammatory diseases such as arthritis and skin ulcer. The individual ingredients to be combined may be administered at the same time or at different times during the treatment period, either as one preparation or as different preparations. Accordingly, the invention should be so interpreted that it encompasses any and every administration mode at the same time or at different times, and the administration in the invention should be interpreted so. The range of the combination of the compound of the invention and the other therapeutic agent useful for the above-mentioned disorders encompasses, in principle, all combinations of the compound of the invention and any and every pharmaceutical agent useful for the above-mentioned disorders.

The combination includes not only the composition of compounds of the invention and one other active substance but also the composition of compounds of the invention and two or more other active substances. There are a lot of examples of the combinations of a compound of the invention and one, two or more active substances selected from the therapeutic agents for the above-mentioned disorders. For example, for the treatment, management and prevention of metabolic syndrome, a combination of a compound of the invention and one, two or more active substances selected from hypolipidemic agents, lipid lowering agents, and anti-diabetic agents is useful. In particular, a composition that also contains an anti-obesity agent and an anti-hypertension agent, in addition to an anti-diabetic agent and/or a hypolipidemic agent or lipid lowering agent, may exhibit a synergistic effect for treatment, management and prevention of metabolic syndrome.

The pharmaceutical agents that may be combined with the compound of the invention are, for example, ACAT inhibitor, α-blocker, aldose reductase inhibitor, α-amylase inhibitor, angiotensin-converting enzyme inhibitor, angiotensin receptor antagonist, anion exchange resin, anorectic, antioxidant, antiplatelet, β-blocker, biguanide agent, calcium antagonist, CB1 receptor inverse agonist/antagonist, CETP inhibitor, cholesterol absorption inhibitor, DGAT inhibitor, DP-IV inhibitor, diuretic, eicosapentaenoic acid, endothelin antagonist, FLAP inhibitor, FXR modulator, Ghrelin antagonist, GLP-1 agonist, GLP-1 secretagogue, glucagon antagonist, glucokinase activator, glucocorticoid receptor ligand, α-glucosidase inhibitor, GPAT inhibitor, histamine-H3 receptor ligand, HMG-CoA reductase inhibitor, HSD inhibitor, 11-beta HSD-1 inhibitor, insulin and insulin mimetics, kinase inhibitors such as VEGF inhibitor and PDGF inhibitor, leptin, lipase inhibitor, 5-LO inhibitor, LXR ligand, melanocortin agonist, MCH antagonist, MTTP inhibitor, orexin antagonist, opioid antagonist, neuropeptide Y antagonist, nicotinic acid agonist, PPAR ligand, PTP-1B inhibitor, SCD-1 inhibitor, serotonin transporter inhibitor, SGLT inhibitor, SUR ligand, thyroid hormone agonist, UCP activator, VPAC receptor agonist.

More concretely, examples of the other active ingredients that can be combined with a compound of the invention as different or the same pharmaceutical compositions are shown below, which, however, do not restrict the invention.

(a) Anti-diabetic medicines or agents, for example, (1) glitazones (e.g., ciglitazone, darglitazone, englitazone, isaglitazone (MCC-555), pioglitazone, rosiglitazone, troglitazone, tularik, BRL49653, CLX-0921, 5-BTZD), and PPAR-γ agonists such as GW-0207, LG-100641 and LY-300512; (2) biguanides such as buformin, metformin and phenformin; (3) protein tyrosine phosphatase-1B (PTP-1B) inhibitors; (4) sulfonylureas such as acetohexamide, chlorpropamide, diabinese, glibenclamide, glipizide, glyburide, glimepiride, gliclazide, glipentide, gliquidone, glisolamide, tolazamide and tolbutamide; (5) meglitinides such as repaglinide, nateglinide, and the like; (6) α-glucosidase inhibitors such as acarbose, adiposine, camiglibose, emiglitate, miglitol, voglibose, pradimicin-Q, salbostatin, CKD-711, MDL-25,637, MDL-73,945, and MOR14; (7) α-amylase inhibitors such as tendamistat, trestatin, and Al-3688; (8) insulin secretagogues such as linogliride, A-4166 and the like; (9) fatty acid oxidation inhibitors such as clomoxir, and etomoxir; (10) α-2 antagonists such as midaglizole, isaglidole, deriglidole, idazoxan, earoxan, and fluparoxan; (11) insulin and insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$; (12) non-thiazolidinediones such as JT-501, farglitazar (GW-2570/GI-262579), and muraglitazar; PPAR α/δ agonists, such as muraglitazar, and the compounds disclosed in U.S. Pat. No. 6,414,002; (13) PPAR-α/γ dual agonists such as MK-0767/KRP-297, CLX-0940, GW-1536, GW-1929, GW-2433, L-796449, LR-90, and SB219994; (14) other insulin sensitizers; (15) VPAC2 receptor agonists; (16) glucokinase activators; and (17) DPP-4 inhibitors, such as sitagliptin (Januvia™), isoleucine thiazolidide (P32/98); NVP-DPP-728; vildagliptin (LAF 237); P93/01; denagliptin (GSK 823093), SYR322, RO 0730699, TA-6666, and saxagliptin (BMS 477118).

(b) lipid lowering agents, for example, (1) bile acid sequestrants such as cholestyramine, colesevelam, colestipol, dialkylaminoalkyl derivatives of a cross-linked dextran, Colestid®, LoCholest®, and Questran®, and the like; (2) HMG-CoA reductase inhibitors such as atorvastatin, itavastatin, fluvastatin, lovastatin, pitavastatin, pravastatin, rivastatin, rosuvastatin, and simvastatin, ZD-4522, and the like; (3) HMG-CoA synthase inhibitors; (4) cholesterol absorption inhibitors such as stanol esters, β-sitosterol, sterol glycosides such as tiqueside, and azetidinones like ezetimibe; (5) acyl coenzyme A-cholesterol acyl-transferase (ACAT) inhibitors such as avasimibe, eflucimibe, KY505, and SMP797, and the like; (6) CETP inhibitors such as JTT705, torcetrapib, CP532632, BAY63-2149, SC591, and SC795, and the like; (7) squalene synthase inhibitors; (8) antioxidants such as probucol; (9) PPAR-α agonists such as beclofibrate, benzafibrate, ciprofibrate, clofibrate, etofibrate, fenofibrate, gemcabene, gemfibrozil, and other fibric acid derivatives, e.g., GW7647, BM170744, LY518674, Atromid®, Lopid®, and Tricor®, and compounds described in WO 97/36579, and the like; (10) FXR receptor modulators such as GW4064, SR103912, and the like; (11) LXR receptor ligands such as GW3965, T9013137, and XTCO179628, and the like; (12) lipoprotein synthesis inhibitors such as niacin; (13) renin/angiotensin system inhibitors; (14) PPAR-δ partial agonists; (15) bile acid reabsorption inhibitors such as BARI1453, SC435, PHA384640, S8921, AZD7706, and the like; (16) PPAR-δ agonists such as GW501516, GW590735, and compounds described in WO97/28149, and the like; (17) triglyceride synthesis inhibitors, (18) microsomal triglyceride transport (MTTP) inhibitors such as inplitapide, LAB687, and CP346086; (19) transcription modulators, (20) squalene epoxidase inhibitors; (21) low-density lipoprotein (LDL) receptor inducers; (22) platelet aggregation inhibitors; (23) 5-LO or FLAP inhibitors; and (24) niacin receptor agonists; and (c) anti-hypertensive agents, for example, (1) diuretics such as thiazides including chlorthalidone, chlorothiazide, dichlorphenamide, hydroflumethiazide, indapamide and hydrochlorothiazide; loop diuretics such as bumetanide, ethacrynic acid, furosemide, and torsemide; potassium sparing agents such as amiloride, triamterene; aldosterone antagonists such as spironolactone, and epirenone, and the like; (2) β-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, and verapamil, and the like; (4) angiotensin converting enzyme (ACE) inhibitors such as benazepril, captopril, cilazapril, delapril, enalapril, fosinopril, imidapril, lisinopril, moexipril, quinapril, quinaprilat, ramipril, perindopril, perindropril, quanipril, spirapril, tenocapril, trandolapril, and zofenopril, and the like; (5) neutral endopeptidase inhibitors such as omapatrilat, cadoxatril, ecadotril, fosidotril, sampatrilat, AVE7688, ER4030, and the like; (6) endothelin antagonists such as bosentan, tezosentan, A308165, and YM62899, and the like; (7) vasodilators such as hydralazine, clonidine, minoxidil, and nicotinyl alcohol; (8) angiotensin II receptor antagonists such as candesartan, eprosartan, irbesartan, losartan, losartan and hydrochlorothiazide, pratosartan, tasosartan, telmisartan, valsartan, EXP- 3137, FI6828K, and RNH6270, and the like; (9) α/β-adrenergic blockers such as nipradilol, arotinolol, and amosulalol; (10) α1 blockers such as terazosin, urapidil, prazosin, bunazosin, trimazosin, doxazosin, naftopidil, indoramin, WHIP164, and XEN010; (11) α2 agonists such as lofexidine, tiamenidine, moxonidine, rilmenidine, and guanobenz; (12) aldosterone inhibitors; and (d) anti-obesity agents, for example, (1) 5HT (serotonin) transporter inhibitors such as paroxetine, fluoxetine, fenfluramine, fluvoxamine, sertraline, and imipramine; (2) NE (norepinephrine) transporter inhibitors such as GW320659, despiramine, talsupram, nomifensine, and the like; (3) CB-1 (cannabinoid-1 receptor) antagonists/inverse agonists such as rimonabant (Sanofi Synthelabo), SR-147778 (Sanofi Synthelabo), BAY65-2520 (Bayer), SLV319 (Solvey); and the compounds disclosed in U.S. Pat. Nos. 5,532,237, 4,973,587, 5,013,837, 5,081,122, 5,112,820, 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, WO04/048317, WO05/000809, and EPO NO. EP-658546, EP656354, EP576357; (4) ghrelin antagonists such as those disclosed in WO01/87335, WO02/08250; (5) H3 (histamine H3) antagonists/inverse agonists such as thioperamide, 3-(1H-imidazol-4-yl)propyl N-(4-pentenyl) carbamate, clobenpropit, iodophenpropit, imoproxifan, GT2394 (Gliatech), A331440, and those disclosed in WO02/15905, O-[3-(1H-imidazol-4-yl)propanol]carbamates (Kiec-Kononowicz, K. et al., *Pharmazie,* 55:349-355 (2000)), piperidine-containing histamine H3-receptor antagonists (Lazewska, D. et al., *Pharmazie,* 56:927-932 (2001)), benzophenone derivatives and related compounds (Sasse, A. et al., *Arch. Pharm.* (Weinheim) 334:45-52 (2001)), substituted N-phenylcarbamates (Reidemeister, S. et al., Pharmazie, 55:83-86 (2000)), and proxifan derivatives (Sasse, A. et al., *J. Med. Chem.,* 43:3335-3343 (2000)); (6) melanin-concentrating hormone-1 receptor (MCH1R) antagonists such as T-226296 (Takeda), SNP-7941 (Synaptic), and those disclosed in WO01/82925, WO01/87834, WO02/051809, WO02/06245, WO02/076929, WO02/076947, WO02/04433, WO02/51809, WO02/083134, WO02/094799, WO03/004027, and Japanese Patent Application No. JP13226269, JP2004-139909; (7) MCH2R (melanin-concentrating hormone 2R) agonists/antagonists; (8) NPY1 (neuropeptide Y Y1) antagonists such as BIBP3226, 2-[1-(5-chloro-3-isopropyloxycarbonylaminophenyl)ethyl-amino]-6-[2-(5-ethyl-4-methyl-1,3-thiazol-2-yl)ethyl]-4-morpholinopyridine, BIBO3304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; (9) NPY5 (neuropeptide Y Y5) antagonists such as L-152,804, GW-569180A, GW-594884A, GW-587081X, GW-548118X, FR235,208, FR-226928, FR240662, FR252384, 1229U91, GI-264879A, CGP71683A, LY-377897, LY366377, PD-160170, SR-120562A, SR-120819A, JCF-104, H409/22, and the compounds disclosed in U.S. Pat. Nos. 6,057,335, 6,043,246, 6,140,354, 6,166,038, 6,180,653, 6,191,160, 6,258,837, 6,313,298, 6,337,332, 6,329,395, 6,340,683, 6,326,375, 6,329,395, 6,337,332, 6,335,345, 6,388,077, 6,462,053, 6,649,624, 6,723,847, EPO EP-01010691, EP-01044970, PCT WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/094789, WO02/094825, WO03/014083, WO03/10191, WO03/092889, WO2004/002986, WO2004/031175, and Norman et al., *J. Med. Chem.,* 43:4288-4312 (2000); (10) leptins such as recombinant human leptin (PEG-OB, Hoffman La Roche), and recombinant methionyl human leptin (Amgen); (11) leptin derivatives such as those disclosed in U.S. Pat. Nos. 5,552,524, 5,552,523, 5,552,522, 5,521,283, PCT WO96/23513, WO96/23514, WO96/23515, WO96/23516, WO96/23517, WO96/23518, WO96/23519, and WO96/23520; (12) opioid antagonists such as nalmefene (Revex®), 3-methoxynaltrexone, naloxone, naltrexone, and the compounds disclosed in WO00/21509; (13) orexin antagonists such as SB-334867-A, and the compounds disclosed in WO01/96302, WO01/68609, WO02/51232, WO02/51838, and WO03/023561; (14) BRS3 (bombesin receptor subtype 3) agonists such as [D-Phe6,beta-Ala11,Phe13, Nle14]Bn(6-14) and [D-Phe6,Phe13]Bn(6-13)propylamide, and those compounds disclosed in Pept. Sci. 2002 August; 8(8): 461-75); (15) CCK-A (cholecystokinin-A) agonists such as AR-R15849, GI181771, JMV-180, A-71378, A-71623, SR146131, and the compounds disclosed in U.S. Pat. No. 5,739,106; (16) CNTF (ciliary neurotrophic factors) such as GI-181771 (Glaxo-SmithKline), SR146131 (Sanofi Synthelabo), butabindide, and PD170292 and PD149164 (Pfizer); (17) CNTF derivatives such as axokine (Regeneron), and the compounds disclosed in WO94/09134, WO98/22128, and WO99/43813; (18) GHS (growth hormone secretagogue receptor) agonists such as NN703, hexarelin, MK-0677, SM-130686, CP-424,391, L-692,429, L-163,255, and the compounds disclosed in U.S. Pat. Nos. 5,536,716, 6,358,951, USP Application Nos. 2002/049196, 2002/022637, WO01/56592, and WO02/32888; (19) 5HT2c (serotonin receptor 2c) agonists such as BVT933, DPCA37215, IK264, PNU22394, WAY161503, R-1065, YM348, and the compounds disclosed in U.S. Pat. No. 3,914,250, WO02/36596, WO02/48124, WO02/10169, WO01/66548, WO02/44152, WO02/51844, WO02/40456, and WO02/40457; (20) Mc3r (melanocortin-3 receptor) agonists; (21) Mc4r (melanocortin-4 receptor) agonists such as CHIR86036 (Chiron), ME-10142 and ME-10145 (Melacure), PT-141 and PT-14 (Palatin), and the compounds disclosed in U.S. Pat. Nos. 6,410,548, 6,294,534, 6,350,760, 6,458,790, 6,472,398, 6,376,509, and 6,818,658, USP Application No. US2002/0137664, US2003/0236262, US2004/009751, US2004/0092501, WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847, WO04/024720, WO04/078716, WO04/078717, WO04/087159, WO04/089307 and WO05/009950; (22) monoamine reuptake inhibitors such as sibutramine (Meridia®/Reductil®) and its salts, and the compounds disclosed in U.S. Pat. Nos. 4,746,680, 4,806,570, 5,436,272, USP Publication No. 2002/0006964, and WO01/27068, and WO01/62341; (23) serotonin reuptake inhibitors such as dexfenfluramine, fluoxetine, paroxetine, sertraline, and the compounds disclosed in U.S. Pat. No. 6,365,633, and WO01/27060, and WOO/162341; (24) GLP-1 (glucagon-like peptide-1) agonists; (25) topiramate (Topimax®); (26) Phytopharm compound 57 (CP644,673); (27) ACC2 (acetyl-CoA carboxylase-2) inhibitors; (28) P3 (β-adrenergic receptor-3) agonists such as AD9677/TAK677 (Dainippon/Takeda), CL-316, 243, SB418790, BRL-37344, L-796568, BMS-196085, BRL-35135A, CGP12177A, BTA-243, GW427353, trecadrine, Zeneca D7114, SR59119A, and the compounds disclosed in USP Application No. 5,705,515, U.S. Pat. No. 5,451,677, and WO94/18161, WO95/29159, WO97/46556, WO98/04526, WO98/32753, WO01/74782 and WO02/32897; (29) DGAT1 (diacylglycerol acyltransferase-1) inhibitors; (30) DGAT2 (diacylglycerol acyltransferase-2) inhibitors; (31) FAS (fatty acid synthase) inhibitors such as cerulenin, C75; (32) PDE (phosphodiesterase) inhibitors such as theophylline, pentoxifylline, zaprinast, sildenafil, aminone, milrinone, cilostamide, rolipram, and cilomilast; (33) thyroid hormone-s agonists such as KB-2611 (KaroBioBMS), and the compounds disclosed in WO02/15845 and Japanese Patent Application No. JP2000256190; (34) UCP-1 (uncoupling protein-1), 2 and 3 activators such as phytanic acid, 4-[(E)-2-(5,6,7,8-tetrahydro-5,5,8,8-tetramethyl-2-naphthalenyl)-1-propenyl] benzoic acid (TTNPB), retinoic acid, and the compounds disclosed in WO99/00123; (35) acyl-estrogens such as oleoyl-estrones disclosed in del Mar-Grasa, M. et al., *Obesity Research*, 9:202-209 (2001); (36) glucocorticoid antagonists; (37) 11βHSD-1 (11-β-hydroxysteroid dehydrogenase type 1) inhibitors such as BVT3498, BVT2733, and the compounds disclosed in WO01/90091, WO01/90090, and WO01/90092, and U.S. Pat. No. 6,730,690 and USP Application No. 2004/0133011; (38) SCD-1 (stearoyl-CoA desaturase-1) inhibitors; (39) dipeptidyl peptidase IV (DP-IV) inhibitors such as isoleucine thiazolidide, valine pyrrolidide, NVP-DPP728, LAF237, P93/01, TSL225, TMC-2A/2B/2C, FE999011, P9310/K364, VIP0177, SDZ274-444, and the compounds disclosed in U.S. Pat. No. 6,699,871, WO03/004498, WO03/004496, EP1258476, WO02/083128, WO02/062764, WO03/000250, WO03/002530, WO03/002531, WO03/002553, WO03/002593, WO03/000180, and WO03/000181; (40) lipase inhibitors such as tetrahydrolipstatin (orlistat/Xenical®), Triton WR11339, RHC80267, lipstatin, teasaponin, diethylumbelliferyl phosphate, FL-386, WAY-121898, Bay-N-3176, valilactone, esteracin, ebelactone A, ebelactone B, RHC80267, and the compounds disclosed in WO01/77094, U.S. Pat. Nos. 4,598,089, 4,452,813, 5,512,565, 5,391,571, 5,602,151, 4,405,644, 4,189,438, and 4,242,453; (41) fatty acid transporter inhibitors; (42) dicarboxylate transporter inhibitors; (43) glucose transporter inhibitors; (44) phosphate transporter inhibitors; (45) melanocortin agonists such as melanotan II and the compounds described in WO99/64002, and WO00/746799; (46) melanin condensating hormone antagonists such as the compounds disclosed in WO01/21577 and WO01/21169; (47) galanin antagonists; (48) CCK agonists; (49) corticotropin-releasing hormone agonists; and (50) phosphodiesterase-3B (PDE3B) inhibitors; (51) 5HT-2 agonists; (52) histamine receptor-3 (H3) modulators; (53) β-hydroxy steroid dehydrogenase-1 inhibitors (β-HSD-1); (54) anti-obesity serotonergic agents, such as fenfluramine, dexfenfluramine, phentermine, and sibutramine; (55) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (56) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (57) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (58) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (59) a minorex; (60) amphechloral; (61) amphetamine; (62) benzphetamine; (63) chlorphentermine; (64) clobenzorex; (65) cloforex; (66) clominorex; (67) clortermine; (68) cyclexedrine; (69) dextroamphetamine; (70) diphemethoxidine, (71) N-ethylamphetamine; (72) fenbutrazate; (73) fenisorex; (74) fenproporex; (75) fludorex; (76) fluminorex; (77) furfurylmethylamphetamine; (78) levamfetamine; (79) levophacetoperane; (80) mefenorex; (81) metamfepramone; (82) methamphetamine; (83) norpseudoephedrine; (84) pentorex; (85) phendimetrazine; (86) phenmetrazine; (87) picilorex; (88) zonisamide, and (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710; 90) Qnexa; and (91) bupropion; and (e) (1) Glucagon Receptor Agonists; (2) G Protein Receptor Agonist-40 (GPR-40) also called SNORF 55 such as BG 700, and those disclosed in WO 04/041266, 04/022551, 03/099793; (3) G Protein Receptor Agonist-119 (GPR119, also called RUP3; SNORF 25)—such as RUP3, HGPRBMY26, PFI 007, SNORF 25; (4) G Protein Receptor Agonist 131; (5) Selective Peroxisome Proliferator Activator Receptor Modulator (SPPARMS, also known as selective PPAR gamma modulators)—such as T131 (Amgen), FK614 (Fujisawa), netoglitazone, and metaglidasen; (6) oxyntomodulin; (7) SGLT inhibitors (sodium dependent glucose transporter inhibitors)—such as AVE 2268, KGT 1251, T1095/RWJ 394718.

The present agent may be combined with non-drug therapy such as kinesitherapy, dietetic treatment, and radiation therapy.

The compound and the combined compositions of the invention are effective for treating and preventing diabetes. The term "diabetes" as used herein includes both insulin-dependent diabetes (that is, also known as IDDM, type-1 diabetes), and insulin-independent diabetes (that is, also known as NIDDM, type-2 diabetes).

Diabetes is characterized by a fasting plasma glucose level of greater than or equal to 126 mg/dl. A diabetic subject has a fasting plasma glucose level of greater than or equal to 126 mg/dl. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of $\geq 140$ mg/dl and <200 mg/dl); or insulin resistance, resulting in an increased risk of developing diabetes.

The compounds and compositions of the invention are useful for treatment of both type-1 diabetes and type-2 diabetes. The compounds and compositions are especially useful for treatment of type-2 diabetes. The compounds and compositions of the invention are especially useful for treatment and/or prevention of pre-diabetes. Also, the compounds and compositions of the invention are especially useful for treatment and/or prevention of gestational diabetes mellitus.

Treatment of diabetes mellitus refers to the administration of a compound or combination of the present invention to treat a diabetic subject. One outcome of the treatment of diabetes is to reduce an increased plasma glucose concentration. Another outcome of the treatment of diabetes is to reduce an increased insulin concentration. Still another outcome of the treatment of diabetes is to reduce an increased blood triglyceride concentration. Still another outcome of the treatment of diabetes is to increase insulin sensitivity. Still another outcome of the treatment of diabetes may be enhancing glucose tolerance in a subject with glucose intolerance. Still another outcome of the treatment of diabetes is to reduce insulin resistance. Another outcome of the treatment of diabetes is to lower plasma insulin levels. Still another outcome of treatment of diabetes is an improvement in glycemic control, particularly in type 2 diabetes. Yet another outcome of treatment is to increase hepatic insulin sensitivity.

Prevention of diabetes mellitus, in particular diabetes associated with obesity, refers to the administration of a compound or combination of the present invention to prevent or treat the onset of diabetes in a subject in need thereof. A subject in need of preventing diabetes in a prediabetic subject.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Dyslipidemia includes atherogenic dyslipidemia. Hyperlipidemia is associated with abnormally high levels of lipids, LDL and VLDL cholesterol, and/or triglycerides. An outcome of the treatment of dyslipidemia, including hyperlipemia, is to reduce an increased LDL cholesterol concentration. Another outcome of the treatment is to increase a low-concentration of HDL cholesterol. Another outcome of treatment is to decrease very low density lipoproteins (VLDL) and/or small density LDL.

The term "metabolic syndrome", also known as syndrome X, is defined in the Third Report of the National Cholesterol Education Program Expert Panel on Detection, Evaluation and Treatment of High Blood Cholesterol in Adults (ATP-D). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "obesity" as used herein is a condition in which there is an excess of body fat, and includes visceral obesity. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians than that in Europeans and Americans. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, impaired glucose tolerance, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be decreasing body fat, including visceral body fat. Another outcome of treatment may be preventing body weight gain. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The invention is described more concretely with reference to Examples and Reference Examples mentioned below, which, however, do not restrict the invention.

In thin-layer chromatography in Examples, Silica gel$_{60}$F$_{254}$ (Merck) was used as the plate; and a UV detector was used for detection. In column silica gel, used was Wakogel™ C-300 or C-200 (Wako Jun-yaku), FLASH+ cartridge (Biotage) or Chromatorex (FUJI SILYSIA CHEMICAL). In high-performance partitioning liquid chromatography, used was ODS (C18) filler. The MS spectrum was determined through electrospray ionization (ESI), using Micromass ZQ2000 (Waters). In NMR spectrometry, used was dimethylsulfoxide as the internal standard in a deuterated dimethylsulfoxide solution, or used was tetramethylsilane as the internal standard in a deuterated chloroform solution. For it, used was a spectrophotometer of JNM-AI400 (JEOL), Mercury400 (400 MHz; Varian) or Inova400 (400 MHz; Varian), and the total δ value was shown as ppm.

Abbreviations in NMR have the following meanings: s: singlet; d: doublet; dd: double doublet; t: triplet; dt: double triplet; q: quartet; m: multiplet; br: broad; br m: broad multiplet; J: coupling constant; Hz: hertz; DMSO-d$_6$: deuterated dimethylsulfoxide; and CDCl$_3$: deuterated chloroform.

Abbreviations in Examples have the following meanings: aq: aqueous; HOBT: 1-hydroxybenzotriazole hydrate; NMP: N-methylpyrrolidone; WSC: 1-(3-dimethylamino-propyl)-3-ethylcarbodiimide; DMF: dimethylformamide; Et: ethyl; Et$_2$O: diethyl ether; Et$_3$N: triethylamine; EtOAc: ethyl acetate; EDCI: 1-(3-dimethylaminopropyl)-3-ethylcarbodiimide hydrochloride; TEA: triethylamine; g: gram; HCl: hydrochloric acid; Hex: hexane; kg: kilogram; l or L: liter; ml or mL: milliliter; mg: milligram; MeOH: methanol; N: normal; NMO: N-methylmorpholine N-oxide; TPAP: tetrapropylammonium perruthenate; THF: tetrahydrofuran; TFA: trifluoroacetic acid; Tf$_2$O: trifluoromethanesulfonic anhydride; CHCl$_3$: chloroform; μL: microliter; r.t.: room temperature; sat: saturated; Me: methyl; EtOH: ethanol; BuOH: butanol; EtI: ethyl iodide; MeI: methyl iodide; Ts: tosylate; AcOK: potassium acetate; AcOEt: ethyl acetate; h: hour; min: minute(s); dil: dilute; DMAP: 4-dimethylaminopyridine; Boc: tert-butoxy; TBSCl: tert-butyldimethylsilyl chloride; ODS: Octadecylsilica; mol: mole; and DPPF or dppf: 1,1'-bis(diphenyl-phosphino)ferrocene.

Example 1

1-[(1-Ethyl-4-methoxy-1H-benzimidazol-6-yl)carbonyl]-6-(1H-tetrazol-5-yl)spiro[chroman-2,4'-piperidine]-4-one

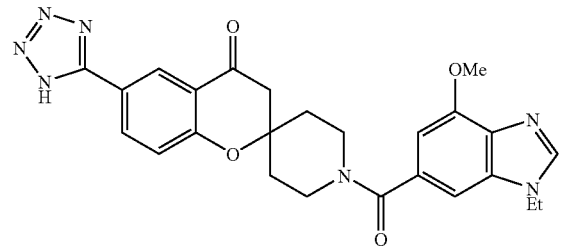

A TFA salt of 3-ethyl-7-methoxy-3H-benzimidazole-5-carboxylic acid methyl ester (182 mg, 0.523 mmol) was dissolved in THF (3 mL) and MeOH (3 mL), aqueous 5 N sodium hydroxide solution (0.52 mL, 2.62 mmol) was added thereto and stirred at room temperature for 2 hours and at 60° C. for 1 hour. This was cooled to room temperature, then 5 N hydrochloric acid (0.55 mL, 2.75 mL) was added thereto, the solvent was evaporated under reduced pressure, and this was azeotroped twice with methanol and once with toluene to obtain a white solid. This material was dissolved in DMF (4 mL) and water (1 mL), and 6-(1H-tetrazol-5-yl)spiro-[chroman-2,4'-piperidin]-4-one hydrochloride (202 mg, 0.628 mmol), triethylamine (0.21 mL, 1.57 mmol), HOBT (106 mg, 0.785 mmol) and EDCI HCl (151 mg, 0.785 mmol) were added thereto. The reaction mixture was stirred at 90° C. for 2 hours, then cooled to room temperature, and water was added thereto. The precipitated solid was collected by filtration, and dried under reduced pressure to obtain the intended compound as a white solid. $^1$H-NMR (400 MHz, DMSO-d$_6$) δ: 8.42 (1H, d, J=2.2 Hz), 8.24 (1H, dd, J=8.8, 2.2 Hz), 8.21 (1H, s), 7.33 (1H, d, J=8.8 Hz), 7.26 (1H, s), 6.73 (1H, s), 4.50-3.25 (4H, m), 4.26 (2H, q, J=7.2 Hz), 3.95 (3H, s), 2.98 (2H, s), 2.15-1.75 (4H, m), 1.38 (3H, t, J=7.2 Hz); MS [M+H]⁺=488.

Example 2

1'-[(3-Cyclopropyl-8-methoxyimidazo[1,2-a]pyridin-6-yl)carbonyl]-6-(1H-tetrazol-5-yl)spiro[chroman-2,4'-piperidin]-4-one

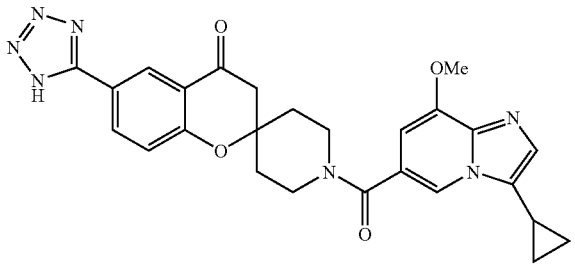

Methyl 3-cyclopropyl-8-methoxyimidazo[1,2-a]pyridin-6-carboxylate (30 mg, 0.122 mmol) was dissolved in THF (1.5 mL) and MeOH (1.5 mL), and added by aqueous 5 N sodium hydroxide solution (0.12 mL, 0.609 mmol), then stirred at 60° C. for 2 hours. This was cooled to room temperature, added by 5 N hydrochloric acid (0.12 mL, 0.609 mL), concentrated under reduced pressure, and then azeotroped with toluene. The residue was dissolved in DMF (2 mL) and water (0.5 mL), and 6-(1H-tetrazol-5-yl)spiro[chroman-2,4'-piperidin]-4-one hydrochloride (47 mg, 0.146 mmol), triethylamine (0.026 mL, 0.183 mmol), HOBT (25 mg, 0.183 mmol) and EDCI HCl (35 mg, 0.183 mol) were added thereto. The reaction mixture was stirred at 90° C. for 2 hours, then cooled to room temperature, and water was added thereto. The precipitated solid was collected by filtration, and dried under reduced pressure to obtain the intended compound as a white solid. ¹H-NMR (400 MHz, DMSO-d₆) δ: 8.42 (1H, s), 8.24 (1H, d, J=8.5 Hz), 8.19 (1H, s), 7.33 (1H, d, J=8.5 Hz), 7.30 (1H, s), 6.68 (1H, s), 4.50-3.20 (5H, m), 3.95 (3H, s), 2.98 (2H, s), 2.10-1.80 (4H, m), 1.03-0.96 (2H, m), 0.69-0.64 (2H, m); MS [M+H]⁺=500.

Example 3

1'-[(1-Cyclopropyl-4-methoxy-1H-indol-6-yl)carbonyl]-6-(5-oxo-4,5-dihydro-1,2,4-oxadiazol-3-yl)spiro[chroman-2,4'-piperidin]-4-one

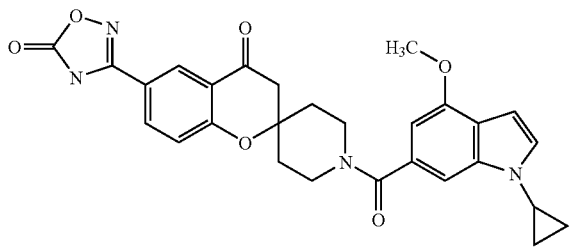

Et3N (58 µL), HOBT (32 mg) and WSC (40 mg) were added to a solution of 1-cyclopropyl-4-methoxy-1H-indol-6-carboxylic acid (40 mg) and 6-(5-oxo-4,5-dihydro-1,2,4-oxadiazol-3-yl)spiro[chroman-2,4'-piperidin]-4-one hydrochloride (70 mg) in DMF (4 mL), and stirred overnight at room temperature. Water was added to the reaction mixture, and the formed solid was collected by filtration. The solid was washed thoroughly with water and ether. This was dried under reduced pressure to obtain the title compound. ¹H-NMR (400 MHz, DMSO-d₆) δ: 12.91 (1H, brs), 8.20 (1H, d, J=4.0 Hz), 8.00 (1H, dd, J=8.0, 4.0 Hz), 7.36-7.26 (2H, m), 7.22 (1H, s), 6.57 (1H, s), 6.39 (1H, d, J=4.0 Hz), 4.20-4.00 (1H, m), 3.87 (3H, s), 3.46-3.40 (1H, m), 3.40-3.20 (3H, m), 2.89 (2H, s), 2.06-1.77 (4H, m), 1.07-1.03 (2H, m), 0.94-0.90 (2H, m); MS [M+H]⁺=515.

Example 4

1'-{[1-Ethyl-4-(2-hydroxyethoxy)-1H-indol-6-yl]carbonyl}-6-(1H-tetrazol-5-yl)spiro[chroman-2,4'-piperidin]-4-one

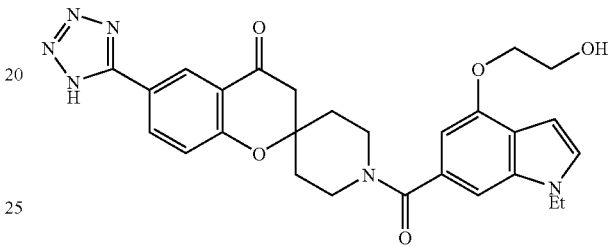

EDCI.HCl (212 mg), HOBT.H₂O (169 mg) and 6-(1H-tetrazol-5-yl)spiro[chroman-2,4'-piperidin]-4-one hydrochloride (170 mg/0.53 mmol) were added in this order at room temperature to a solution of 1-ethyl-4-(2-hydroxyethyl)indole-6-carboxylic acid (110 mg/0.442 mmol) in DMF (1.0 mL), pyridine (1.0 mL) and H₂O (0.5 mL). The reaction mixture was stirred overnight at room temperature, and then concentrated under reduced pressure. CHCl₃ (5 mL) was added to the residue, stirred for 10 minutes, and the insoluble material was removed by filtration. The filtrate was concentrated, then dissolved in DMSO, and purified through reversed-phase HPLC to obtain the intended compound. ¹H-NMR (400 Mz, DMSO-d₆) δ: 8.42 (1H, d, J=2.2 Hz), 8.30 (1H, s), 8.24 (1H, dd, J=8.7, 2.3 Hz), 7.35-7.31 (2H, m), 7.16 (1H, s), 6.52 (1H, s), 6.42 (1H, d, J=2.4 Hz), 4.20-4.12 (4H, m), 3.68 (2H, t, J=5.5 Hz), 3.44-3.27 (3H, m), 2.99 (2H, s), 1.97 (2H, br s), 1.85-1.77 (2H, m), 1.38 (3H, t, J=7.0 Hz), 1.08 (2H, m); MS [M+H]⁺=517.

Example 5

Sodium 3-{1'-[(1-cyclopropyl-4-methoxy-1H-indol-6-yl)carbonyl]-4-oxospiro[chroman-2,4'-piperidin]-6-yl}benzoate

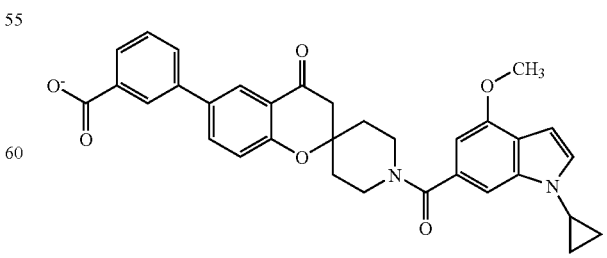

N,N'-carbonyldiimidazole (130 mg) and triethylamine (0.446 mL) were added to a solution of 1-cyclopropyl-4-methoxy-1H-indole-6-carboxylic acid (185 mg) in DMF (4 mL), and stirred at 70° C. for 7 hours. To the reaction mixture was added 3-(4-oxo-spiro[chroman-2,4'-piperidin]-6-yl)benzoic acid hydrochloride (374 mg), which was further stirred at that temperature for 16 hours. 1 N hydrochloric acid and water were added to the reaction mixture, and the formed solid was collected by filtration. The resulting solid was recrystallized from methanol, and purified through silica gel column chromatography (chloroform/methanol) to obtain 3-{1'-[(1-cyclopropyl-4-methoxy-1H-indol-6-yl)carbonyl]-4-oxospiro[chroman-2,4'-piperidin]-6-yl}benzoic acid. This was suspended in water (5 mL), and aqueous 1 N sodium hydroxide solution (0.762 mL) was added thereto and stirred at room temperature for 30 minutes. The solution was purified through ODS reversed-phase column chromatography (water/methanol) to obtain the intended compound. $^1$H-NMR (400 MHz, DMSO-$d_6$) δ: 8.11-8.09 (1H, m), 7.96-7.93 (1H, m), 7.90 (1H, dd, J=8.5, 2.4 Hz), 7.83-7.79 (1H, m), 7.56-7.50 (1H, m), 7.32 (1H, dd, J=7.6, 7.6 Hz), 7.29 (1H, d, J=3.2 Hz), 7.23 (1H, s), 7.20 (1H, d, J=8.5 Hz), 6.59 (1H, s), 6.41-6.39 (1H, m), 4.45-4.11 (1H, br m), 3.86 (3H, s), 3.86-3.55 (1H, br m), 3.52-3.22 (3H, m), 2.93 (2H, s), 2.17-1.64 (4H, br m), 1.11-1.00 (2H, m), 0.96-0.88 (2H, m); MS [M+Na]$^+$=573.

Example 6

5-{1'-[(1-Cyclopropyl-4-methoxy-1H-indol-6-yl)carbonyl]-4-oxospiro[chroman-2,4'-piperidin]-6-yl}nicotinic acid

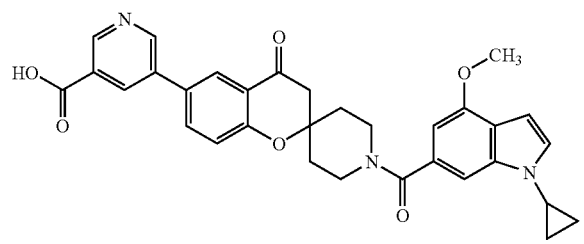

N,N'-carbonyldiimidazole (130 mg) and triethylamine (0.446 mL) were added to a solution of 1-cyclopropyl-4-methoxy-1H-indole-6-carboxylic acid (185 mg) in DMF (4 mL), and stirred at 70° C. for 20 hours. To the reaction mixture was added 5-(4-oxo-spiro[chroman-2,4'-piperidin]-6-yl)nicotinic acid hydrochloride (370 mg), which was further stirred at that temperature for 6 hours. 1 N hydrochloric acid and water were added to the reaction mixture, and the formed solid was collected by filtration. The solid was purified through silica gel column chromatography (chloroform/methanol) to obtain the intended compound. $^1$H-NMR (400 MHz, DMSO-$d_6$) δ: 9.04-9.00 (2H, m), 8.40 (1H, s), 8.06-8.00 (2H, m), 7.30-7.22 (3H, m), 6.58 (1H, s), 6.40 (1H, d, J=3.2 Hz), 4.47-4.01 (1H, m), 3.88 (3H, s), 3.79-3.09 (4H, m), 2.96 (2H, s), 2.15-1.71 (4H, m), 1.09-1.01 (2H, m), 0.96-0.89 (2H, m); MS [M+H]$^+$=552.

Example 7

5-{1'-[(1-Cyclopropyl-4-methoxy-1H-indol-6-yl)carbonyl]-4-oxospiro[chroman-2,4'-piperidin]-6-yl}nicotinic acid sodium salt

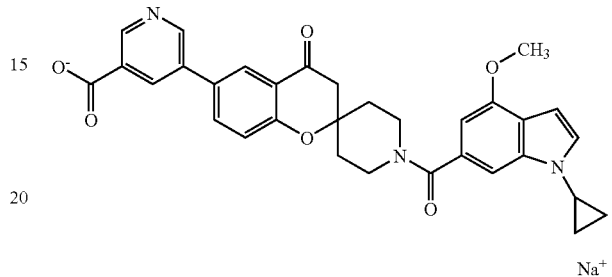

5-{1'-[(1-Cyclopropyl-4-methoxy-1H-indol-6-yl)carbonyl]-4-oxospiro[chroman-2,4'-piperidin]-6-yl}nicotinic acid (434 mg) was suspended in water (5 mL), and aqueous 1 N sodium hydroxide solution (0.865 mL) was added thereto and stirred at room temperature for 1 hour. The solution was purified by ODS reversed-phase column chromatography (water/methanol, gradient) to obtain the intended compound. $^1$H-NMR (400 MHz, DMSO-$d_6$) δ: 8.90 (1H, d, J=1.7 Hz), 8.74 (1H, d, J=2.4 Hz), 8.29-8.27 (1H, m), 7.99-7.94 (2H, m), 7.29 (1H, d, J=3.2 Hz), 7.25-7.22 (2H, m), 6.59 (1H, s), 6.40 (1H, d, J=3.2 Hz), 4.49-4.04 (1H, br m), 3.87 (3H, s), 3.82-3.58 (1H, br m), 3.51-3.28 (3H, m), 2.95 (2H, s), 2.13-1.90 (2H, br m), 1.88-1.75 (2H, br m), 1.09-1.02 (2H, m), 0.95-0.90 (2H, m); MS [M+Na]$^+$=574.

Example 8

1'-{[1,4-Dimethoxy-1H-indol-6-yl]carbonyl}-6-(1H-tetrazol-5-yl)spiro[chroman-2,4'-piperidin]-4-one

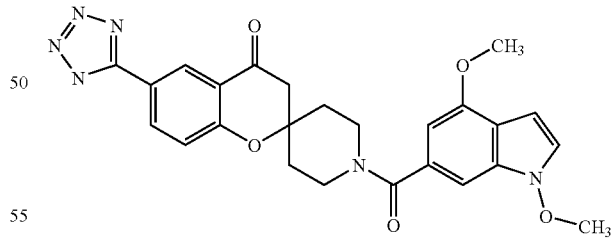

Triethylamine (310 μl) and water (1.5 mL) were added to a solution of 1,4-dimethoxy-1H-indole-6-carboxylic acid (300 mg), 6-(1H-tetrazol-5-yl)spiro[chroman-2,4'-piperidin]-4-one hydrochloride (478 mg), WSC (311 mg) and HOBT (249 mg) in DMF (6 mL), and stirred at 90° C. for 30 minutes. Water was added thereto at room temperature, and a white precipitate was thus obtained. This was dried under reduced pressure, washed with a mixed solvent of methanol and diethyl ether, and dried again under reduced pressure to obtain the above-described compound as a colorless solid.

$^1$H-NMR (400 MHz, DMSO-d$_6$) δ: 8.41 (1H, d, J=2.2 Hz), 8.23 (1H, dd, J=8.5, 2.2 Hz), 7.63 (1H, d, J=3.4 Hz), 7.33 (1H, d, J=8.5 Hz), 7.11 (1H, s), 6.58 (1H, s), 6.37 (1H, d, J=3.4 Hz), 4.34-4.18 (1H, br m), 4.05 (3H, s), 3.89 (3H, s), 3.73-3.14 (3H, br m), 2.98 (2H, s), 2.15-1.76 (4H, br m); MS [M+H]$^+$= 489.

Example 9

1'-{[1,4-Dimethoxy-1H-indol-6-yl]carbonyl}-6-(1H-tetrazol-5-yl)spiro[chroman-2,4'-piperidin]-4-one sodium salt

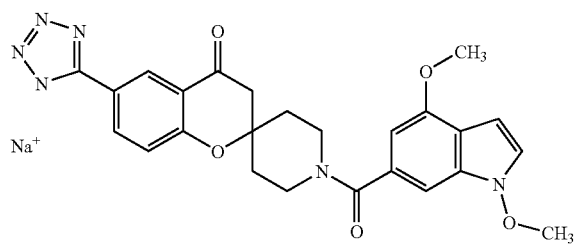

Aqueous 1 N sodium hydroxide solution (495 μl) was added to a solution in water (8 mL) of the free compound (220 mg) obtained in Example 8, and stirred at room temperature for 30 minutes. Next, using Sep-Pak® cartridge (Waters), this was purified to obtain the title compound sodium salt as a colorless amorphous substance. $^1$H-NMR (400 MHz, DMSO-d$_6$) δ: 8.30 (1H, d, J=2.2 Hz), 8.15 (1H, dd, J=8.7, 2.1 Hz), 7.62 (1H, d, J=3.4 Hz), 7.12-7.08 (2H, m), 6.58 (1H, s), 6.37 (1H, dd, J=3.4, 0.7 Hz), 4.30-4.18 (1H, br m), 4.05 (3H, s), 3.89 (3H, s), 3.69-3.25 (3H, br m), 2.90 (2H, s), 2.10-1.71 (4H, br m); MS [M+H]$^+$=489.

Example 10

1'-[(1-Ethyl-4-methoxy-1H-indazol-6-yl)carbonyl]-6-(1H-tetrazol-5-yl)spiro[chroman-2,4'-piperidin]-4-one

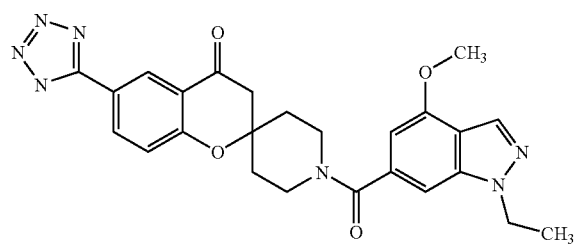

The title compound was obtained as a colorless solid, in the same manner as in Example 2 but using 1-ethyl-4-methoxy-1H-indazole-6-carboxylic acid in place of 1,4-dimethoxy-1H-indole-6-carboxylic acid. $^1$H-NMR (400 MHz, DMSO-d$_6$) δ: 8.42 (1H, d, J=2.2 Hz), 8.24 (1H, dd, J=8.7, 2.3 Hz), 8.04 (1H, d, J=1.0 Hz), 7.33 (1H, d, J=8.8 Hz), 7.29 (1H, s), 6.55 (1H, s), 4.41 (2H, q, J=7.2 Hz), 4.36-4.23 (1H, br m), 3.93 (3H, s), 3.59-3.19 (3H, br m), 2.99 (2H, s), 2.13-1.78 (4H, br m), 1.36 (3H, t, J=7.2 Hz); MS [M+H]$^+$=488.

Example 11

1'-[(1-Cyclopropyl-4-methoxy-1H-indol-6-yl)carbonyl]-6-(1H-tetrazol-5-yl)spiro[chroman-2,4'-piperidin]-4-one

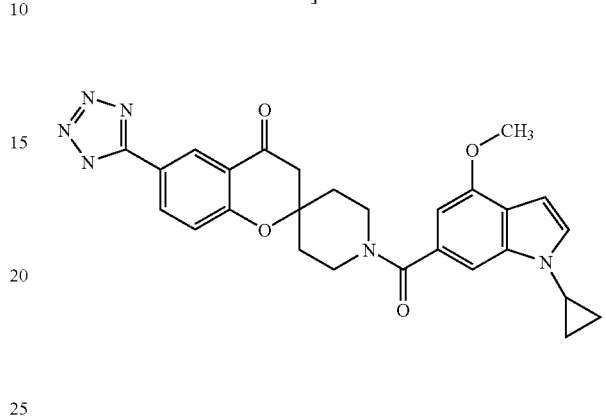

The title compound was obtained as a colorless solid in the same manner as in Example 8 but using 1-cyclopropyl-4-methoxy-1H-indole-6-carboxylic acid in place of 1,4-dimethoxy-1H-indole-6-carboxylic acid. $^1$H-NMR (400 MHz, DMSO-d$_6$) δ: 8.42 (1H, d, J=2.2 Hz), 8.24 (1H, dd, J=8.8, 2.2 Hz), 7.34 (1H, d, J=8.8 Hz), 7.29 (1H, d, J=3.2 Hz), 7.23 (1H, s), 6.58 (1H, s), 6.40 (1H, d, J=3.2 Hz), 4.47-4.10 (1H, br m), 3.87 (3H, s), 3.79-3.21 (4H, br m), 2.99 (2H, s), 2.14-1.73 (4H, br m), 1.08-0.90 (4H, br m); MS [M+H]$^+$= 499.

Example 12

1'-[(1-Cyclopropyl-4-methoxy-1H-indol-6-yl)carbonyl]-6-(1H-tetrazol-5-yl)spiro[chroman-2,4'-piperidin]-4-one sodium salt

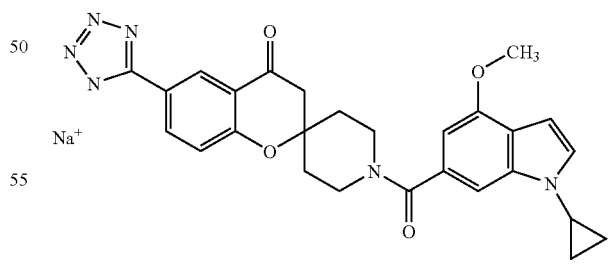

In the same manner as in Example 9, the intended compound was obtained as a colorless amorphous substance from the compound (330 mg) of Example 11. $^1$H-NMR (400 MHz, DMSO-d$_6$) δ: 8.30 (1H, d, J=2.0 Hz), 8.15 (1H, dd, J=8.5, 2.2 Hz), 7.28 (1H, d, J=3.2 Hz), 7.24-7.21 (1H, br m), 7.10 (1H, d, J=8.5 Hz), 6.59 (1H, s), 6.39 (1H, d, J=3.2 Hz), 4.37-4.19

(1H, br m), 3.87 (3H, s), 3.75-3.25 (4H, br m), 2.90 (2H, s), 2.10-1.74 (4H, br m), 1.08-0.90 (4H, br m); MS [M+H]$^+$=499.

Example 13

1'-[(1-Cyclopropyl-4-ethoxy-1H-indol-6-yl)carbonyl]-6-(1H-tetrazol-5-yl)spiro[chroman-2,4'-piperidin]-4-one

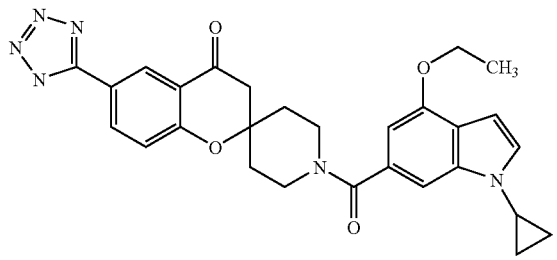

The title compound was obtained as a colorless solid in the same manner as in Example 8 but using 1-cyclopropyl-4-ethoxy-1H-indole-6-carboxylic acid in place of 1,4-dimethoxy-1H-indole-6-carboxylic acid. $^1$H-NMR (400 MHz, DMSO-d$_6$) δ: 8.42 (1H, s), 8.23 (1H, d, J=8.8 Hz), 7.34 (1H, d, J=8.8 Hz), 7.29-7.27 (1H, m), 7.21 (1H, s), 6.56 (1H, s), 6.38 (1H, s), 4.33-4.14 (1H, br m), 4.15 (2H, q, J=7.2 Hz), 3.89-3.17 (4H, br m), 2.99 (2H, s), 2.12-1.78 (4H, br m), 1.38 (3H, t, J=7.2 Hz), 1.09-0.88 (4H, br m); MS [M+H]$^+$=513.

Example 14

1'-[(1-Cyclopropyl-4-ethoxy-1H-indol-6-yl)carbonyl]-6-(1H-tetrazol-5-yl)spiro[chroman-2,4'-piperidin]-4-one sodium salt

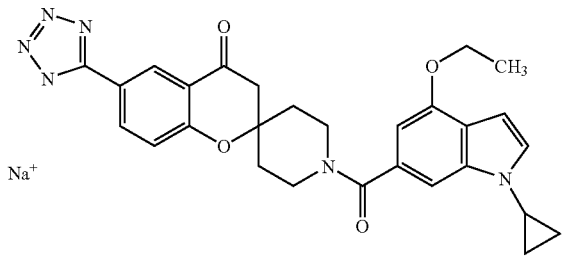

In the same manner as in Example 9, the intended compound was obtained as a colorless amorphous substance from the compound (316 mg) of Example 13. $^1$H-NMR (400 MHz, DMSO-d$_6$) δ: 8.30 (1H, d, J=2.0 Hz), 8.15 (1H, dd, J=8.5, 2.0 Hz), 7.27 (1H, d, J=3.2 Hz), 7.21 (1H, dd, J=0.7, 0.7 Hz), 7.10 (1H, d, J=8.5 Hz), 6.57 (1H, d, J=0.7 Hz), 6.38 (1H, dd, J=3.2, 0.7 Hz), 4.36-4.28 (1H, br m), 4.15 (2H, q, J=7.0 Hz), 3.79-3.27 (4H, br m), 2.90 (2H, s), 2.13-1.71 (4H, br m), 1.38 (3H, t, J=7.0 Hz), 1.10-0.90 (4H, br m); MS [M+H]$^+$=513.

Example 15

1'-[(1,4-Diethoxy-1H-indazol-6-yl)carbonyl]-6-(1H-tetrazol-5-yl)spiro[chroman-2,4'-piperidin]-4-one

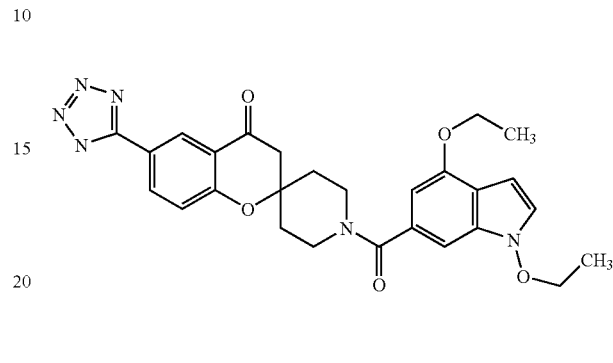

The intended compound was obtained as a colorless solid in the same manner as in Example 8 but using 1,4-diethoxy-1H-indole-6-carboxylic acid in place of 1,4-dimethoxy-1H-indole-6-carboxylic acid. $^1$H-NMR (400 MHz, DMSO-d$_6$) δ: 8.42 (1H, d, J=2.4 Hz), 8.23 (1H, dd, J=8.7, 2.4 Hz), 7.59 (1H, d, J=3.4 Hz), 7.33 (1H, d, J=8.7 Hz), 7.07 (1H, dd, J=0.8, 0.8 Hz), 6.55 (1H, d, J=0.8 Hz), 6.35 (1H, dd, J=3.4, 0.8 Hz), 4.37-4.03 (1H, br m), 4.28 (2H, q, J=7.0 Hz), 4.16 (2H, q, J=7.0 Hz), 3.75-3.21 (3H, br m), 2.98 (2H, s), 2.12-1.75 (4H, br m), 1.39 (3H, t, J=7.0 Hz), 1.29 (3H, t, J=7.0 Hz); MS [M+H]$^+$=517.

Example 16

1'-[(3-Chloro-1-cyclopropyl-4-ethoxy-1H-indol-6-yl)carbonyl]-6-(1H-tetrazol-5-yl)spiro[chroman-2,4'-piperidin]-4-one

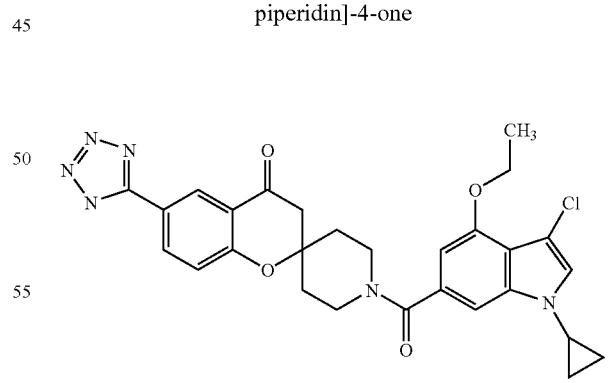

The intended compound was obtained as a colorless solid in the same manner as in Example 8 but using 3-chloro-1-cyclopropyl-4-ethoxy-1H-indole-6-carboxylic acid in place of 1,4-dimethoxy-1H-indole-6-carboxylic acid. $^1$H-NMR (400 MHz, DMSO-d$_6$) δ: 8.42 (1H, d, J=2.4 Hz), 8.24 (1H, dd, J=8.7, 2.4 Hz), 7.43 (1H, s), 7.33 (1H, d, J=8.7 Hz), 7.21 (1H, d, J=1.0 Hz), 6.59 (1H, s), 4.35-4.17 (1H, br m), 4.12

(2H, q, J=7.0 Hz), 3.74-3.19 (4H, br m), 2.99 (2H, s), 2.16-1.72 (4H, br m), 1.37 (3H, t, J=7.0 Hz), 1.08-0.91 (4H, br m); MS [M+H]⁺=547.

Example 17

1'-[(1-Cyclopropyl-4-ethoxy-3-methyl-1H-indol-6-yl)carbonyl]-6-(1H-tetrazol-5-yl)spiro[chroman-2,4'-piperidin]-4-one

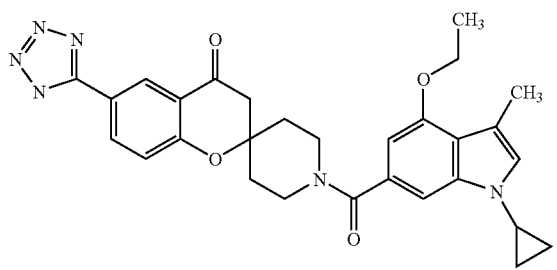

The intended compound was obtained as a colorless solid in the same manner as in Example 8 but using 1-cyclopropyl-4-ethoxy-3-methyl-1H-indole-6-carboxylic acid in place of 1,4-dimethoxy-1H-indole-6-carboxylic acid. ¹H-NMR (400 MHz, DMSO-d₆) δ: 8.41 (1H, d, J=2.4 Hz), 8.23 (1H, dd, J=8.8, 2.4 Hz), 7.32 (1H, d, J=8.8 Hz), 7.12 (1H, d, J=1.0 Hz), 6.99 (1H, d, J=1.0 Hz), 6.48 (1H, s), 4.30-4.14 (1H, br m), 4.08 (2H, q, J=6.9 Hz), 3.79-3.13 (4H, br m), 2.98 (2H, s), 2.33 (3H, d, J=1.0 Hz), 2.08-1.74 (4H, br m), 1.37 (3H, t, J=6.8 Hz), 1.03-0.98 (2H, m), 0.89-0.84 (2H, m); MS [M+H]⁺=527.

Example 18

3-(1'-{[1-Cyclopropyl-4-(2-hydroxyethoxy)-1H-indol-6-yl]carbonyl}-4-oxo-spiro[chroman-2,4'-piperidin]-6-yl)benzoic acid

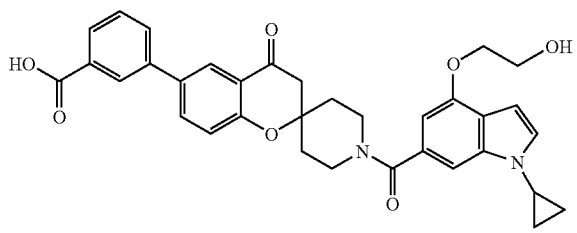

Triethylamine (164 μl) was added to a solution of 1-cyclopropyl-4-(2-hydroxyethoxy)-1H-indole-6-carboxylic acid (166 mg), 3-(4-oxo-spiro[chroman-2,4'-piperidin]-6-yl)benzoic acid methyl ester hydrochloride (124 mg), EDCI.HCl (124 mg) and HOBT (99 mg) in DMF (4 mL), and stirred at 60° C. for 1 hour. Next, this mixture was diluted with ethyl acetate at room temperature, washed with aqueous 1 N hydrochloric acid solution, saturated sodium bicarbonate water, water and saturated saline water in that order, and dried over sodium sulfate. After filtered and concentrated, the mixture was purified through a silica gel column (Biotage) to obtain the ester of the intended compound. Aqueous 5 N sodium hydroxide solution (240 μl) was added to a methanol solution (10 mL) of the ester derivative (380 mg), and stirred at 60° C. for 4 hours. Next, aqueous 5N hydrochloric acid solution (250 μl) was added thereto at room temperature, extracted with a mixed solvent of chloroform and methanol, and dried over sodium sulfate. After filtered and concentrated, the residue was crystallized using a mixed solvent of ethyl acetate and hexane, the above compound was obtained as a colorless crystal. ¹H-NMR (400 MHz, DMSO-d₆) δ: 8.13 (1H, s), 7.98-7.95 (2H, m), 7.93-7.87 (2H, br m), 7.57 (1H, dd, J=8.2, 8.2 Hz), 7.29 (1H, d, J=3.2 Hz), 7.25-7.21 (2H, m), 6.58 (1H, s), 6.42 (1H, d, J=3.2 Hz), 4.90-4.82 (1H, br m), 4.33-4.17 (1H, br m), 4.11 (2H, t, J=5.1 Hz), 3.79-3.74 (2H, br m), 3.51-3.24 (4H, br m), 2.95 (2H, s), 2.10-1.74 (4H, br m), 1.08-1.02 (2H, m), 0.95-0.90 (2H, m); MS [M+H]⁺=581.

Example 19

5-{1'-[(1-Cyclopropyl-4-ethoxy-1H-indol-6-yl)carbonyl]-4-oxo-spiro[chroman-2,4'-piperidin]-6-yl}nicotinic acid sodium salt

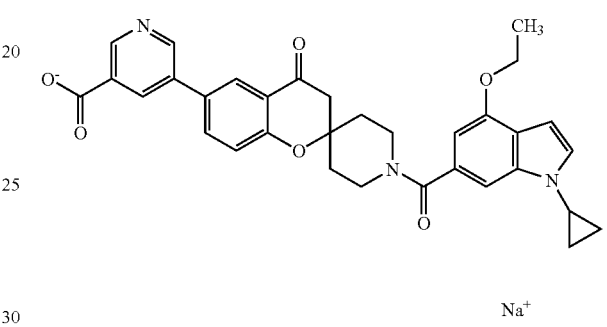

The intended compound was obtained as a colorless amorphous substance according to the methods of Examples 18 and 9, but using 1-cyclopropyl-4-ethoxy-1H-indole-6-carboxylic acid in place of 1-cyclopropyl-4-(2-hydroxyethoxy)-1H-indole-6-carboxylic acid, and using 5-(4-oxo-spiro[chroman-2,4'-piperidin]-6-yl)nicotinic acid methyl ester hydrochloride in place of 3-(4-oxo-spiro[chroman-2,4'-piperidin]-6-yl)benzoic acid methyl ester hydrochloride. ¹H-NMR (400 MHz, DMSO-d₆) δ: 8.90 (1H, d, J=1.7 Hz), 8.74 (1H, d, J=2.4 Hz), 8.28 (1H, dd, J=2.4, 1.7 Hz), 7.99-7.95 (2H, m), 7.28 (1H, d, J=3.2 Hz), 7.25-7.20 (2H, m), 6.57 (1H, s), 6.39 (1H, d, J=3.2 Hz), 4.35-4.20 (1H, br m), 4.15 (2H, q, J=7.0 Hz), 3.75-3.26 (4H, br m), 2.95 (2H, s), 2.11-1.74 (4H, br m), 1.38 (3H, t, J=7.0 Hz), 1.08-1.02 (2H, m), 0.95-0.89 (2H, m); MS [M+H]⁺=566.

Example 20

2-{1'-[(1-Cyclopropyl-4-methoxy-1H-indol-6-yl)carbonyl]-4-oxo-spiro[chroman-2,4'-piperidin]6-yl}isonicotinic acid sodium salt

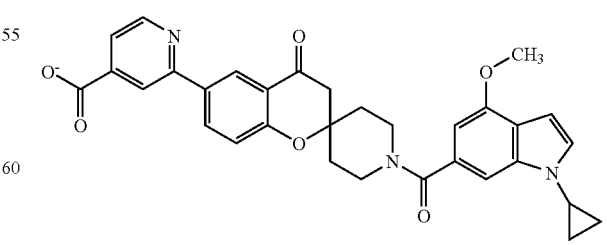

The intended compound was obtained as a colorless amorphous substance according to the methods of Example 18 and Example 9 but using 1-cyclopropyl-4-methoxy-1H-indole-6-carboxylic acid in place of 1-cyclopropyl-4-(2-hydroxyethoxy)-1H-indole-6-carboxylic acid, and using 2-(4-oxo-spiro[chroman-2,4'-piperidin]-6-yl)isonicotinic acid methyl ester hydrochloride in place of 3-(4-oxo-spiro[chroman-2,4'-piperidin]-6-yl)benzoic acid methyl ester hydrochloride. $^1$H-NMR (400 MHz, DMSO-d$_6$) δ: 8.54 (1H, d, J=4.9 Hz), 8.41 (1H, d, J=2.2 Hz), 8.30 (1H, dd, J=8.5, 2.2 Hz), 8.15 (1H, s), 7.59 (1H, dd, J=4.9, 1.0 Hz), 7.29 (1H, d, J=3.4 Hz), 7.23 (1H, s), 7.21 (1H, d, J=8.5 Hz), 6.59 (1H, s), 6.40 (1H, d, J=3.4 Hz), 4.34-4.16 (1H, br m), 3.87 (3H, s), 3.74-3.27 (3H, br m), 3.51-3.41 (1H, m), 2.95 (2H, s), 2.14-1.75 (4H, br m), 1.08-1.03 (2H, m), 0.95-0.90 (2H, m); MS [M+H]$^+$=552.

Example 21

4-{1'-[(1-Cyclopropyl-4-methoxy-1H-indol-6-yl)carbonyl]-4-oxo-spiro[chroman-2,4'-piperidin]-6-yl}pyridine-2-carboxylic acid sodium salt

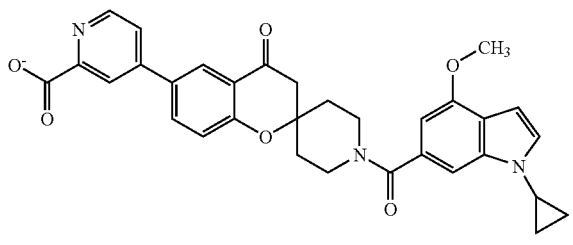

The intended compound was obtained as a colorless amorphous substance according to the methods of Example 18 and Example 9, but using 1-cyclopropyl-4-methoxy-1H-indole-6-carboxylic acid was used in place of 1-cyclopropyl-4-(2-hydroxyethoxy)-1H-indole-6-carboxylic acid, and using 4-(4-oxo-spiro[chroman-2,4'-piperidin]-6-yl)pyridine-2-carboxylic acid methyl ester hydrochloride in place of 3-(4-oxo-spiro[chroman-2,4'-piperidin]-6-yl)benzoic acid methyl ester hydrochloride. $^1$H-NMR (400 MHz, DMSO-d$_6$) δ: 8.47 (1H, d, J=5.4 Hz), 8.14 (1H, d, J=1.2 Hz), 8.07 (1H, d, J=2.2 Hz), 8.04 (1H, dd, J=8.5, 2.2 Hz), 7.59 (1H, dd, J=5.4, 1.2 Hz), 7.29-7.23 (3H, m), 6.58 (1H, d, J=1.2 Hz), 6.40 (1H, dd, J=3.4, 1.2 Hz), 4.41-4.17 (1H, br m), 3.87 (3H, s), 3.77-3.59 (1H, br m), 3.49-3.28 (3H, br m), 2.96 (2H, s), 2.13-1.74 (4H, br m), 1:08-1.02 (2H, m), 0.95-0.90 (2H, m); MS [M+H]$^+$= 552.

Example 22

5-{1'-[(1-Cyclopropyl-4-methoxy-1H-indol-6-yl)carbonyl]-4-oxo-spiro[chroman-2,4'-piperidin]-6-yl}pyridine-2-carboxylic acid sodium salt

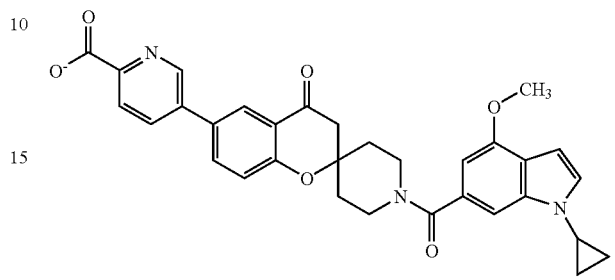

The intended compound was obtained as a colorless amorphous substance, according to the methods of Example 18 and Example 9, but using 1-cyclopropyl-4-methoxy-1H-indole-6-carboxylic acid in place of 1-cyclopropyl-4-(2-hydroxyethoxy)-1H-indole-6-carboxylic acid, and using 5-(4-oxo-spiro[chroman-2,4'-piperidin]-6-yl)pyridine-2-carboxylic acid methyl ester hydrochloride in place of 3-(4-oxo-spiro[chroman-2,4'-piperidin]-6-yl)benzoic acid methyl ester hydrochloride. $^1$H-NMR (400 MHz, DMSO-d$_6$) δ: 8.69 (1H, d, J=1.7 Hz), 8.02-7.94 (4H, m), 7.29 (1H, d, J=3.2 Hz), 7.26-7.22 (2H, m), 6.58 (1H, s), 6.40 (1H, d, J=3.2 Hz), 4.38-4.14 (1H, br m), 3.87 (3H, s), 3.79-3.61 (1H, br m), 3.50-3.31 (3H, br m), 2.95 (2H, s), 2.13-1.75 (4H, br m), 1.09-1.02 (2H, br m), 0.95-0.89 (2H, br m); MS [M+H]$^+$= 552.

Example 23

5-{1'-[(1-Cyclopropyl-4-methoxy-3-methyl-1H-indol-6-yl)carbonyl]-4-oxo-spiro[chroman-2,4'-piperidin]-6-yl}nicotinic acid sodium salt

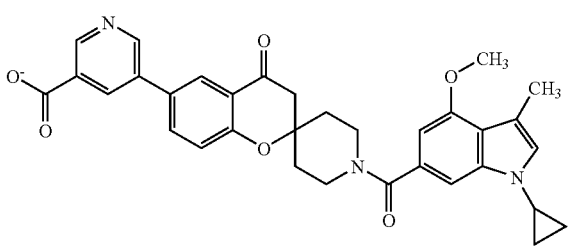

To a mixture of 5-(4-oxo-spiro[chroman-2,4'-piperidin]-6-yl)nicotinic acid methyl ester di-hydrochloride (2.98 g), 1-cyclopropyl-4-methoxy-3-methyl-1H-indole-6-carboxylic acid (1.717 g), EDCI (1.61 g), HOBT (1.286 g) and DMF (40 mL) was added TEA (2.83 g) and the mixture was stirred overnight. The mixture was diluted with EtOAc and H$_2$O, and partitionized. The organic layer was washed with H$_2$O, saturated NaHCO$_3$ aqueous, and brine, dried over Na$_2$SO$_4$, and concentrated. The residue was purified by SiO$_2$ column chromatography (Hexane-EtOAc gradient), crystallized from EtOAc/n-hexane and dried in vacuo to give the methyl ester of the title compound as a colorless solid. 3.0 g of the ester was suspended in 30 mL of THF and 30 mL of MeOH, then 1.5 mL of 5N NaOH aqueous was added thereto. The mixture was stirred overnight and then concentrated. The residue was diluted with 30 mL of MeOH and 22 mL of H$_2$O, and 7.76 mL of 1N HCl aqueous was added thereto. The precipitate was collected by filtration, washed with H$_2$O, and dried in vacuo. The solid was washed with EtOAc-nHexane and dried in vacuo. The material was suspended in water and then 7.76 mL of 1N NaOH aqueous was added thereto. The mixture was purified by ODS column chromatography (MeOH—H$_2$O gradient) to give the title compound as a colorless amorphous substance. $^1$H-NMR (400 MHz, DMSO-d$_6$) δ: 8.91 (1H, d, J=2.0 Hz), 8.75 (1H, d, J=2.4 Hz), 8.29 (1H, dd, J=2.4, 2.0 Hz), 7.99-7.96 (2H, m), 7.23 (1H, d, J=8.8 Hz), 7.14 (1H, d, J=1.0 Hz), 7.00 (1H, d, J=1.0 Hz), 6.51 (1H, s), 4.38-4.17 (1H, br m), 3.84 (3H, s), 3.77-3.62 (1H, br m), 3.45-3.29 (3H, br m), 2.95 (2H, s), 2.32 (3H, s), 2.11-1.72 (4H, br m), 1.03-0.98 (2H, m), 0.89-0.85 (2H, m); MS [M+Na]$^+$=588.

Example 24

5-{1'-[(3-Chloro-1-cyclopropyl-4-methoxy-1H-indol-6-yl)carbonyl]-4-oxo-spiro[chroman-2,4'-piperidin]-6-yl}nicotinic acid sodium salt

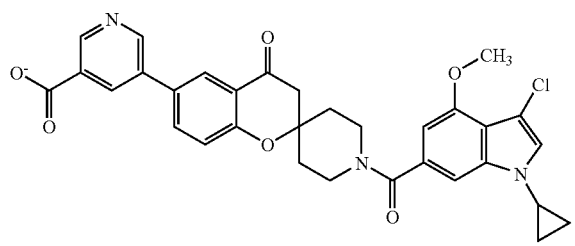

According to the methods of Example 18 and Example 9, the intended compound was obtained as a colorless amorphous substance, but using 3-chloro-1-cyclopropyl-4-methoxy-1H-indole-6-carboxylic acid in place of 1-cyclopropyl-4-(2-hydroxyethoxy)-1H-indole-6-carboxylic acid, and using 5-(4-oxo-spiro[chroman-2,4'-piperidin]-6-yl)nicotinic acid methyl ester hydrochloride in place of 3-(4-oxo-spiro[chroman-2,4'-piperidin]-6-yl)benzoic acid methyl ester hydrochloride. $^1$H-NMR (400 MHz, DMSO-d$_6$) δ: 8.90 (1H, d, J=2.0 Hz), 8.74 (1H, d, J=2.4 Hz), 8.28 (1H, dd, J=2.4, 2.0 Hz), 7.99-7.96 (2H, m), 7.44 (1H, s), 7.25-7.22 (2H, m), 6.62 (1H, s), 4.36-4.16 (1H, br m), 3.71-3.54 (1H, br m), 3.52-3.29 (3H, br m), 3.86 (3H, s), 2.95 (2H, s), 2.15-1.74 (4H, br m), 1.07-0.92 (4H, br m); MS [M+Na]$^+$=608.

Example 25

1'-[(4-Acetyl-7-methoxy-1-benzofuran-2-yl)carbonyl]-6-(1H-tetrazol-5-yl)spiro[chroman-2,4'-piperidin]-4-one

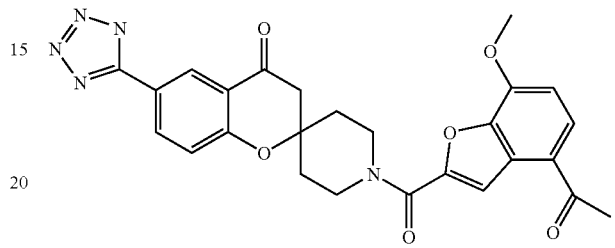

The title compound was obtained as a colorless amorphous substance, according to the method of Example 8 but using 4-acetyl-7-methoxy-1-benzofuran-2-carboxylic acid in place of 1,4-dimethoxy-1H-indole-6-carboxylic acid. $^1$H-NMR (400 MHz, DMSO-d$_6$) δ: 8.41 (1H, d, J=2.2 Hz), 8.23 (1H, dd, J=8.5, 2.2 Hz), 8.01 (1H, d, J=8.5 Hz), 7.75 (1H, s), 7.36 (1H, d, J=8.5 Hz), 7.13 (1H, d, J=8.5 Hz), 4.30-4.00 (2H, br m), 4.02 (3H, s), 4.00-3.70 (2H, br m), 2.98 (2H, s), 2.59 (3H, s), 2.10-1.98 (2H, m), 1.91-1.75 (2H, m); MS [M+H]$^+$=502.

Example 26

1'-[(1-Ethyl-3-methyl-1H-thieno[2,3-c]pyrazol-5-yl)carbonyl]-6-(1H-tetrazol-5-yl)spiro[chroman-2,4'-piperidin]-4-one

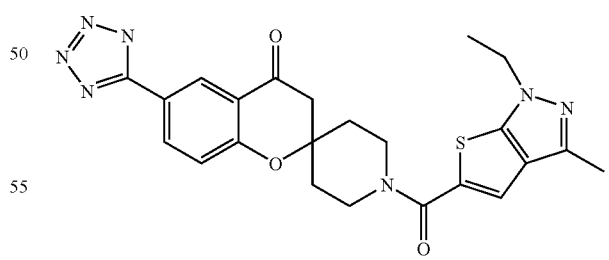

The title compound was obtained as a pale yellow amorphous substance, according to the method of Example 8, but using 1-ethyl-3-methyl-1H-thieno[2,3-c]pyrazol-5-carboxylic acid in place of 1,4-dimethoxy-1H-indole-6-carboxylic acid. $^1$H-NMR (400 MHz, DMSO-d$_6$) δ: 8.44 (1H, d, J=2.2 Hz), 8.26 (1H, dd, J=8.7, 2.3 Hz), 7.47 (1H, s), 7.36 (1H, d, J=8.5 Hz), 4.29-4.05 (2H, m), 4.16 (2H, q, J=7.3 Hz), 3.53-

3.38 (2H, m), 3.00 (2H, br s), 2.33 (3H, s), 2.09-1.99 (2H, m), 1.91-1.78 (2H, m), 1.37 (3H, t, J=7.3 Hz); MS [M+H]$^+$=478.

Example 27

5-{1'-[(1-Cyclopropyl-4-methoxy-3-methyl-1H-indol-6-yl)carbonyl]-4-oxo-spiro[chroman-2,4'-piperidin]-6-yl}nicotinic acid

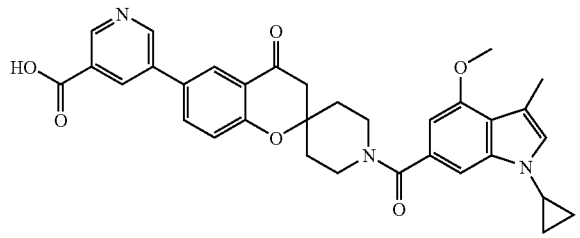

To a stirred solution of the compound of Example 23 in MeOH (25 mL) and H$_2$O (25 mL) was added 4 mL of 1N HCl aqueous at 0° C. 60 mL of MeOH was added thereto and the mixture was stirred at r.t. for 3 hours. The precipitate was filtered and dried at 60° C. in vacuo to give the title compound as a colorless solid. $^1$H-NMR (400 MHz, DMSO-d$_6$) δ: 13.56 (1H, s), 9.09 (1H, d, J=2.2 Hz), 9.03 (1H, d, J=2.2 Hz), 8.41 (1H, dd, J=2.2, 2.2 Hz), 8.07-8.03 (2H, m), 7.29-7.25 (1H, m), 7.14 (1H, d, J=1.0 Hz), 7.00 (1H, d, J=1.0 Hz), 6.51 (1H, d, J=1.0 Hz), 4.41-4.10 (1H, br m), 3.83 (3H, s), 3.51-3.41 (1H, br m), 3.51-3.26 (3H, br m), 2.96 (2H, s), 2.31 (3H, s), 2.13-1.74 (4H, br m), 1.06-0.85 (4H, m); MS [M+H]$^+$=566.

Example 28

1'-[(4-methoxy-1-methyl-1H-pyrazolo[3,4-b]pyridin-6-yl)carbonyl]-6-(1H-tetrazol-5-yl)spiro[chroman-2,4'-piperidin]-4-one

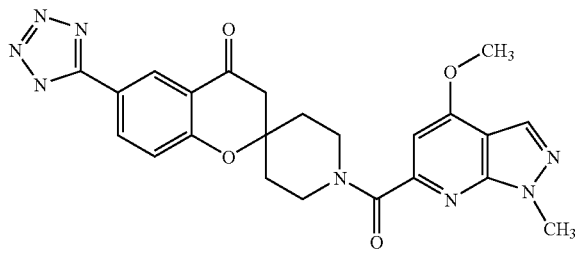

Ethyl 4-methoxy-1-methyl-1H-pyrazolo[3,4-b]pyridine-6-carboxylate (140 mg) was dissolved in THF (2.0 mL) and MeOH (2.0 mL), and aqueous 5 N sodium hydroxide solution (0.0.2 mL) was added to the solution, which was stirred at r.t. over night. The reaction mixture was added by 5 N hydrochloric acid (0.2 mL) and concentrated under reduced pressure. The residue was dissolved in DMF (3 mL) and water (1 mL), and 6-(1H-tetrazol-5-yl)spiro[chroman-2,4'-piperidin]-4-one hydrochloride (212 mg), triethylamine (0.334 mL), HOBT (110 mg) and EDCI HCl (138 mg) were added thereto. The reaction mixture was stirred at 90° C. for 3 hours, then cooled to room temperature, and water was added thereto and a colorless precipitate was then formed. The material was collected and dried under reduced pressure, washed with a mixed solvent of methanol and diethyl ether, and dried under reduced pressure to obtain the above-described compound as a colorless solid. $^1$H-NMR (400 MHz, DMSO-d$_6$) δ: 8.41 (1H, d, J=2.4 Hz), 8.23 (1H, dd, J=8.8, 2.4 Hz), 8.02 (1H, s), 7.33 (1H, d, J=8.8 Hz), 6.66 (1H, s), 4.36-4.29 (1H, br m), 3.98 (3H, s), 3.98 (3H, s), 3.34 (3H, d, J=28.5 Hz), 2.98 (2H, s), 2.12-2.04 (1H, m), 1.94-1.82 (2H, m), 1.79-1.70 (1H, br m); MS [M+H]$^+$=475.

Example 29

N-carbamoylmethyl-1'-[(1-cyclopropyl-4-ethoxy-1H-indol-6-yl)carbonyl]-4-oxo-spiro[chroman-2,4'-piperidine]-6-carboxamide

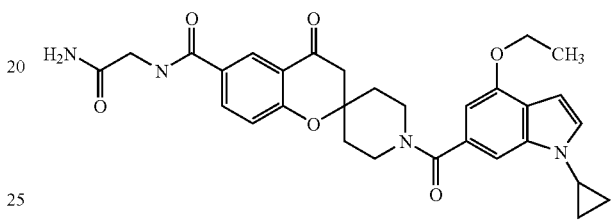

N-Carbamoylmethyl-4-oxospiro[chroman-2,4'-piperidine]-6-carboxamide hydrochloride (389 mg), 1-cyclopropyl-4-ethoxy-1H-indole-6-carboxylic acid (245 mg), WSC hydrochloride (230 mg), HOBT (183 mg) and triethylamine (0.209 mL) were suspended in DMF (8 mL), and the mixture was stirred at 80° C. for 1.5 hours. The reaction mixture was allowed to cool to room temperature, diluted with ethyl acetate, and washed successively with water, 1 N hydrochloric acid, aqueous saturated sodium bicarbonate and saturated saline water. The organic layer was dried over sodium sulfate, filtered, concentrated, and purified through silica gel column chromatography (chloroform/methanol) to afford the title compound as a colorless amorphous substance. $^1$H-NMR (400 MHz, DMSO-d$_6$) δ: 8.78-8.71 (1H, m), 8.32-8.30 (1H, m), 8.08 (1H, dd, J=8.7, 2.3 Hz), 7.34 (1H, s), 7.28 (1H, d, J=3.4 Hz), 7.22-7.16 (2H, m), 6.99 (1H, s), 6.56 (1H, s), 6.38 (1H, d, J=3.4 Hz), 4.27-4.15 (1H, br m), 4.15 (2H, q, J=7.0 Hz), 3.77 (2H, d, J=5.9 Hz), 3.46-3.25 (3H, br m), 3.45-3.39 (1H, m), 2.95 (2H, s), 2.09-1.75 (4H, br m), 1.38 (3H, t, J=7.0 Hz), 1.08-1.01 (2H, m), 0.95-0.90 (2H, m); MS [M+H]$^+$=545.

Example 30

1'-[(3-chloro-1-cyclopropyl-7-ethoxy-1H-indol-5-yl)carbonyl]-6-(1H-tetrazol-5-yl)spiro[chroman-2,4'-piperidin]-4-one

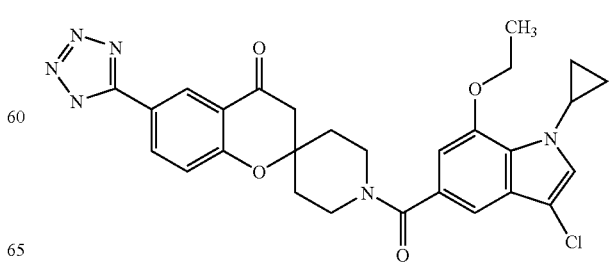

The intended compound was obtained as a colorless solid according to the methods described in Example 28, but using ethyl 3-chloro-1-cyclopropyl-7-ethoxy-1H-indole-5-carboxylate in place of ethyl 4-methoxy-1-methyl-1H-pyrazolo[3,4-b]pyridine-6-carboxylate. ¹H-NMR (400 MHz, DMSO-d₆) δ: 8.42 (1H, d, J=2.4 Hz), 8.23 (1H, dd, J=8.8, 2.4 Hz), 7.50 (1H, s), 7.33 (1H, d, J=8.8 Hz), 7.06 (1H, d, J=1.2 Hz), 6.75 (1H, s), 4.21-4.16 (1H, br m), 4.17 (2H, q, J=7.0 Hz), 3.79-3.72 (1H, m), 3.48-3.26 (3H, br m), 2.98 (2H, s), 2.07-1.76 (4H, br m), 1.42 (3H, t, J=7.0 Hz), 1.09-0.94 (4H, m); MS [M+H]⁺=547, 549.

Example 31

1'-[(3-cyclopropyl-7-ethoxy-1,2-benzisoxazol-5-yl)carbonyl]-6-(1H-tetrazol-5-yl)spiro[chroman-2,4'-piperidin]-4-one

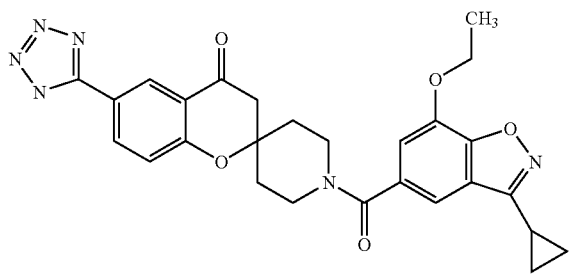

The intended compound was obtained as a colorless solid according to the method described in Example 28, but using methyl 3-cyclopropyl-7-ethoxy-1,2-benzisoxazole-5-carboxylate in place of ethyl 4-methoxy-1-methyl-1H-pyrazolo[3,4-b]pyridine-6-carboxylate. ¹H-NMR (400 MHz, DMSO-d₆) δ: 8.42 (1H, d, J=2.4 Hz), 8.24 (1H, dd, J=8.7, 2.3 Hz), 7.45 (1H, d, J=1.0 Hz), 7.33 (1H, d, J=8.8 Hz), 7.18 (1H, d, J=1.0 Hz), 4.28-4.26 (1H, br m), 4.27 (2H, q, J=7.0 Hz), 3.62-3.17 (3H, br m), 2.98 (2H, s), 2.41-2.33 (1H, m), 2.15-1.74 (4H, br m), 1.40 (3H, t, J=7.0 Hz), 1.18-1.06 (4H, m); MS [M+H]⁺=515.

Example 32

1'-[(2-cyclopropyl-7-ethoxy-1,3-benzoxazol-5-yl)carbonyl]-6-(1H-tetrazol-5-yl)spiro[chroman-2,4'-piperidin]-4-one

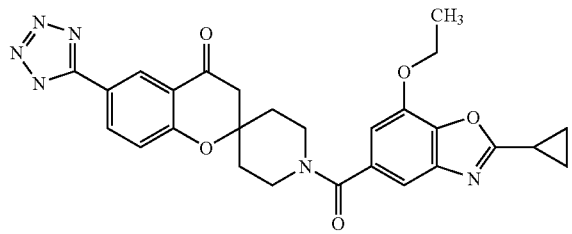

The intended compound was obtained as a colorless solid according to the methods described in Example 8, but using 2-cyclopropyl-7-ethoxy-1,3-benzoxazole-5-carboxylic acid in place of 1,4-dimethoxy-1H-indole-6-carboxylic acid. ¹H-NMR (400 MHz, DMSO-d₆) δ: 8.42 (1H, d, J=2.2 Hz), 8.23 (1H, dd, J=8.5, 2.2 Hz), 7.33 (1H, d, J=8.5 Hz), 7.20 (1H, d, J=1.2 Hz), 6.95 (1H, d, J=1.2 Hz), 4.37-4.22 (1H, br m), 4.25 (2H, q, J=7.0 Hz), 3.61-3.20 (3H, br m), 2.97 (2H, s), 2.32-2.25 (1H, m), 2.14-1.75 (4H, br m), 1.38 (3H, t, J=7.0 Hz), 1.20-1.08 (4H, m); MS [M+H]⁺=515.

Example 33

1-cyclopropyl-4-ethoxy-6-{[4-oxo-6-(1H-tetrazol-5-yl)spiro[chroman-2,4'-piperidin]-1'-yl]carbonyl}-1H-indole-3-carboxamide

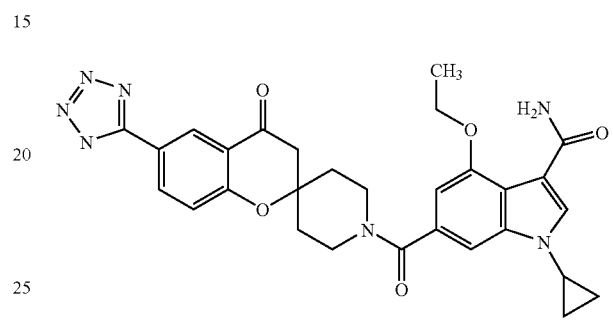

The intended compound was obtained as a colorless solid according to the methods described in Example 8, but using 3-(carbamoyl)-1-cyclopropyl-4-ethoxy-1H-indole-6-carboxylic acid in place of 1,4-dimethoxy-1H-indole-6-carboxylic acid. ¹H-NMR (400 MHz, DMSO-d₆) δ: 8.41 (1H, d, J=2.4 Hz), 8.23 (2H, dd, J=8.8, 2.4 Hz), 7.86 (1H, s), 7.34-7.28 (2H, m), 7.18 (1H, s), 6.78 (1H, s), 4.31-4.23 (1H, br m), 4.26 (2H, q, J=7.0 Hz), 3.80-3.14 (4H, m), 2.98 (2H, s), 2.18-1.74 (4H, br m), 1.41 (3H, t, J=7.0 Hz), 1.09-0.98 (4H, m); MS [M+H]⁺=556.

Example 34

N-carbamoylmethyl-1'-[(1-cyclopropyl-4-ethoxy-3-methyl-1H-indol-6-yl)carbonyl]-4-oxospiro[chroman-2,4'-piperidine]-6-carboxamide

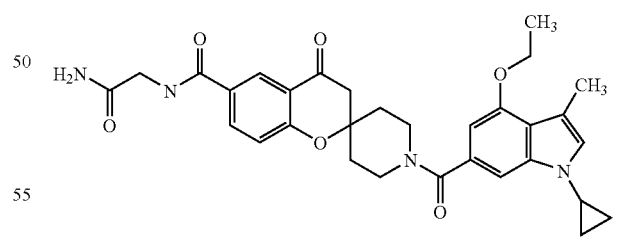

The title compound was obtained as a colorless amorphous substance according to the methods of Example 29 but using 1-cyclopropyl-4-ethoxy-3-methyl-1H-indole-6-carboxylic acid in place of 1-cyclopropyl-4-ethoxy-1H-indole-6-carboxylic acid. ¹H-NMR (400 MHz, DMSO-d₆) δ: 8.76-8.72 (1H, m), 8.32-8.30 (1H, m), 8.08 (1H, dd, J=8.8, 2.3 Hz), 7.34 (1H, s), 7.18 (1H, d, J=8.8 Hz), 7.11 (1H, d, J=1.0 Hz), 7.00-6.97 (2H, br m), 6.47 (1H, s), 4.28-4.16 (1H, br m), 4.08 (2H, q, J=6.9 Hz), 3.77 (2H, d, J=5.9 Hz), 3.72-3.24 (4H, br m), 2.94 (2H, s), 2.05-1.73 (4H, br m), 2.33 (3H, s), 1.37 (3H, t, J=6.9 Hz), 1.01-0.87 (4H, m); MS [M+H]⁺=559.

Example 35

N-carbamoylmethyl-1'-[(1,4-diethoxy-1H-indol-6-yl)carbonyl]-4-oxospiro[chroman-2,4'-piperidine]-6-carboxamide

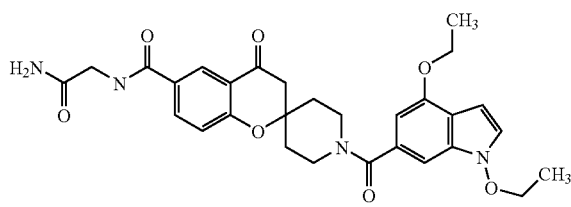

The title compound was obtained as a colorless amorphous substance according to the methods described in Example 29, but using 1,4-diethoxy-1H-indole-6-carboxylic acid in place of 1-cyclopropyl-4-ethoxy-1H-indole-6-carboxylic acid. ¹H-NMR (400 MHz, DMSO-d₆) δ: 8.74 (1H, t, J=6.0 Hz), 8.31 (1H, d, J=2.2 Hz), 8.08 (1H, dd, J=8.7, 2.2 Hz), 7.58 (1H, d, J=3.4 Hz), 7.33 (1H, s), 7.18 (1H, d, J=8.7 Hz), 7.07 (1H, s), 6.98 (1H, s), 6.54 (1H, s), 6.35 (1H, d, J=3.4 Hz), 4.33-4.14 (1H, br m), 4.28 (2H, q, J=7.0 Hz), 4.16 (2H, q, J=7.0 Hz), 3.77 (2H, d, J=6.0 Hz), 3.37-3.29 (3H, br m), 2.94 (2H, s), 2.04-1.76 (4H, br m), 1.39 (3H, t, J=7.0 Hz), 1.29 (3H, t, J=7.0 Hz); MS [M+H]⁺=549.

Example 36

1'-{[1-cyclopropyl-4-(2-hydroxyethoxy-1H-indol-6-yl]carbonyl}-6-(1H-tetrazol-5-yl)spiro[chroman-2,4'-piperidin]-4-one

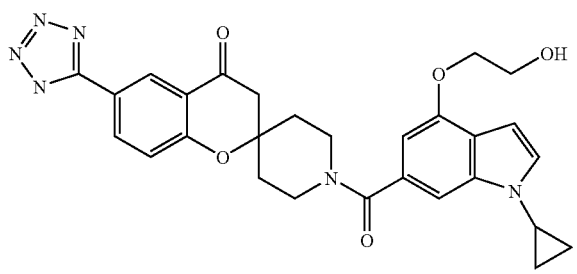

According to the methods of Example 8, the intended compound was obtained as a colorless solid, but using 1-cyclopropyl-4-(2-hydroxyethoxy)-1H-indole-6-carboxylic acid in place of 1,4-dimethoxy-1H-indole-6-carboxylic acid. ¹H-NMR (400 MHz, DMSO-d₆) δ: 8.42 (1H, d, J=2.4 Hz), 8.23 (1H, dd, J=8.7, 2.4 Hz), 7.33 (1H, d, J=8.7 Hz), 7.29 (1H, d, J=3.2 Hz), 7.21 (1H, s), 6.58 (1H, s), 6.42 (1H, d, J=3.2 Hz), 4.90-4.82 (1H, br m), 4.30-4.20 (1H, br m), 4.10 (2H, t, J=5.0 Hz), 3.79-3.74 (2H, br m), 3.48-3.26 (4H, br m), 2.99 (2H, s), 2.07-1.76 (4H, br m), 1.07-0.88 (4H, m); MS [M+H]⁺=529.

Example 37

1-cyclopropyl-4-ethoxy-N-methyl-6-{[4-oxo-6-(1H-tetrazol-5-yl)spiro[chroman-2,4'-piperidin]-1'-yl]carbonyl}-1H-indole-3-carboxamide

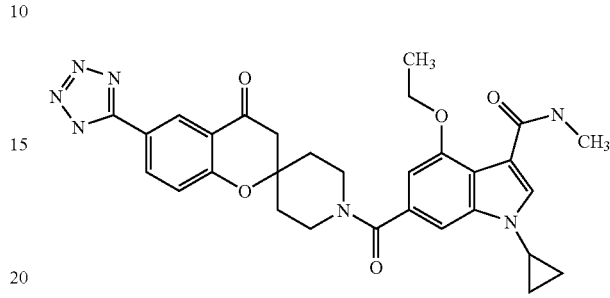

The title compound was obtained as a colorless solid according to the method shown in Example 28, but using ethyl 1-cyclopropyl-4-ethoxy-3-(methylcarbamoyl)-1H-indole-6-carboxylate instead of ethyl 4-methoxy-1-methyl-1H-pyrazolo[3,4-b]pyridine-6-carboxylate. ¹H-NMR (400 MHz, DMSO-d₆) δ: 8.63-8.58 (1H, br m), 8.42 (1H, s), 8.24 (1H, d, J=8.8 Hz), 7.84 (1H, s), 7.36-7.31 (2H, br m), 6.77 (1H, s), 4.55-4.04 (1H, br m), 4.25 (2H, q, J=6.9 Hz), 3.56-3.29 (4H, br m), 2.99 (2H, s), 2.80 (3H, d, J=4.6 Hz), 2.12-1.77 (4H, br m), 1.47 (3H, t, J=6.9 Hz), 1.16-0.96 (4H, m); MS [M+H]⁺=570.

Example 38 methyl 3-(1'-{[3-carbamoyl-1-cyclopropyl-4-ethoxy-1H-indol-6-yl]carbonyl}-4-oxospiro[chroman-2,4'-piperidin]-6-yl)benzoate

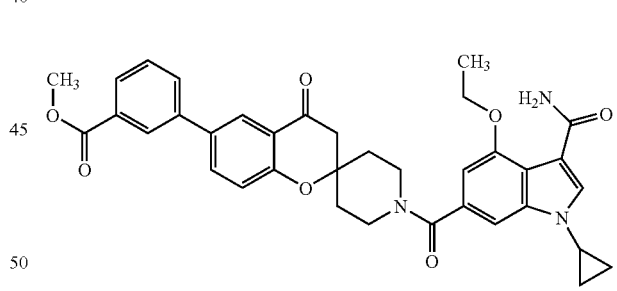

Triethylamine (0.22 mL) was added to a solution of 3-carbamoyl-1-cyclopropyl-4-ethoxy-1H-indole-6-carboxylic acid (229 mg), 3-(4-oxo-spiro[chroman-2,4'-piperidin]-6-yl) benzoic acid methyl ester hydrochloride (306 mg), WSC hydrochloride (166 mg) and HOBT (133 mg) in DMF (4 mL), and the mixture was stirred at 60° C. for 1 hour. After cooling to room temperature, the reaction mixture was diluted with ethyl acetate, then washed successively with water, aqueous saturated sodium bicarbonate and saturated saline water. The organic layer was dried over sodium sulfate, filtered, concentrated, and purified through silica gel column chromatography (chloroform/methanol) to obtain the intended ester derivative as a colorless amorphous substance. ¹H-NMR (400 MHz, CDCl₃) δ: 8.71 (1H, s), 8.25 (1H, dd, J=1.5, 1.5 Hz), 8.14 (1H, d, J=2.4 Hz), 8.04-8.00 (2H, m), 7.83-7.74 (2H, m), 7.51 (1H, dd, J=7.8, 7.8 Hz), 7.37 (1H, d, J=1.5 Hz), 7.13 (1H, d, J=7.8 Hz), 6.74 (1H, d, J=1.5 Hz), 5.54 (1H, s), 4.62-4.41 (1H, br m), 4.29 (2H, q, J=7.0 Hz), 3.95 (3H, s), 2.28-1.71 (4H, br m), 3.88-3.32 (4H, br m), 2.82 (2H, s), 1.55 (3H, t, J=7.0 Hz), 1.16-1.00 (4H, m); MS [M+H]$^+$=622.

Example 39

3-(1'-{[3-carbamoyl-1-cyclopropyl-4-ethoxy-1H-indol-6-yl]carbonyl}-4-oxospiro[chroman-2,4'-piperidin]-6-yl)benzoic acid

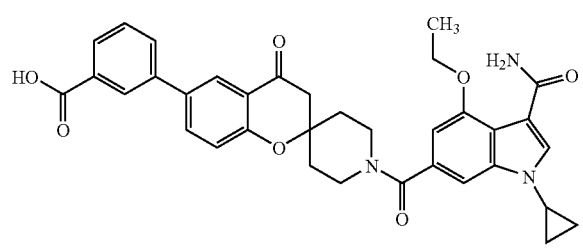

Aqueous 5 N sodium hydroxide solution (0.32 mL) was added to a methanolic (10 mL) solution of the ester compound (523 mg), and the mixture was stirred at 60° C. for 4 hours. The organic solvent was evaporated, and the residue was diluted with water. Aqueous 5N hydrochloric acid solution (330 µl) was added thereto at room temperature, and the mixture was extracted with a mixed solvent of chloroform and methanol, and dried over sodium sulfate. The organic layer was filtered and concentrated to afford the title compound as a colorless solid. $^1$H-NMR (400 MHz, DMSO-d$_6$) δ: 8.22 (1H, s), 8.15-8.12 (1H, br m), 7.99-7.85 (5H, m), 7.58 (1H, dd, J=7.7, 7.7 Hz), 7.34 (1H, s), 7.24-7.16 (2H, m), 6.79 (1H, s), 4.32-4.24 (2H, br m), 4.27 (1H, q, J=6.8 Hz), 3.72-3.19 (4H, br m), 2.95 (2H, s), 2.01-1.77 (4H, br m), 1.41 (3H, t, J=6.8 Hz), 1.11-0.94 (4H, m); MS [M+H]$^+$=608.

Example 40

1-cyclopropyl-4-ethoxy-6-{[4-oxo-6-(1H-pyrazol-4-yl)spiro[chroman-2,4'-piperidin]-1'-yl]carbonyl}-1H-indole-3-carboxylic acid

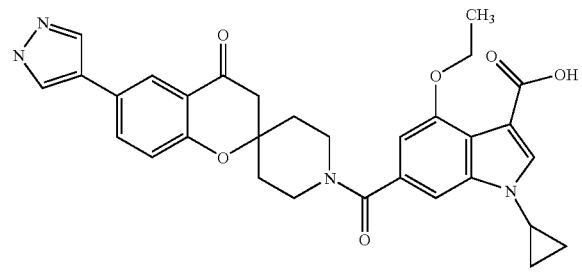

Triethylamine (0.21 mL) was added to a solution of 3-(tert-butoxycarbonyl)-1-cyclopropyl-4-ethoxy-1H-indole-6-carboxylic acid (177 mg), 6-(1H-pyrazol-4-yl)spiro[chroman-2,4'-piperidin]-4-one hydrochloride (156 mg), WSC hydrochloride (106 mg) and HOBT (85 mg) in DMF (4 mL) and the mixture was stirred at 90° C. for 1 hour. After cooling to room temperature, the mixture was diluted with ethyl acetate, then washed with water, 1N hydrochloric acid solution, aqueous saturated sodium bicarbonate and saturated saline in this order, and dried over sodium sulfate. The solution was filtered, concentrated, and purified through silica gel column chromatography (chloroform/methanol) to give the methyl ester of the title compound as a colorless amorphous substance. TFA (3 ml) was added to the solution of this ester in chloroform (10 ml) at room temperature and stirred for 3 h. The solvent was evaporated and the residue was crystallized from a mixed solvent of methanol and ether to give title compound as a colorless solid. $^1$H-NMR (400 MHz, DMSO-d$_6$) δ: 8.03 (2H, s), 7.94 (1H, s), 7.87 (1H, d, J=2.4 Hz), 7.83 (1H, dd, J=8.5, 2.4 Hz), 7.33 (1H, d, J=1.0 Hz), 7.10 (1H, d, J=8.5 Hz), 6.79 (1H, d, J=1.0 Hz), 4.31-4.19 (1H, br m), 4.21 (2H, q, J=7.0 Hz), 3.85-3.21 (4H, br m), 2.89 (2H, s), 2.11-1.70 (4H, br m), 1.39 (3H, t, J=7.0 Hz), 1.10-1.00 (4H, m); MS [M+H]$^+$=555.

Example 41

1-cyclopropyl-4-ethoxy-6-({6-[(1-methyl-1H-pyrazol-5-yl)amino]-4-oxospiro[chroman-2,4'-piperidin]-1'-yl}carbonyl)-1H-indole-3-carboxylic acid

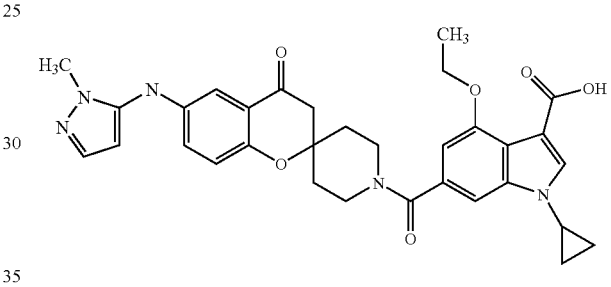

According to the methods described in Example 40 but using 6-[(1-methyl-1H-pyrazol-5-yl)amino]spiro[chroman-2,4'-piperidin]-4-one hydrochloride in place of 6-(1H-pyrazol-4-yl)spiro[chroman-2,4'-piperidin]-4-one hydrochloride, the intended compound was obtained as a colorless solid. $^1$H-NMR (400 MHz, DMSO-d$_6$) δ: 7.97 (1H, br s), 7.94 (1H, s), 7.36 (1H, d, J=2.0 Hz), 7.32 (1H, d, J=1.2 Hz), 7.18-7.14 (2H, m), 7.01-6.98 (1H, m), 6.78 (1H, d, J=1.2 Hz), 5.91 (1H, d, J=2.0 Hz), 4.35-4.15 (1H, br m), 4.21 (2H, q, J=7.0 Hz), 3.62 (3H, s), 3.62-3.19 (4H, m), 2.82 (2H, s), 2.10-1.69 (4H, br m), 1.39 (3H, t, J=7.0 Hz), 1.11-0.98 (4H, m); MS [M+H]$^+$= 584.

Example 42

4-{1'-[(1-cyclopropyl-4-methoxy-3-methyl-1H-indol-6-yl)carbonyl]-4-oxospiro[chroman-2,4'-piperidin]-6-yl}pyridine-2-carboxylic acid

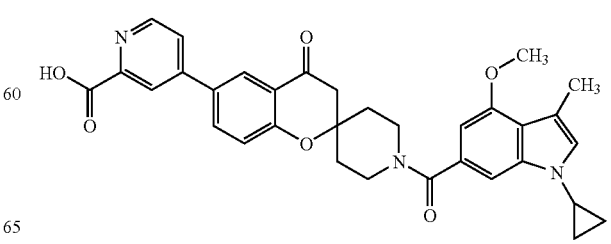

Triethylamine (0.22 mL) was added to a solution of 1-cyclopropyl-4-methoxy-3-methyl-1H-indole-6-carboxylic acid (98 mg), methyl 4-(4-oxospiro[chroman-2,4'-piperidin]-6-yl)pyridine-2-carboxylate dihydrochloride (170 mg), WSC hydrochloride (109 mg) and HOBT (74 mg) in DMF (3 mL) and the mixture was stirred at room temperature over night. The organic solvent was evaporated and the residue was purified through a silica gel column to obtain methyl ester of the intended compound as a colorless amorphous substance. Aqueous 1 N sodium hydroxide solution (1 mL) was added to a solution of the ester in methanol (3 ml) and THF (3 ml) and the mixture was stirred at room temperature for 4 hours. The mixture was concentrated, diluted with water, added by aqueous 1N hydrochloric acid solution (1 ml) at room temperature, and extracted with a mixed solvent of chloroform and methanol. The organic layer was dried over sodium sulfate, filtered, and concentrated. The residue was crystallized from a mixed solvent of hexane and ethyl acetate to afford the intended compound as a colorless solid. $^1$H-NMR (400 MHz, DMSO-$d_6$) δ: 13.27 (1H, br s), 8.72 (1H, d, J=4.9 Hz), 8.25 (1H, d, J=1.0 Hz), 8.15-8.11 (2H, m), 7.95 (1H, dd, J=4.9, 2.0 Hz), 7.29 (1H, dd, J=6.3, 2.9 Hz), 7.14 (1H, d, J=1.0 Hz), 7.00 (1H, d, J=1.0 Hz), 6.50 (1H, d, J=1.0 Hz), 4.42-4.14 (1H, br m), 3.84-3.58 (1H, br m), 3.83 (3H, s), 3.56-3.15 (3H, br m), 2.97 (2H, s), 2.31 (3H, d, J=1.0 Hz), 2.08-1.76 (4H, br m), 1.03-0.98 (2H, m), 0.90-0.84 (2H, m); MS [M+H]$^+$=566.

Example 43

5-{1'-[(1-cyclopropyl-4-methoxy-3-methyl-1H-indol-6-yl)carbonyl]-4-oxospiro[chroman-2,4'-piperidin]-6-yl}-2-methylnicotinic acid

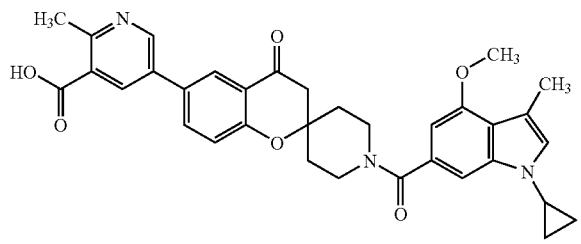

The title compound was obtained as a colorless amorphous substance in the same manner as described in Example 42, but using methyl 2-methyl-5-(4-oxospiro[chroman-2,4'-piperidin]-6-yl)nicotinate dihydrochloride instead of methyl 4-(4-oxospiro[chroman-2,4'-piperidin]-6-yl)pyridine-2-carboxylate dihydrochloride. $^1$H-NMR (400 MHz, DMSO-$d_6$) δ: 13.38 (0.8H, s), 8.89 (1.0H, d, J=2.0 Hz), 8.33 (1.0H, d, J=2.0 Hz), 8.02-7.99 (1.9H, m), 7.25 (1.0H, dd, J=6.6, 2.0 Hz), 7.14 (1.0H, d, J=1.0 Hz), 7.00 (0.9H, d, J=1.0 Hz), 6.50 (0.9H, d, J=1.0 Hz), 4.37-4.06 (1.0H, br m), 3.83 (2.8H, s), 3.83-3.59 (1.0H, br m), 3.36-3.26 (3.0H, m), 2.95 (1.8H, s), 2.73 (2.9H, s), 2.31 (3.1H, d, J=1.0 Hz), 2.12-1.76 (3.6H, m), 1.03-0.98 (1.8H, m), 0.89-0.83 (2.0H, m); MS [M+H]$^+$=580.

Example 44

6-{1'-[(1-cyclopropyl-4-methoxy-3-methyl-1H-indol-6-yl)carbonyl]-4-oxospiro[chroman-2,4'-piperidin]-6-yl}nicotinic acid

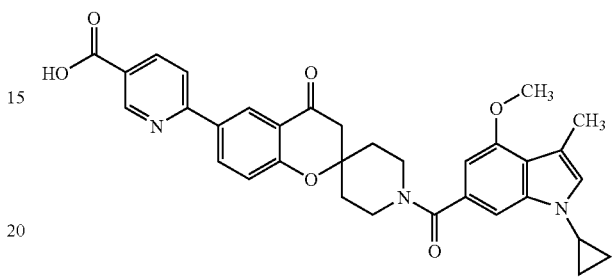

The title compound was obtained as a colorless amorphous substance in the same manner as described in Example 42, from methyl 6-(4-oxospiro[chroman-2,4'-piperidin]-6-yl)nicotinate dihydrochloride instead of methyl 4-(4-oxospiro[chroman-2,4'-piperidin]-6-yl)pyridine-2-carboxylate dihydrochloride. $^1$H-NMR (400 MHz, DMSO-$d_6$) δ: 13.37 (1H, s), 9.12-9.10 (1H, m), 8.54 (1H, d, J=2.4 Hz), 8.40 (1H, dd, J=8.8, 2.4 Hz), 8.29 (1H, dd, J=8.8, 2.4 Hz), 8.10 (1H, d, J=8.8 Hz), 7.26 (1H, d, J=8.8 Hz), 7.14 (1H, s), 7.00 (1H, d, J=1.0 Hz), 6.50 (1H, d, J=1.0 Hz), 4.44-4.09 (1H, br m), 3.83 (3H, s), 3.77-3.58 (1H, br m), 3.39-3.32 (3H, m), 2.31 (3H, s), 2.97 (2H, s), 2.10-1.77 (4H, br m), 1.03-0.98 (2H, m), 0.89-0.85 (2H, m); MS [M+H]$^+$=566.

Example 45

5-{1'-[(1-cyclopropyl-4-ethoxy-3-methyl-1H-indol-6-yl)carbonyl]-4-oxospiro[chroman-2,4'-piperidin]-6-yl}nicotinic acid

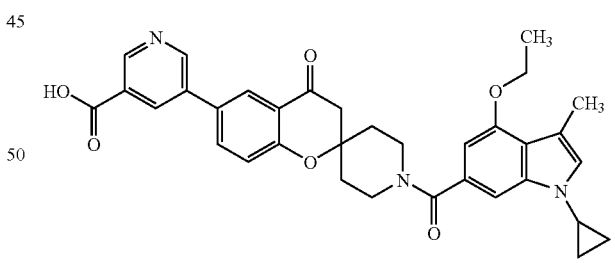

TEA (162 mg) was added to a mixture of EDCI (92 mg), HOBT (73.5 mg), 1-cyclopropyl-4-ethoxy-3-methyl-1H-indole-6-carboxylic acid (104 mg), and methyl 5-(4-oxospiro[chroman-2,4'-piperidin]-6-yl)nicotinate dihydrochloride (170 mg) and DMF (3 ml), and the mixture was stirred at r.t. for 5 hours. The mixture was evaporated and purified through SiO2 column chromatography (eluted with Hex-EtOAc, then MeOH—CHCl3) to give methyl ester of the title compound as a pale yellow solid. 1 ml of 1N NaOHaq was added to its solution in 3 ml of MeOH and 3 ml of THF, and the mixture was stirred at r.t. for 4 h. Then the mixture was neutralized with 1N HClaq and diluted with CHCl$_3$-MeOH. The mixture was dried over Na$_2$SO$_4$, filtered, and concentrated. The residue was crystallized from EtOAc-n-hexane to give the title compound as a slightly yellowish powder. $^1$H-NMR (400 MHz, DMSO-d$_6$) δ: 13.57 (1H, s), 9.08 (1H, d, J=2.0 Hz), 9.03 (1H, d, J=2.0 Hz), 8.41 (1H, dd, J=2.0, 2.0 Hz), 8.08-8.02 (2H, m), 7.26 (1H, dd, J=7.8, 1.0 Hz), 7.12 (1H, d, J=1.0 Hz), 7.00 (1H, d, J=1.0 Hz), 6.48 (1H, s), 4.36-4.14 (1H, br m), 4.08 (2H, q, J=7.0 Hz), 3.78-3.20 (4H, br m), 2.96 (2H, s), 2.33 (3H, d, J=1.0 Hz), 2.09-1.73 (4H, m), 1.37 (3H, t, J=7.0 Hz), 1.03-0.98 (2H, m), 0.89-0.85 (2H, m); MS [M+H]$^+$=580.

Example 46

4-{1'-[(1-cyclopropyl-4-ethoxy-3-methyl-1H-indol-6-yl)carbonyl]-4-oxospiro[chroman-2,4'-piperidin]-6-yl}pyridine-2-carboxylic acid

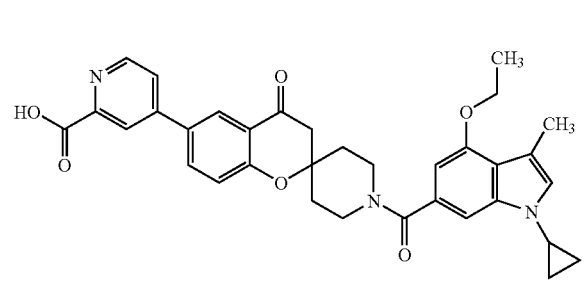

In the same manner as described in Example 42 except using 1-cyclopropyl-4-ethoxy-3-methyl-1H-indole-6-carboxylic acid and methyl 4-(4-oxospiro[chroman-2,4'-piperidin]-6-yl)pyridine-2-carboxylate dihydrochloride, the title compound was obtained as a colorless amorphous substance. $^1$H-NMR (400 MHz, DMSO-d$_6$) δ: 8.72 (1H, d, J=4.9 Hz), 8.25 (1H, d, J=1.5 Hz), 8.15-8.11 (2H, m), 7.94 (1H, dd, J=6.0, 2.0 Hz), 7.28 (1H, dd, J=6.0, 2.9 Hz), 7.12 (1H, d, J=1.0 Hz), 6.99 (1H, d, J=1.0 Hz), 6.48 (1H, s), 4.45-4.10 (1H, br m), 4.08 (2H, q, J=6.8 Hz), 3.67-3.19 (4H, m), 2.97 (2H, s), 2.32 (3H, s), 2.12-1.74 (4H, br m), 1.37 (3H, t, J=6.8 Hz), 1.03-0.98 (2H, m), 0.88-0.85 (2H, m); MS [M+H]$^+$=580.

Example 47

5-{1'-[(1-cyclopropyl-4-ethoxy-3-methyl-1H-indol-6-yl)carbonyl]-4-oxo-spiro[chroman-2,4'-piperidin]-6-yl}nicotinic acid sodium salt

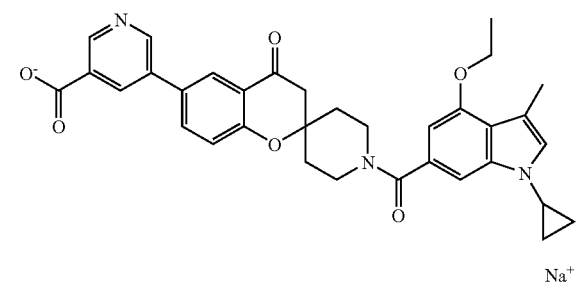

To a suspension of 138 mg of compound of Example 45 in a mixed solvent of MeOH and water (1:9) was added 1N NaOH aq (1.5 eq) and the mixture was purified on ODS column (eluent: H$_2$O-MeOH gradient system) to give the title compound as a slightly yellowish amorphous substance. $^1$H-NMR (400 MHz, DMSO-d$_6$) δ: 8.90 (1H, d, J=2.0 Hz), 8.74 (1H, d, J=2.0 Hz), 8.28 (1H, dd, J=2.0, 1.1 Hz), 7.97-7.92 (2H, m), 7.21 (1H, d, J=8.8 Hz), 7.10 (1H, d, J=1.0 Hz), 6.97 (1H, d, J=1.0 Hz), 6.46 (1H, s), 4.29-4.15 (1H, br m), 4.06 (2H, q, J=7.0 Hz), 3.77-3.55 (1H, br m), 3.39 (3H, s), 2.92 (2H, s), 2.30 (3H, s), 2.07-1.71 (4H, br m), 1.35 (3H, t, J=6.9 Hz), 1.01-0.95 (2H, m), 0.87-0.82 (2H, m); MS [M+H]$^+$=580.

Example 48

5-{1'-[(1,4-dimethoxy-3-methyl-1H-indol-6-yl)carbonyl]-4-oxospiro[chroman-2,4'-piperidin]-6-yl}nicotinic acid

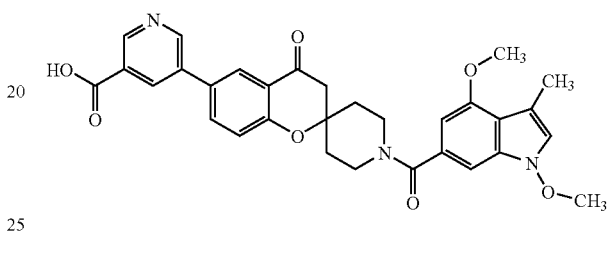

The title compound was obtained as a colorless amorphous substance in the same manner as described in Example 42 but using 1,4-dimethoxy-3-methyl-1H-indole-6-carboxylic acid and methyl 5-(4-oxospiro[chroman-2,4'-piperidin]-6-yl)pyridine-3-carboxylate dihydrochloride. $^1$H-NMR (400 MHz, DMSO-d$_6$) δ: 9.04 (1H, d, J=2.2 Hz), 8.99 (1H, d, J=2.2 Hz), 8.38 (1H, dd, J=2.2, 2.2 Hz), 8.04-8.00 (2H, m), 7.32-7.30 (1H, br m), 7.25-7.22 (1H, m), 6.99 (1H, d, J=1.0 Hz), 6.48 (1H, d, J=1.0 Hz), 4.37-4.10 (1H, br m), 3.96 (3H, s), 3.83 (3H, s), 3.73-3.09 (3H, br m), 2.93 (2H, s), 2.30 (3H, d, J=1.0 Hz), 2.10-1.72 (4H, br m); MS [M+H]$^+$=556.

Example 49

6-(5-bromopyridin-3-yl)-1'-[(1-cyclopropyl-4-methoxy-3-methyl-1H-indol-6-yl)carbonyl]spiro[chroman-2,4'-piperidin]-4-one

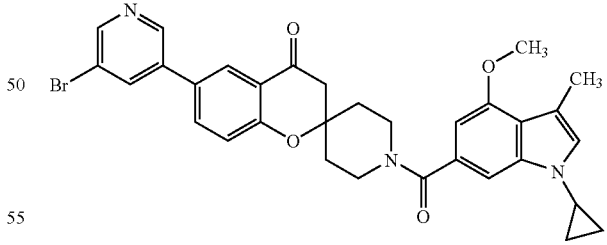

Triethylamine (0.33 mL) was added to a DMF (7.5 mL) solution of 1-cyclopropyl-4-methoxy-3-methyl-1H-indole-6-carboxylic acid (147 mg), 6-(5-bromo-3-pyridinyl)spiro-[chroman-2,4'-piperidin]-4-one dihydrochloride (268 mg), WSC hydrochloride (164 mg) and HOBT (110 mg), and stirred at r.t. for 5 h. This reaction mixture was diluted with ethyl acetate, then washed with water, aqueous saturated sodium bicarbonate and saturated saline water in that order, and dried with sodium sulfate. This was filtered, concentrated, and purified through silica gel column chromatography (hexane/ethyl acetate) to obtain the title compound as a colorless amorphous substance. $^{1}$H-NMR (400 MHz, DMSO-$d_6$) δ: 8.86 (1H, d, J=2.0 Hz), 8.66 (1H, d, J=2.0 Hz), 8.36 (1H, t, J=2.0 Hz), 8.05-7.99 (2H, m), 7.24 (1H, d, J=8.6 Hz), 7.13 (1H, s), 7.00 (1H, s), 6.50 (1H, s), 4.40-4.08 (1H, br m), 3.83 (3H, s), 3.78-3.22 (4H, br m), 2.94 (2H, s), 2.31 (3H, s), 2.04-1.75 (4H, br m), 1.03-0.97 (2H, m), 0.89-0.84 (2H, m); MS [M+H]$^+$=600, 602.

Example 50

Methyl 5-{1'-[(1-cyclopropyl-4-methoxy-3-methyl-1H-indol-6-yl)carbonyl]-4-oxospiro[chroman-2,4'-piperidin]-6-yl}nicotinate

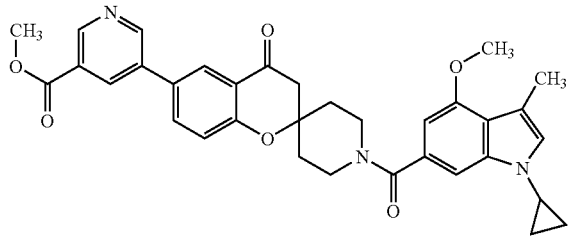

The title compound was obtained as a colorless amorphous substance in the same manner as described in Example 49 using methyl 5-[4-oxospiro(chroman-2,4'-piperidin)-6-yl]pyridine-3-carboxylate dihydrochloride in place of 6-(5-bromo-3-pyridinyl)spiro[chroman-2,4'-piperidin]-4-one dihydrochloride. $^{1}$H-NMR (400 MHz, DMSO-$d_6$) δ: 9.12 (1H, d, J=2.0 Hz), 9.05 (1H, d, J=2.0 Hz), 8.44 (1H, dd, J=2.0, 2.0 Hz), 8.08-8.05 (2H, m), 7.27 (1H, d, J=8.8 Hz), 7.14 (1H, s), 7.00 (1H, d, J=1.0 Hz), 6.51 (1H, d, J=1.0 Hz), 4.34-4.16 (1H, br m), 3.92 (3H, s), 3.84 (3H, s), 3.81-3.21 (4H, br m), 2.96 (2H, s), 2.31 (3H, s), 2.08-1.76 (4H, br m), 1.03-0.98 (2H, m), 0.89-0.84 (2H, m); MS [M+H]$^+$=580.

Example 51

1'-[(1-cyclopropyl-4-methoxy-1H-indol-6-yl)carbonyl]-6-(5-oxo-4,5-dihydro-1H-1,2,4-triazol-3-yl)spiro[chroman-2,4'-piperidin]-4-one

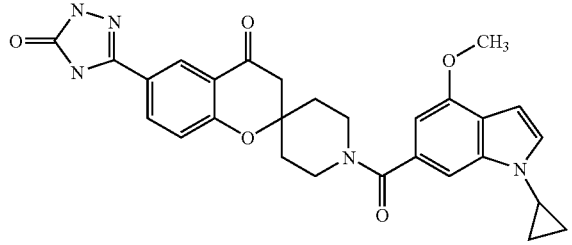

Et3N (209 uL), HOBT (91.2 mg) and WSC (115 mg) were added to a suspension of 1-cyclopropyl-4-(methyloxy)-1H-indole-6-carboxylic acid (116 mg) and 6-(5-oxo-4,5-dihydro-1H-1,2,4-triazol-3-yl)spiro[chroman-2,4'-piperidin]-4-one hydrochloride (202 mg) in DMF (3 mL), and the mixture was stirred overnight at 50° C. Water was added to the reaction mixture, and the formed solid was collected by filtration. The solid was purified by silica gel column chromatography (CHCl$_3$/MeOH) to obtain the intended compound as colorless foam. $^{1}$H-NMR (400 MHz, DMSO-$d_6$) δ: 8.06 (1H, d, J=2.3 Hz), 8.00 (1H, dd, J=8.7, 2.3 Hz), 7.29 (1H, d, J=3.2 Hz), 7.26 (1H, d, J=8.7 Hz), 7.24-7.21 (3H, m), 6.58 (1H, d, J=1.0 Hz), 6.40 (1H, dd, J=3.2, 1.0 Hz), 4.44-4.08 (1H, br m), 3.87 (3H, s), 3.80-3.25 (4H, m), 2.97 (2H, s), 2.10-1.70 (4H, m), 1.09-1.01 (2H, m), 0.96-0.89 (2H, m); MS [M+H]$^+$=514.

Example 52

N-carbamoylmethyl-1'-[(1-cyclopropyl-4-methoxy-1H-indol-6-yl)carbonyl]-4-oxo-spiro[chroman-2,4'-piperidine]-6-carboxamide

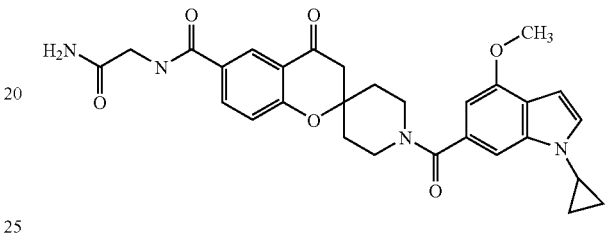

Et3N (209 uL), HOBT (91.2 mg) and WSC (115 mg) were added to a suspension of 1-cyclopropyl-4-(methyloxy)-1H-indole-6-carboxylic acid (145 mg) and N-carbamoylmethyl-4-oxo-spiro[chroman-2,4'-piperidine]-6-carboxamide hydrochloride (354 mg) in DMF (3 mL), and the mixture was stirred overnight at 50° C. After cooled to room temperature, the mixture was diluted with water, and the formed solid was collected by filtration. The solid was dried and purified on silica gel preparative TLC (development: CHCl3/MeOH) to obtain the intended compound as colorless foam. $^{1}$H-NMR (400 MHz, DMSO-$d_6$) δ: 8.84-8.72 (1H, m), 8.80-8.62 (1H, m), 8.33-8.29 (1H, m), 8.08 (1H, dd, J=8.7, 2.3 Hz), 7.35 (1H, s), 7.28 (1H, d, J=3.2 Hz), 7.23-7.16 (2H, m), 6.99 (1H, s), 6.58 (1H, d, J=1.0 Hz), 6.39 (1H, dd, J=3.2, 0.7 Hz), 4.40-4.02 (2H, br m), 3.87 (3H, s), 3.80-3.76 (2H, br m), 3.48-3.25 (4H, m), 2.98 (2H, s), 2.06-1.56 (2H, m), 1.09-1.01 (2H, m), 0.95-0.89 (2H, m); MS [M+H]$^+$=531.

Example 53

Sodium 5-{1'-[(1-cyclopropyl-4-ethoxy-3-methyl-1H-indol-6-yl)carbonyl]-4-oxospiro[chroman-2,4'-piperidin]-6-yl}-2-methylnicotinate

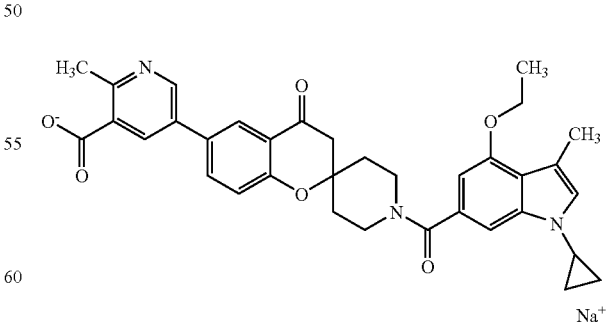

The intended compound was obtained as a pale yellow foam according to the methods of Example 18 and Example 9 but using 1-cyclopropyl-4-ethoxy-1H-indole-6-carboxylic acid in place of 1-cyclopropyl-4-(2-hydroxyethoxy)-1H-indole-6-carboxylic acid, and using methyl 2-methyl-5-(4-oxo-spiro[chroman-2,4'-piperidin]-6-yl)-3-pyridinecarboxylate hydrochloride in place of 3-(4-oxo-spiro[chroman-2,4'-piperidin]-6-yl)benzoic acid methyl ester hydrochloride. $^1$H-NMR (400 MHz, DMSO-d$_6$) δ: 8.52 (1H, d, J=2.7 Hz), 7.98 (1H, d, J=2.7 Hz), 7.93-7.89 (2H, m), 7.23-7.19 (1H, m), 7.12 (1H, d, J=1.0 Hz), 6.99 (1H, d, J=1.0 Hz), 6.48 (1H, d, J=1.0 Hz), 4.38-4.11 (1H, br m), 4.08 (2H, q, J=7.0 Hz), 3.77-3.18 (4H, br m), 2.93 (2H, s), 2.63 (3H, s), 2.32 (3H, d, J=1.0 Hz), 2.10-1.88 (2H, br m), 1.85-1.73 (2H, br m), 1.37 (3H, t, J=7.0 Hz), 1.03-0.97 (2H, m), 0.89-0.84 (2H, m); MS [M+H]$^+$=594.

Example 54

1'-[(1-ethyl-4-morpholin-4-yl-1H-indol-6-yl)carbonyl]-6-(1H-tetrazol-5-yl)spiro[chroman-2,4'-piperidin]-4-one

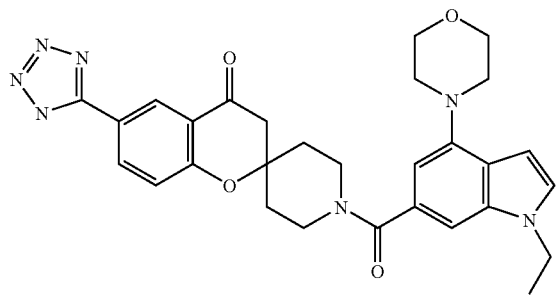

According to the methods of Example 8 but using 1-ethyl-4-morpholino-1H-indole-6-carboxylic acid in place of 1,4-dimethoxy-1H-indole-6-carboxylic acid, the intended compound was obtained as a slightly yellowish substance. $^1$H-NMR (400 MHz, DMSO-d$_6$) δ: 8.42 (1H, d, J=2.2 Hz), 8.23 (1H, dd, J=8.5, 2.2 Hz), 7.40 (1H, d, J=3.2 Hz), 7.34 (1H, d, J=8.5 Hz), 7.19 (1H, s), 6.49 (1H, s), 6.45 (1H, d, J=3.2 Hz), 4.35-4.05 (1H, br s), 4.19 (2H, q, J=7.3 Hz), 3.83-3.76 (4H, m), 3.6-3.2 (3H, br m), 3.14-3.09 (4H, br m), 2.99 (2H, s), 2.10-1.74 (4H, m), 1.33 (3H, t, J=7.3 Hz); MS [M+H]$^+$=542.

Example 55

1'-[(1-cyclopropyl-4-methoxy-3-methyl-1H-indol-6-yl)carbonyl]-6-(1H-tetrazol-5-yl)spiro[chroman-2,4'-piperidin]-4-one

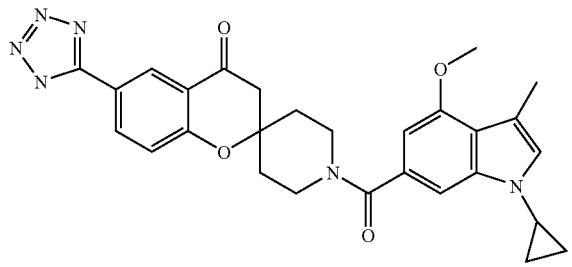

The intended compound was obtained as a slightly yellowish substance, according to the method of Example 8 but using 1-cyclopropyl-3-methyl-4-methoxy-1H-indole-6-carboxylic acid in place of 1,4-dimethoxy-1H-indole-6-carboxylic acid. $^1$H-NMR (400 MHz, DMSO-d$_6$) δ: 8.42 (1H, d, J=2.0 Hz), 8.24 (1H, dd, J=8.8, 2.0 Hz), 7.35 (1H, d, J=8.8 Hz), 7.14 (1H, d, J=1.0 Hz), 7.01-7.00 (1H, br m), 6.50 (1H, d, J=1.0 Hz), 4.58-3.98 (1H, br m), 3.83 (3H, s), 3.74-3.29 (4H, br m), 2.99 (2H, s), 2.31 (3H, d, J=1.1 Hz), 2.08-1.77 (4H, m), 1.03-0.98 (2H, m), 0.89-0.85 (2H, m); MS [M+H]$^+$=513.

Example 56

1'-[(1-ethyl-4-methoxy-1H-indol-6-yl)carbonyl]-6-(1H-tetrazol-5-yl)spiro[chroman-2,4'-piperidin]-4-one

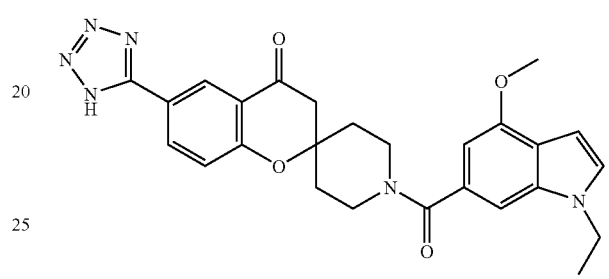

The intended compound was obtained as a slightly yellowish substance according to the method of Example 8 but using 1-ethyl-4-methoxy-1H-indole-6-carboxylic acid in place of 1,4-dimethoxy-1H-indole-6-carboxylic acid. $^1$H-NMR (400 MHz, DMSO-d$_6$) δ: 8.42-8.40 (1H, br m), 8.24 (1H, dd, J=8.5, 2.0 Hz), 7.33-7.27 (2H, m), 7.11 (1H, s), 6.53 (1H, s), 6.42 (1H, d, J=3.2 Hz), 4.41-4.10 (1H, br m), 4.15 (3H, q, J=7.2 Hz), 3.77 (3H, s), 3.75-3.20 (3H, br m), 2.98 (2H, s), 1.97-1.78 (4H, m), 1.38 (3H, t, J=7.2 Hz); MS [M+H]$^+$=487.

Example 57

5-{1'-[(1-cyclopropyl-4-methoxy-1H-indol-6-yl)carbonyl]-4-oxo-spiro[chroman-2,4'-piperidin]-6-yl}-4H-1,2,4-triazole-3-carboxamide

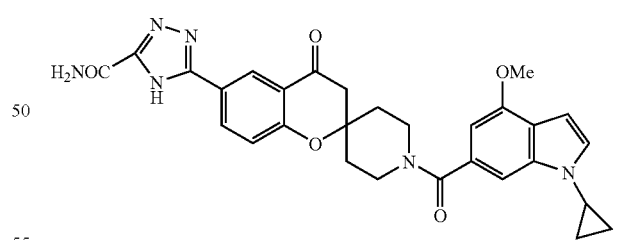

To a solution of 1-cyclopropyl-4-methoxy-1H-indole-6-carboxylic acid (54 mg) and 5-[4-oxo-spiro(chroman-2,4'-piperidin)-6-yl]-4H-1,2,4-triazole-3-carboxamide (102 mg) in DMF (4 mL) were added TEA (77 uL), HOBT (42 mg), and WSC (53 mg) at room temperature and the reaction mixture was stirred at room temperature overnight. The reaction mixture was poured into H$_2$O, extracted with CHCl$_3$, dried over sodium sulfate, filtered, and concentrated in reduced pressure. The residue was purified by column chromatography on silica gel using a mixture of CHCl$_3$/MeOH (1:0-10:1) as eluent to give the title compound as a colorless solid.

¹H-NMR (400 MHz, CDCl₃) δ: 8.78-8.60 (1H, m), 8.40-8.25 (1H, m), 7.29 (1H, s), 7.15 (1H, d, J=8.0 Hz), 7.09 (1H, d, J=4.0 Hz), 6.57 (1H, s), 6.52 (1H, d, J=4.0 Hz), 4.30-4.17 (1H, m), 3.95 (3H, s), 3.62-3.38 (3H, m), 3.38-3.32 (1H, m), 2.85 (2H, s), 2.28-1.70 (4H, m), 1.06-1.04 (2H, m), 1.00-0.97 (2H, m); MS [M+H]⁺=541.

Example 58

1'-[(1,3-diethyl-7-methoxy-2-oxo-2,3-dihydro-1H-benzimidazol-5-yl)carbonyl]-6-(1H-tetrazol-5-yl)spiro[chroman-2,4'-piperidin]-4-one

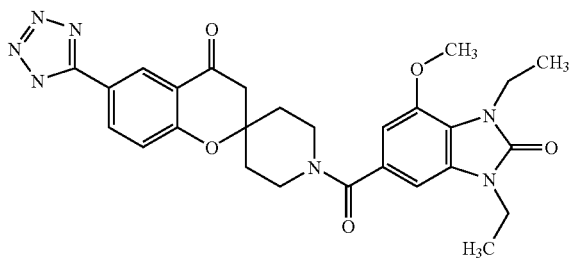

The intended compound was obtained as an off-white solid according to the method of Example 28 but using methyl 1,3-diethyl-7-methoxy-2-oxo-2,3-dihydro-1H-benzimidazol-5-carboxylate in place of ethyl 4-methoxy-1-methyl-1H-pyrazolo[3,4-b]pyridine-6-carboxylate. ¹H-NMR (400 MHz, DMSO-d₆) δ: 8.42 (1.0H, d, J=2.2 Hz), 8.24 (1.0H, dd, J=8.7, 2.2 Hz), 7.33 (1.0H, d, J=8.7 Hz), 6.93 (1.0H, s), 6.80 (1.0H, s), 4.30-4.10 (1.0H, m), 3.98 (2.0H, q, J=6.8 Hz), 3.89 (3.0H, s), 3.85 (2.0H, q, J=6.8 Hz), 3.40-3.20 (3.0H, m), 2.98 (2.0H, s), 2.10-1.88 (2.0H, m), 1.86-1.73 (2.0H, m), 1.18 (6.0H, q, J=6.8 Hz); MS [M+H]⁺=532.

Example 59

5-{1'-[(6-cyclopropyl-1-isopropyl-1H-pyrazolo[3,4-b]pyridin-4-yl)carbonyl]-4-oxo-spiro[chroman-2,4'-piperidin]-6-yl}nicotinic acid

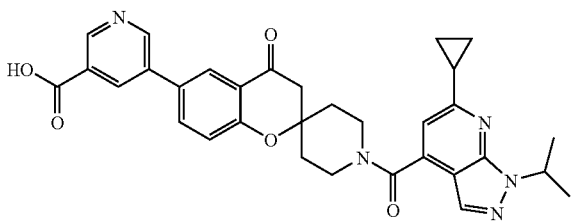

The title compound was prepared as a colorless amorphous substance according to the method descried in Example 45 but using 6-cyclopropyl-1-isopropyl-1H-pyrazolo[3,4-b]pyridine-4-carboxylic acid in place of cyclopropyl-4-ethoxy-3-methyl-1H-indole-6-carboxylic acid. ¹H-NMR (400 MHz, DMSO-d₆) δ: 9.03-8.98 (2H, m), 8.41 (1H, s), 8.07-8.01 (3H, m), 7.25 (1H, d, J=8.8 Hz), 7.13 (1H, s), 5.10 (1H, sept, J=6.8 Hz), 4.39-4.30 (1H, br m), 3.73-3.28 (3H, br m), 2.95 (2H, s), 2.32-2.24 (1H, m), 2.12-1.65 (4H, m), 1.46 (6H, d, J=6.8 Hz), 1.08-1.04 (4H, m); MS [M+H]⁺=566.

Example 60

1'-[(1-cyclopropyl-4-methoxy-1H-benzimidazol-6-yl)carbonyl]-6-(1H-tetrazol-5-yl)spiro[chroman-2,4'-piperidin]-4-one

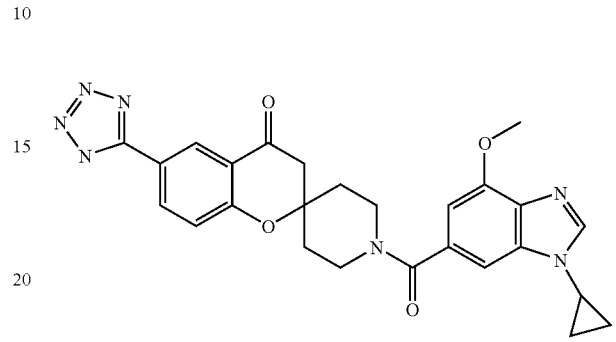

To a solution of methyl 1-cyclopropyl-4-methoxy-1H-benzimidazole-6-carboxylate (94 mg) in THF (4 mL) and MeOH (4 mL) was added 5N NaOH (0.38 mL) at rt. and the reaction mixture was stirred 2 h at 60° C. followed by addition of 5N HCl (0.38 mL). The mixture was concentrated in vacuo and coevaporated with toluene (×2). The residue was diluted with DMF (4 mL) and H₂O (1 mL) followed by addition of amine (147 mg), triethylamine (0.080 mL), EDCI×HCl (110 mg) and HOBT (77 mg) at r.t. The reaction mixture was stirred for 1 h at 90° C. Water was added to the solution at r.t., precipitated solid was collected, and washed with water and dried in vacuo to afford the title compound as a beige solid. ¹H-NMR (400 MHz, DMSO-d₆) δ: 8.42 (1H, d, J=2.2 Hz), 8.24 (1H, dd, J=8.7, 2.2 Hz), 8.18 (1H, s), 7.34 (1H, d, J=8.7 Hz), 7.25 (1H, s), 6.76 (1H, s), 4.41-4.20 (1H, m), 3.94 (3H, s), 3.66-3.64 (3H, m), 3.55-3.45 (1H, m), 2.99 (2H, s), 2.10-1.75 (4H, m), 1.11-0.98 (4H, m); MS [M+H]⁺=500.

Reference Example 1

1-Ethyl-3-methyl-1H-thieno[2,3-c]pyrazol-5-carboxylic acid 3.05 g of Ethylhydrazine and 6.54 g of Ethyl acetoacetate was dissolved in 10 mL of EtOH and the mixture was heated at 80° C. overnight. The mixture was cooled and partitioned between CHCl₃ and water. The organic layer was drier over Na₂SO₄, concentrated to give 2.43 g of crude 2-ethyl-5-methyl-2,4-dihydro-3H-pyrazol-3-one. 2.35 g of the material was diluted with 4 mL of DMF and 6.2 mL of POCl₃ was added dropwise thereto. The mixture was heated at 80° C. overnight, then cooled to room temperature. After addition of ice, the mixture was partitioned between CHCl₃ and water. The organic layer was dried over Na₂SO₄ and concentrated to give 1.46 g of crude 5-chloro-1-ethyl-3-methyl-1H-pyrazole-4-carbaldehyde. 516 mg of the material was diluted with 10 mL of EtOH and 440 mg of HSCH₂COOEt and 930 mg of K₂CO₃ was added thereto. The mixture was stirred at 80° C. overnight. The reaction mixture was cooled and 5 mL of 1N NaOHaq and 5 mL of MeOH was added thereto successively. Then the mixture was heated at 85° C. for 3 hrs. After cooled, the mixture was acidified with 1N HCl (to pH 1.5), then diluted with water. The precipitate was filtered, washed with water and n-hexane, dried in vacuo to afford 214 mg of the targeted compound.

Reference Example 2

1-Cyclopropyl-1H-pyrrole-2-carbaldehyde 44.46 ml of $POCl_3$ was added to a stirred solution of 1-cyclopropyl-1H-pyrrole (46.46 g) in 37 ml of DMF with cooling with ice, then the mixture was stirred at room temperature overnight. The mixture was poured into 336 ml of 5N NaOHaq with cooling with ice, and the mixture was made basic with an additional 5N NaOHaq. The mixture was extracted with $CH_2Cl_2$ and the organic extract was dried over Na2SO4, concentrated, and the residue was purified on SiO2 column chromatography (n-hexane-EtOAc system) to give 38.91 g of 1-cyclopropyl-1H-pyrrol-2-carbaldehyde as a colorless oil.

Reference Example 3

Ethyl 4-acetoxy-1-cyclopropyl-1H-indole-6-carboxylate 14.57 g of Na was added portionwise to 400 ml of EtOH. To the mixture was added a solution of 38.91 g of 1-cyclopropyl-1H-pyrrole-2-carbaldehyde and 48.23 ml of diethyl succinate in 100 ml of EtOH at 50° C., then the mixture was refluxed overnight. 140 ml of 5N HCl was added to the mixture at 0° C. and EtOH was evaporated. The concentrate was extracted with CHCl3 and the extract was dried over Na2SO4 and concentrated to give red oil. The material was dissolved in 400 ml of acetic anhydride and 47.40 g of AcOK was added thereto. The mixture was refluxed for 30 min and allowed to cool to room temperature. The mixture was filtrated and the filtrate was concentrated. The residue was purified on SiO2 column chromatography (n-hexane-EtOAc system) to give 72.3 g of ethyl 4-acetoxy-1-cyclopropyl-1H-indole-6-carboxylate as red oil.

Reference Example 4

Ethyl 1-cyclopropyl-4-hydroxy-1H-indole-6-carboxylate

To a solution of 72.33 g of ethyl 4-acetoxy-1-cyclopropyl-1H-indole-6-carboxylate in 360 ml of EtOH placed in a 2 L flask was added 69.58 g of K2CO3 and the mixture was stirred at room temperature for 4 hrs. EtOH was evaporated and the concentrate was diluted with EtOAc. The mixture was washed with water and saturated brine, dried over Na2SO4, and concentrated. The residue was triturated with toluene and n-hexane to give 49.78 g of ethyl 1-cyclopropyl-4-hydroxy-1H-indole-6-carboxylate as a pale tan solid.

Reference Example 5

Ethyl 1-cyclopropyl-4-methoxy-1H-indole-6-carboxylate

To a stirred suspension of 14.56 g of ethyl 1-cyclopropyl-4-hydroxy-1H-indole-6-carboxylate and 16.2 g of K2CO3 and 220 ml of DMF was added 7.48 ml of MeI and the mixture was stirred at 60° C. for 3 hrs. The mixture was allowed to cool, diluted with EtOAc, washed with water and saturated brine successively, dried over Na2SO4, then concentrated. The residue was purified on SiO2 column chromatography (n-hexane-EtOAc) to afford 15.15 g of ethyl 1-cyclopropyl-4-methoxy-1H-indole-6-carboxylate as a pale yellow oil.

Reference Example 6

Ethyl 1-cyclopropyl-4-ethoxy-1H-indole-6-carboxylate

The compound was prepared according to the procedure for ethyl 1-cyclopropyl-4-methoxy-1H-indole-6-carboxylate but using EtI in place of MeI.

Reference Example 7

1-Cyclopropyl-4-ethoxy-1H-indole-6-carboxylic acid

The compound was prepared according to the procedure for 1-Cyclopropyl-4-methoxy-1H-indole-6-carboxylic acid but using ethyl 1-cyclopropyl-4-ethoxy-1H-indole-6-carboxylate in place of ethyl 1-cyclopropyl-4-methoxy-1H-indole-6-carboxylate.

Reference Example 8

1-Cyclopropyl-4-methoxy-1H-indole-6-carboxylic acid 35 ml of 5N NaOHaq was added to a solution of 15.15 g of ethyl 1-cyclopropyl-4-methoxy-1H-indole-6-carboxylate in MeOH and the mixture was stirred at 60° C. for 8 hrs. The mixture was cooled to 0° C. and 35 ml of 5N HCl was added thereto. The precipitate was filtered and dried in vacuo to give 13.8 g of 1-cyclopropyl-4-methoxy-1H-indole-6-carboxylic acid as a colorless solid.

Reference Example 9

Ethyl 1-cyclopropyl-3-formyl-4-methoxy-1H-indole-6-carboxylate 1.28 ml of $POCl_3$ was added dropwise to a solution of 3.24 g of ethyl 1-cyclopropyl-4-methoxy-1H-indole-6-carboxylate in 30 ml of DMF and the mixture was stirred at 0° C. for 2 hrs. The mixture was diluted with EtOAc and 25 ml of 1N NaOH was added. Then the mixture was made basic using saturated NaHCO3aq. The mixture was extracted with EtOAc and the extract was washed with water and saturated brine, dried over Na2SO4, then concentrated. The residue was purified on SiO2 column chromatography (EtOAc-n-Hexane system) to give 2.4 g of ethyl 1-cyclopropyl-3-formyl-4-methoxy-1H-indole-6-carboxylate.

Reference Example 10

Ethyl 1-cyclopropyl-3-methyl-4-methoxy-1H-indole-6-carboxylate

To a stirred solution of 3.30 g of ethyl 1-cyclopropyl-3-formyl-4-methoxy-1H-indole-6-carboxylate in 33 ml of EtOH was added 2.57 g of TsNHNH2 and the mixture was refluxed for 30 min. After evaporation of EtOH, the mixture was diluted with 28 ml of DMF and 28 ml of sulfolane, then 2.89 g of NaBH3CN and 0.57 g of TsOH $H_2O$ was added thereto successively. The mixture was refluxed for 30 min and cooled to room temperature. After diluted with Et2O, the mixture was washed successively with water, saturated NaHCO3aq, and saturated brine, dried over Na2SO4, concentrated. The residue was purified on SiO2 column chromatography (EtOAc/n-hexane system) to give 2.78 g of Ethyl 1-cyclopropyl-3-methyl-4-methoxy-1H-indole-6-carboxylate as a colorless powder.

Reference Example 11

Ethyl 3-chloro-4-methoxy-1H-indole-6-carboxylate

To a stirred solution of 1.29 g of ethyl 1-cyclopropyl-4-methoxy-1H-indole-6-carboxylate in 13 ml of THF was added 801 mg of N-chlorosuccinimide and the mixture was stirred at 60° C. for 2 hrs. After diluted with EtOAc, the mixture was washed successively with water and saturated brine, dried over Na2SO4, and concentrated. The residue was purified on SiO2 column chromatography to afford 1.03 g of ethyl-3-chloro-1-cyclopropyl-4-(methoxy)-1H-indole-6-carboxylate as a colorless solid.

Reference Example 12

3-chloro-1-cyclopropyl-4-methoxy-1H-indole-6-carboxylic acid

To a stirred solution of 1.03 g of ethyl-3-chloro-1-cyclopropyl-4-(methyloxy)-1H-indole-6-carboxylate in 15 ml of MeOH and 10 ml of THF was added 2 ml of 5N NaOHaq and the mixture was stirred at 60° C. for 9 hrs. After evaporation of MeOH and THF, the mixture was diluted with water and 2 ml of 5N HClaq was added thereto. The precipitate was collected by filtration and dried in vacuo to give 798 mg of 3-chloro-1-cyclopropyl-4-(methyloxy)-1H-indole-6-carboxylic acid as a colorless solid.

Reference Example 13

1-Cyclopropyl-3-methyl-4-methoxy-1H-indole-6-carboxylic acid 4.66 mL of 5 N NaOH aqueous was added to a solution of 3.19 g of ethyl 1-cyclopropyl-3-methyl-4-methoxy-1H-indole-6-carboxylate in 32 mL of MeOH and the mixture was stirred at 60° C. overnight. The mixture was cooled and 46.6 mL of 1N HCl was added thereto. The precipitate was filtered, collected and dried in vacuo to afford 2.70 g of 1-Cyclopropyl-3-methyl-4-methoxy-1H-indole-6-carboxylic acid as a colorless solid.

Reference Example 14

6-bromo-1'-(tert-butoxycarbonyl)spiro[chroman-2,4'-piperidin]-4-one 60 mL of MeOH, 7.97 g of N-Boc-piperidin-4-one, and 3.34 mL of pyrrolidine were added to 8.60 g of 5-bromo-2-hydroxyacetophenone put in a 200-mL flask equipped with a condenser, and the mixture was overnight heated under reflux. The reaction mixture was cooled to room temperature, and concentrated. The residue was purified through silica gel column chromatography (eluted with n-hexane/EtOAc=6/1) to obtain the intended compound as a pale yellow solid.

Reference Example 15

6-bromospiro[chroman-2,4'-piperidin]-4-one hydrochloride

A mixture of 25.0 g of 5-bromo-2-hydroxyacetophenone, 25.0 g of N-Boc-piperidin-4-one, 9.68 mL of pyrrolidine and 250 mL of MeOH was heated under reflux overnight. The reaction mixture was cooled to room temperature and concentrated. The residue was put into 300 mL of 1,4-dioxane, and 100 mL of concentrated hydrochloric acid was added thereto and stirred at room temperature for 4 hour. The reaction solution was poured into water, and stirred overnight. The resulting precipitate was taken out through filtration, washed with water and n-hexane, and dried under reduced pressure to obtain the intended compound as a yellow solid.

Reference Example 16 tert-butyl 6-cyano-4-oxospiro[chroman-2,4'-piperidine]-1'-carboxylate

A mixture of tert-butyl 6-bromo-4-oxospiro[chroman-2,4'-piperidine]-1'-carboxylate (143 g, 0.36 mol), $Zn(CN)_2$ (84.7 g, 0.72 mol), $Pd(PPh_3)_4$ (20 g, 17 mmol) and dry DMF (1 liter) was stirred under an argon atmosphere at 90° C. for 6 hours. The resulting mixture was, after cooled, diluted with ethyl acetate (1 liter), and washed with aqueous 12% ammonia, water, and saturated brine in order. The organic layer was dried over sodium sulfate, and concentrated, and the residue was treated with methanol, and the resulting insoluble solid was taken out through filtration, and dried under a reduced pressure to obtain tert-butyl 6-cyano-4-oxospiro[chroman-2,4'-piperidine]-1'-carboxylate as a colorless solid.

Reference Example 17 tert-butyl 4-oxo-6-(1H-tetrazol-5-yl)spiro[chroman-2,4'-piperidine]-1'-carboxylate 67.5 g of sodium azide, 143 g of triethylamine hydrochloride, and 1.2 liters of dry DMF were added to the cyano compound (119 g) produced in Reference Example 16, and the mixture was stirred under a nitrogen atmosphere at 100° C. for 12 hours. After cooled, the reaction mixture was partitioned between 1 N hydrochloric acid (200 mL), water and ethyl acetate. The aqueous layer was further extracted three times with ethyl acetate, and the combined organic layers were washed with water and brine, dried over sodium sulfate and concentrated. The residue was triturated with methanol, and the insoluble solid was collected through filtration and dried under reduced pressure to obtain tert-butyl 4-oxo-6-(1H-tetrazol-5-yl)spiro[chroman-2,4'-piperidine]-1'-carboxylate as a colorless solid.

Reference Example 18

6-(1H-tetrazol-5-yl)spiro[chroman-2,4'-piperidine]-4-one

4 N HCl-1,4-dioxane (200 mL) was added to 40.6 g tert-butyl 4-oxo-6-(1H-tetrazol-5-yl)spiro[chroman-2,4'-piperidine]-1'-carboxylate produced in Reference Example 17, and stirred at room temperature for 5 hours. The reaction mixture was concentrated, and the residue was triturated with methanol. The insoluble solid was collected through filtration, and dried under reduced pressure to obtain 6-(1H-tetrazol-5-yl)-spiro[chroman-2,4'-piperidine]-4-one as a colorless solid.

Reference Example 19

5-Bromo-nicotinic acid tert-butyl ester

5-Bromo-nicotinic acid (20.2 g, 100 mmol) was dissolved in $CHCl_3$ (200 mL) and tert-BuOH (40 mL); and WSC (21.1 g, 110 mmol) and DMAP (21.1 g, 10 mmol) was added thereto in order, and stirred at room temperature over night. The reaction mixture was diluted with chloroform, washed with 0.5N HCl aq. (220 mL), 0.5N NaOH aq. (100 mL), brine and dried over MgSO$_4$ and silica gel. After filtration, the solvents were removed in vacuo to afford 5-Bromo-nicotinic acid tert-butyl ester as a colorless solid. This solid was used for the next step without further purification.

Reference Example 20

5-{1'-tert-butoxycarbonyl]-4-oxospiro[chroman-2,4'-piperidin]-6-yl}nicotinic acid tert-butyl ester tert-butyl-6-bromo-4-oxospiro[chroman-2,4'-piperidine]-1'-carboxylate (19.8 g, 50.0 mmol), bis(pinacolato)diboran (14.0 g, 55.0 mmol), Pd(OAc)$_2$ (560 mg, 2.50 mmol), DPPF (2.77 g, 5.00 mmol), and AcOK (5.82 g, 60.0 mmol) were suspended in dioxane (250 mL) and heated at 100° C. for 10 hours. After cooling down to room temperature, 5-bromo-nicotinic acid tert-butyl ester (14.2 g, 55.0 mmol), Pd(PPh$_3$)$_4$ (5.78 g, 5.00 mmol) and 2M Na$_2$CO$_3$ aq. (125 mL, 250 mmol) were added to the reaction mixture; and then heated at 100° C. for 15 hours. The reaction mixture was diluted with EtOAc and H$_2$O, organic layer was washed with brine and dried over MgSO$_4$. After filtration, the solvents were removed in vacuo and the residue was purified by silica gel column chromatography (hexane/EtOAc=10/0 to 6/4) and the obtained brown solid was crystallized from EtOAc/hexane (1/1) to afford 5-{1'-tert-butoxycarbonyl]-4-oxospiro[chroman-2,4'-piperidin]-6-yl}nicotinic acid tert-butyl ester as a pale yellow solid.

Reference Example 21

5-{4-oxospiro[chroman-2,4'-piperidin]-6-yl}nicotinic acid di-hydrochloride

5-{1'-tert-butoxycarbonyl]-4-oxospiro[chroman-2,4'-piperidin]-6-yl}nicotinic acid tert-butyl ester (14.0 g, 28.3 mmol) was dissolved in CHCl$_3$ (70 mL) and 4N HCl in dioxane (210 mL) was added thereto, and stirred at room temperature for 20 h. The resulted precipitate was filtered and washed with CHCl$_3$ and Et$_2$O to afford 5-{4-oxospiro[chroman-2,4'-piperidin]-6-yl}nicotinic acid di-hydrochloride as a colorless solid.

Reference Example 22 tert-butyl 6-cyano-4-hydroxy-1'H-spiro[chroman-2,4'-piperidine]-1'-carboxylate

To a solution of 15 g of tert-butyl 6-cyano-4-oxospiro[chroman-2,4'-piperidine]-1'-carboxylate in 250 mL of EtOH-THF (1:4) at 0° C. was added NaBH$_4$ portionwise, and the reaction mixture was allowed to warm up to r.t. After stirring for 1 h, NH$_4$Claq was added to the reaction mixture and the aqueous mixture was extracted with AcOEt twice. The combined organic layers were washed with brine, dried over Na$_2$SO$_4$, filtered, and concentrated in reduced pressure to give the intended compound as a pale yellow solid.

Reference Example 23 tert-butyl 4-{[tert-butyl(dimethyl)silyl]oxy}-6-cyano-1'H-spiro[chroman-2,4'-piperidine]-1'-carboxylate To a solution of 15.1 g of tert-butyl 6-cyano-4-hydroxyspiro[chroman-2,4'-piperidine]-1'-carboxylate in DMF were added 3.6 g of imidazole and 7.95 g of TBSCl at r.t., and the reaction mixture was stirred at r.t. for 1 d. To this reaction mixture was added 598 mg of imidazole and 1.3 g of TBSCl at rt, and the reaction mixture was stirred at r.t. for 1 d. The reaction mixture was poured into ice-cold brine, and the aqueous mixture was extracted with AcOEt twice. The combined organic layers were washed with H$_2$O and brine, dried over Na$_2$SO$_4$, filtered, and concentrated in reduced pressure. The residue was purified by column chromatography on silica gel using a mixture of hexane and AcOEt (100/0-80/20) as eluent to give the intended compound.

Reference Example 24 tert-butyl 6-[amino(hydroxyimino)methyl]-4-{[tert-butyl(dimethyl)silyl]oxy}-1'H-spiro[chroman-2,4'-piperidine]-1'-carboxylate To a suspension of 18.2 g of tert-butyl 4-{[tert-butyl(dimethyl)silyl]oxy}-6-cyanospiro[chroman-2,4'-piperidine]-1'-carboxylate in EtOH was added 16.3 mL of Et$_3$N and 8.12 g of hydroxyamine hydrochloride at rt, and the reaction mixture was stirred at 85° C. for Id. The resultant solution was cooled to r.t., and concentrated in reduced pressure. To the residue was added H$_2$O, the resultant white solid was filtered, washed with H$_2$O, and dried in vacuo to give a crude product, which was used in the next step without further purification.

Reference Example 25 tert-butyl 6-{amino[({[(2-ethylhexyl)oxy]carbonyl}oxy)-imino]methyl}-4-{[tert-butyl(dimethyl)silyl]oxy}spiro[chroman-2,4'-piperidine]-1'-carboxylate To a solution of tert-butyl 6-[amino(hydroxyimino)methyl]-4-{[tert-butyl(dimethyl)silyl]oxy}spiro[chroman-2,4'-piperidine]-1'-carboxylate in 80 mL of DMF were added 3.78 mL of pyridine and 8.4 mL of 2-Ethylhexyl chloroformate at 0° C., and the reaction mixture was stirred at 0° C. for 1.5 h. The reaction mixture was poured into ice-cold brine, and extracted with AcOEt twice. The combined organic layers were washed with H$_2$O and brine, dried over Na$_2$SO$_4$, filtered, and concentrated in reduced pressure to give a crude product, which was used in the next step without further purification.

Reference Example 26 tert-butyl 4-{[tert-butyl(dimethyl)silyl]oxy}-6-(5-oxo-4,5-dihydro-1,2,4-oxadiazol-3-yl)spiro[chroman-2,4'-piperidine]-1'-carboxylate A solution of tert-butyl 6-{amino[({[(2-ethylhexyl)oxy]carbonyl}oxy)imino]methyl}-4-{[tert-butyl(dimethyl)silyl]oxy}spiro[chroman-2,4'-piperidine]-1'-carboxylate in 100 mL of xylene was stirred at 145° C. for 14 h. The reaction mixture was cooled to r.t., and concentrated in reduced pressure. The residue was purified by column chromatography on silica gel using a mixture of hexane-AcOEt (100/1-35/65) as an eluent to give the product as an off-white solid.

Reference Example 27 tert-butyl 4-hydroxy-6-(5-oxo-4,5-dihydro-1,2,4-oxadiazol-3-yl)spiro[chroman-2,4'-piperidine]-1'-carboxylate To a solution of 13.4 g of tert-butyl 4-{[tert-butyl(dimethyl)silyl]oxy}-6-(5-oxo-4,5-dihydro-1,2,4-oxadiazol-3- yl)spiro[chroman-2,4'-piperidine]-1'-carboxylate in 200 mL of EtOH-THF (5.5:1) at 0° C. was added 67 ml of 1M HClaq dropwise, and the reaction mixture was stirred at r.t. for 18 h. The reaction mixture was cooled to 0° C., and the mixture was basified with NaHCO$_3$. The mixture was concentrated in reduced pressure, and the residue was acidified with 1M HClaq. The aqueous mixture was extracted with a mixture of CHCl$_3$-MeOH (9:1) three times, and the combined organic layers was washed with brine, dried over Na$_2$SO$_4$, and concentrated in reduces pressure to give the product as a pale brown solid.

Reference Example 28 tert-butyl 4-oxo-6-(5-oxo-4,5-dihydro-1,2,4-oxadiazol-3-yl)spiro[chroman-2,4'-piperidine]-1'-carboxylate To a solution of 1.0 g of tert-butyl 4-hydroxy-6-(5-oxo-4,5-dihydro-1,2,4-oxadiazol-3-yl)spiro[chroman-2,4'-piperidine]-1'-carboxylate in 40 ml of THF-CH$_3$CN (1:1) at r.t. were added 2.0 g of MS 4A, 435 mg of NMO, and 88 mg of TPAP, and the reaction mixture was stirred at r.t. overnight. The mixture was filtered through a Celite pad, washed with CHCl$_3$ and CHCl$_3$-MeOH (9:1), and the filtrate was concentrated in reduced pressure. The residue was purified by column chromatography on silica gel using a mixture of hexane-AcOEt (100/0-0/100) as eluent to give the intended compound as a colorless solid.

Reference Example 29

6-(5-oxo-4,5-dihydro-1,2,4-oxadiazol-3-yl)spiro[chroman-2,4'-piperidin]-4-one hydrochloride A suspension of 437 mg of tert-butyl 4-oxo-6-(5-oxo-4,5-dihydro-1,2,4-oxadiazol-3-yl)spiro[chroman-2,4'-piperidine]-1'-carboxylate in 10 mL of 4N HCl in dioxane was stirred at rt for 1 d, the resultant white solid was filtered, and washed with ether. The collected white solid was dried in vacuo at 50° C. to give the intended compound as a colorless solid.

Reference Example 30

1'-tert-butoxycarbonyl-6-(4",4",5",5"-tetramethyl-1",3",2"-dioxaborolan-2"-yl)spiro[chroman-2,4'-piperidin]-4-one tert-Butyl 6-bromo-4-oxospiro[chroman-2,4'-piperidine]-1'-carboxylate (99.0 g, 250 mmol), bis(pinacolato)diboran (70.2 g, 275 mmol), Pd(OAc)$_2$ (2.80 g, 12.5 mmol), DPPF (13.9 g, 25.0 mmol), and AcOK (29.1 g, 300 mmol) were suspended in dioxane (500 ml) and heated at 100° C. for 20 h. After cooling down to room temperature, MeOH (500 ml) was added and further stirred for 1 h. The resulted precipitate was filtered and the cake was washed with MeOH to obtain the intended compound as a pale brown solid.

Reference Example 31

5-(1'-tert-butoxycarbonyl-4-oxospiro[chroman-2,4'-piperidin]-6-yl)nicotinic acid methyl ester 1'-tert-butoxycarbonyl-6-(4",4",5",5"-tetramethyl-1",3",2"-dioxaborolan-2"-yl)spiro[chroman-2,4'-piperidin]-4-one (2.00 g, 4.51 mmol), 5-bromonicotinic acid methyl ester (1.17 g, 5.42 mmol), Pd(OAc)$_2$ (50.6 mg, 0.226 mmol), DPPF (250 g, 0.451 mmol), and K$_3$PO$_4$ (1.91 g, 9.02 mmol) were suspended in DME (500 mL) and heated at 100° C. for 18 hours. The reaction mixture was filtered through Celite, the residue on the Celite was washed with chloroform, and the filtrate and the washing were combined and concentrated under a reduced pressure. The resulting residue was purified through silica gel column chromatography (hexane/EtOAc=10/0 to 2/8) to obtain the intended compound as a pale yellow foam.

Reference Example 32

5-(4-oxospiro[chroman-2,4'-piperidin]-6-yl)nicotinic acid methyl ester di-hydrochloride 5-(1'-tert-butoxycarbonyl-4-oxospiro[chroman-2,4'-piperidin]-6-yl)nicotinic acid methyl ester (22.0 g, 48.6 mmol) was suspended in MeOH (110 mL) and 4 N HCl in dioxane (220 mL) was added thereto, and stirred at room temperature for 14 hours. The solvents were removed in vacuo and the resulting solid was washed with MeOH/Et$_2$O (50 mL/200 mL) to obtain the intended compound as a colorless solid.

Reference Example 33

3"-{1'-tert-butoxycarbonyl]-4-oxospiro[chroman-2,4'-piperidin]-6-yl}benzoic acid tert-butyl-6-bromo-4-oxospiro[chroman-2,4'-piperidine]-1'-carboxylate (39.6 g, 100 mmol), 3-carboxy-phenylboronicacid (16.6 g, 100 mmol), Pd(PPh$_3$)$_4$ (5.78 g, 5.00 mmol), and 2M Na$_2$CO$_3$ aq. (250 ml, 500 mmol) were suspended in 1,4-dioxane (400 ml) and heated at 100° C. for 18 h. The reaction mixture was diluted with CHCl$_3$ and dil HCl aq. (1.1 mol), the aqueous layer was extracted with CHCl$_3$. The combined organic layer was washed with H$_2$O and brine, dried over MgSO$_4$. The desiccant was removed through filtration and the filtrate was concentrated under reduced pressure. The residue was triturated with EtOAc and the insoluble solid was collected through filtration to obtain the intended compound as a colorless solid.

Reference Example 34

Methyl 3"-{1'-tert-butoxycarbonyl]-4-oxospiro[chroman-2,4'-piperidin]-6-yl}benzoate 3"-{1'-tert-butoxycarbonyl-4-oxospiro[chroman-2,4'-piperidin]-6-yl}benzoic acid (24.0 g, 54.9 mmol) was dissolved in CHCl$_3$ (120 ml), and MeOH (24 ml), WSC (15.8 g, 82.4 mmol) and DMAP (10.0 g, 82.4 mmol) was added thereto in this order, and the mixture was stirred at room temperature over night. The reaction mixture was diluted with CHCl$_3$ and diluted HCl aq. (220 mmol). The organic layer was washed with 0.5N NaOH aq., brine and dried over MgSO$_4$ and silica gel. The desiccant was removed through filtration and the filtrate was concentrated under reduced pressure. The residue was triturated with MeOH and the insoluble solid was collected through filtration to obtain the intended compound as a pale yellow solid.

Reference Example 35

Methyl 5-{4-oxospiro[chroman-2,4'-piperidin]-6-yl}benzoate

The intended compound was produced according to the synthetic procedure for 5"-{4-oxospiro[chroman-2,4'-piperidin]-6-yl}nicotinic acid methyl ester di-hydrochloride but using methyl 3"-{1'-tert-butoxycarbonyl]-4-oxospiro[chroman-2,4'-piperidin]-6-yl}benzoate in place of 5"-{1'-tert-butoxycarbonyl]-4-oxospiro[chroman-2,4'-piperidin]-6-yl}nicotinic acid methyl ester.

Reference Example 36

6-(1H-tetrazol-5-yl)spiro[chroman-2,4'-piperidine]-4-one hydrochloride salt

A mixture of 5-bromo-2-hydroxyacetophenone (104.35 g, 485.26 mmol), N-Boc-piperidin-4-one (98.62 g, 494.96 mmol), 20 mL of pyrrolidine (17.26 g, 242.63 mmol) and 261 mL of MeOH was heated under reflux until the reaction was complete. The mixture was cooled, then 87 mL of $H_2O$ were added, and the mixture was filtered and dried to give tert-butyl 6-bromo-4-oxospiro[chroman-2,4'-piperidine]-1'-carboxylate. Alternatively, 10 mL of pyrrolidine (121.31 mmol) may be used in this procedure. To a solution of tert-butyl 6-bromo-4-oxospiro[chroman-2,4'-piperidine]-1'-carboxylate (6593 g, 16.6 mol) and DMF (33 L) was added $Zn(CN)_2$ (1947 g, 16.6 mol) and $Pd(PPh_3)_4$ (192 g, 0.17 mol). The slurry was heated to 90° C. for 3 hours, then cooled to room temperature and filtered. Water (16 L) was added to the filtrate. The resulting slurry was cooled to 5° C., stirred for 1 hour and filtered. The solid was washed with DMF/water (2:1) and dried under vacuum to give tert-butyl 6-cyano-4-oxospiro[chroman-2,4'-piperidine]-1'-carboxylate. A solution of 23 g of tert-butyl 6-cyano-4-oxospiro[chroman-2,4'-piperidine]-1'-carboxylate (67.17 mmol), 13.10 g sodium azide (201.52 mmol), 27.74 g of triethylamine hydrochloride (201.52 mmol), and 460 mL of dry DMF was stirred under a nitrogen atmosphere at 100° C. for 12 hours. After cooling to room temperature, 506 mL of EtOAc were added, followed by 322 mL of 1M HCl (322 mmol). Alternatively, 0.5M HCl may be added until pH=3. The resulting layers were separated, the organic layer was washed with water/methanol (115 mL/46 mL), and then concentrated to give tert-butyl 4-oxo-6-(1H-tetrazol-5-yl)spiro[chroman-2,4'-piperidine]-1'-carboxylate. A solution of 5.08 g of tert-butyl 4-oxo-6-(1H-tetrazol-5-yl)spiro[chroman-2,4'-piperidine]-1'-carboxylate (13.18 mmol), 8.8 mL of 12 M HCl (105.44 mmol) and 8 mL of methanol was heated to 50° C. until the reaction was complete. The resulting slurry was filtered, washed with 25 mL of methanol at room temperature, and dried to give 6-(1H-tetrazol-5-yl)spiro[chroman-2,4'-piperidine]-4-one hydrochloride salt.

Reference Example 37

Ethyl 3-methoxy-5-nitro-4-{[(trifluoromethyl)sulfonyl]oxy}benzoate 17.7 ml of Tf2O was added to a solution of 16.8 g of ethyl 4-hydroxy-3-(methyloxy)-5-nitrobenzoate and 11.3 ml of pyridine in 500 ml of CHCl3 at 0° C. The mixture was stirred for 30 min, then washed successively with water, HClaq, and saturated NaHCO3aq, dried over Na2SO4, and concentrated. The residual solid was washed with a mixed solvent of $CHCl_3$ and n-hexane to give a 22.0 g of the intended compound as a pale orange solid.

Reference Example 38

Ethyl 4-methyl-3-(methoxy)-5-nitrobenzoate

To a stirred solution of 4.92 g of $MeB(OH)_2$, 33.9 g of K2CO3, 25.6 g of ethyl 3-methoxy-5-nitro-4-{[(trifluoromethyl)sulfonyl]oxy}benzoate in 500 ml of THF and 50 ml of water was added 5.03 g of PdCl2 dppf and the mixture was stirred under argon atmosphere at 80° C. overnight. The mixture was diluted with AcOEt and water, filtered through Celite and the filtrate was extracted with AcOEt. The extract was washed successively with saturated NaCO3aq and saturated brine, dried over Na2SO4, and concentrated. The residue was purified on SiO2 column chromatography and the fractions containing the intended compound were concentrated. The resulting solid was washed with n-hexane and dried to give 12.9 g of the intended compound as a yellow solid.

Reference Example 39

Ethyl 3-(methoxy)-5-nitro-4-(2-oxoethyl)benzoate 13.3 ml of Me2NCH(OMe)2 was added to a solution of 4.78 g of ethyl 4-methyl-3-(methoxy)-5-nitrobenzoate in 10 ml of dimethylacetamide and the mixture was heated at 80° C. in a sealed tube for 40 minutes. The mixture was diluted with CHCl3, washed with water, dried over Na2SO4, and concentrated. The residue was purified on SiO2 column chromatography to give 4.02 g of the intended compound as a pale tan solid.

Reference Example 40

Ethyl 1,4-dimethoxy-1H-indole-6-carboxylate 250 mg of ethyl 3-(methoxy)-5-nitro-4-(2-oxoethyl)benzoate was dissolved in 5 ml of DMF and the solution was stirred over 50 mg of 10% Pd/C (50% wet) under hydrogen atmosphere for 6 hrs. Then the mixture was purged with $N_2$ and 126 uL of MeI and 276 mg of K2CO3 was added thereto. After stirred for 2 hrs, the mixture was diluted with Et2O, filtered through Celite. The filtrate was concentrated and purified on SiO2 column chromatography to give 184 mg of the intended compound as colorless oil.

Reference Example 41

Ethyl 1,4-dimethoxy-1H-indole-6-carboxylic acid 513 mg of ethyl 1,4-dimethoxy-1H-indole-6-carboxylate was dissolved in 10 ml of MeOH and 1 ml of 5N NaOHaq was added thereto. The mixture was heated at 80° C. with stirring overnight. After cooled to 0° C., the mixture was neutralized by 1 ml of 5N HClaq and extracted with CHCl3 and MeOH. The extract was dried over Na2SO4, concentrated. The resulting solid was washed with a mixed solvent of n-hexane, diethyl ether and MeOH to afford 352 mg of the intended compound as a pale purple solid.

Reference Example 42

Ethyl 3-O-tert-butyl 6-O-ethyl 1-cyclopropyl-4-ethoxy-1H-indole-3,6-dicarboxylate $(COCl)_2$ (713 ul) was added to the solution of ethyl 1-cyclopropyl-4-ethoxy-1H-indole-6-carboxylate (1.36 g) in $Et_2O$ 20 ml at r.t. and stirred for over night. The solvent was evaporated away and the residue was dissolved in toluene 20 ml. The reaction mixture was stirred at reflux for 1 h and cooled to room temperature. Pyridine (810 ul) and tert-butanol (3 ml) were added to the mixture, stirred for 1 h at r.t. The reaction mixture was quenched with saturated aqueous sodium bicarbonate, then washed with water, and saturated saline water in that order, and dried with sodium sulfate. This was filtered, concentrated, and purified through silica gel column chromatography (hexane/ethyl acetate) to obtain the title compound (1.71 g) as a colorless solid.

Reference Example 43

Ethyl 3-carbamoyl-1-cyclopropyl-4-ethoxy-1H-indole-6-carboxylate (COCl)$_2$ (713 ul) was added to the solution of ethyl 1-cyclopropyl-4-ethoxy-1H-indole-6-carboxylate (5.46 g) in Et$_2$O 70 ml at r.t. and stirred for over night. The solvent was evaporated away and the residue was dissolved in toluene 70 ml. The reaction mixture was stirred at reflux for 1 h and cooled to room temperature and 0.5 N solution of NH3 in dioxane (100 ml) was added dropwise and stirred for 2 h at r.t. The reaction mixture was diluted with ethyl acetate and water, washed with water and saturated saline water in that order, and dried with sodium sulfate. This was filtered, concentrated, and crystallized from mixed solvent of hexane and ethyl acetate to give the title compound (5.06 g) as a colorless solid

Reference Example 44

Ethyl 1-cyclopropyl-4-ethoxy-3-methylcarbamoyl-1H-indole-6-carboxylate

3-O-tert-Butyl 6-O-ethyl 1-cyclopropyl-4-ethoxy-1H-indole-3,6-dicarboxylate (1.23 g) was added to 4N solution of hydrochloric acid in dioxane (5 ml) at r.t. and the mixture was stirred for 1 h, evaporated and crystallized from hexane to give carboxylic acid of intended compound (996 mg) as a colorless solid. (COCl)$_2$ (117 ul) to the solution of this carboxylic acid (217 mg) in chloroform (5 ml) and then one portion of DMF was added at 0° C. The reaction mixture was stirred for 2 h at r.t., evaporated, and dissolved in THF (5 ml). 2M solution of methylamine in THF (3 ml) was added to the reaction mixture, stirred for 30 min at r.t., diluted with ethyl acetate and water, washed with water and saturated saline water in that order, and dried with sodium sulfate. This was filtered, concentrated to give title compound (216 mg).

Reference Example 45

Ethyl 1-cyclopropyl-4-(2-hydroxyethoxy)-1H-indole-6-carboxylate

The compound was prepared according to the procedure for ethyl 1-cyclopropyl-4-methoxy-1H-indole-6-carboxylate but using bromoethyl acetate in place of MeI.

Reference Example 46

Ethyl 4-(1-methyl-2-oxoethyl)-3-nitrobenzoate

Sodium bicarbonate (318 mg) was added to the mixture of ethyl 3-nitro-4-(2-oxoethyl)benzoate (401 mg) and MeI (426 mg) in DMF (5 ml), stirred for over night at r.t., diluted with ethyl acetate, washed with water and saturated saline water in that order, and dried with sodium sulfate. This was filtered, concentrated, and purified through silica gel column (hexane/ethyl acetate) to give title compound (227 mg) as a colorless oil.

Reference Example 47

Ethyl 1,4-dimethoxy-3-methyl-1H-indole-6-carboxylate

According to the methods of Reference Example 40, the intended compound was obtained as a colorless oil, but using ethyl 5-methoxy-4-(1-methyl-2-oxoethyl)-3-nitrobenzoate in place of ethyl 3-methoxy-5-nitro-4-(2-oxoethyl)benzoate.

Reference Example 48 tert-Butyl 6-[(1-methyl-1H-pyrazol-5-yl)amino]-4-oxo-spiro[chroman-2,4'-piperidine]-1'-carboxylate tert-Butyl 6-bromo-4-oxospiro[chroman-2,4'-piperidine]-1'-carboxylate (16.3 g), 5-amino-1-methyl-1H-pyrazole (4.00 g), palladium acetate (922 mg), 2-(di-t-butylphosphino) biphenyl (1.23 g) and cesium carbonate (16.1 g) were suspended in 1,4-dioxane (20 mL), and heated under reflux at 110° C. for 5 hours. The reaction liquid was filtered through Celite, the residue on the Celite was washed with chloroform, and the filtrate was concentrated under reduced pressure. The resulting residue was purified through silica gel column chromatography (hexane/EtOAc) to obtain the intended compound as a yellow amorphous substance.

Reference Example 49

6-[(1-Methyl-1H-pyrazol-5-yl)amino]spiro[chroman-2,4'-piperidin]-4-one hydrochloride The intended compound was produced according to the procedure described in Reference Example 18 but using tert-Butyl 6-[(1-methyl-1H-pyrazol-5-yl)amino]-4-oxo-spiro[chroman-2,4'-piperidine]-1'-carboxylate in place of tert-butyl 4-oxo-6-(1H-tetrazol-5-yl)spiro[chroman-2,4'-piperidine]-1'-carboxylate.

Reference Example 50

1'-tert-Butoxycarbonyl-[4-oxospiro[chroman-2,4'-piperidine]-6-yl]-carboxylic acid carbamoylmethyl amide tert-butyl 6-carboxy-4-oxospiro[chroman-2,4'-piperidine]-1'-carboxylate (7.50 g, 20.8 mmol), glycinamide hydrochloride (2.76 g, 24.9 mmol), EDCI (4.78 g, 24.9 mmol), HOBT (3.78 g, 24.9 mmol), and TEA (5.80 ml, 41.6 mmol) were suspended in DMF (75 ml) and stirred at room temperature for 23 h. After removal of the solvent, the residue was diluted with EtOAc and H$_2$O. The aqueous layer was extracted with EtOAc and the combined organic layer was washed with saturated NaHCO3 aq. and brine, dried over MgSO4. The desiccant was removed through filtration and the filtrate was concentrated under reduced pressure. The residue was triturated with MeOH-Et2O and the insoluble solid was collected through filtration to obtain the intended compound as a colorless solid.

Reference Example 51

4-Oxospiro[chroman-2,4'-piperidine]-6-carboxylic acid carbamoylmethyl amide hydrochloride The intended compound was produced according to the Reference Example 18 but using 1'-tert-butoxycarbonyl-[4- oxospiro[chroman-2,4'-piperidine]-6-yl]-carboxylic acid N-carbamoylmethylamide in place of tert-butyl 4-oxo-6-(1H-tetrazol-5-yl)spiro[chroman-2,4'-piperidine]-1'-carboxylate.

The usefulness of the compounds of the invention as medicines is demonstrated, for example, by the following pharmacological test example.

Biological Assays

A. Pharmacological Test Example (Acetyl CoA Carboxylase (ACC) Activity Inhibition Test)

A test compound is dissolved in dimethyl sulfoxide (DMSO) to a concentration of 10 mM and then diluted with DMSO to give a 100-fold concentrated solution of the compound compared with target assay concentration. The ACC enzyme activity inhibition test is carried out according to a modification of Thampy & Wakil's method (*J. Biol. Chem.*, Vol. 260, pp. 6318-6323 (1985)). Concretely, 0.8 µl of the diluted test compound is added to each well of 96-well assay plate (Perkin Elmer Opti Plate), then 40 µl of a substrate solution (50 mM Hepes sodium (pH 7.5), 2 mM DTT, 10 mM ATP, 500 µM acetyl CoA, 0.17 mM NaH[$^{14}$C]O$_3$ (58 mCi/mmol, by Amersham), 8 mM NaHCO$_3$) is added to each well, and 40 µL of an enzyme solution (1 to 2 nM human ACC1 or human ACC2, 50 mM Hepes sodium (pH 7.5), 2 mM DTT, 40 mM MgCl$_2$, 40 mM tripotassium citrate 1 mg/ml fetal bovine serum albumin) is added thereto. Then, the upper side of the plate is sealed up, and the plate is incubated with gently stirring at 37° C. for 40 minutes. Next, 20 µl of 1 N HCl is added to each well to stop the enzyme reaction, and the assay plate is stirred overnight to remove the unreacted NaH[$^{14}$C]O$_3$. Next, 100 µl of a scintillator (Perkin Elmer's Microscinti 40) is added to each well and the plate is stirred, then the radioactivity of the fixed [$^{14}$C] is counted using a microplate scintillation counter (Perkin Elmer's Topcount), the radioactivity of which represents the enzyme activity in each well. The human ACC1 and human ACC2 enzyme-inhibition activities of the test compounds are calculated, based on the radioactivity of the well added by DMSO without test compound as a control.

The compounds of the invention were tested according to this method and the compounds tested all inhibited both ACC1 and ACC2. The results are shown in the following

TABLE

| Inhibition (%) by 1 µmol/liter Chemical | | |
|---|---|---|
| Compound | human ACC1 | human ACC2 |
| Example 1 | 91% | 89% |
| Example 2 | 93% | 93% |
| Example 3 | 100% | 97% |
| Example 4 | 96% | 97% |
| Example 5 | 99% | 99% |
| Example 7 | 100% | 99% |
| Example 8 | 99% | 99% |
| Example 10 | 93% | 96% |
| Example 11 | 99% | 98% |
| Example 13 | 100% | 99% |
| Example 17 | 98% | 99% |
| Example 23 | 99% | 98% |
| Example 24 | 99% | 100% |
| Example 31 | 97% | 98% |
| Example 36 | 99% | 99% |
| Example 45 | 100% | 100% |
| Example 56 | 99% | 99% |
| Example 57 | 99% | 99% |

Representative compounds of the present invention, including the compounds of Example 1-60, were tested in the above assay and found to have a percent inhibition of greater than or equal to 50% for ACC-1 and a percent inhibition of greater than or equal to 50% for ACC-2 in the acetyl CoA carboxylase (ACC) activity inhibition test.

B. Effect of ACC1/2 Inhibitor on In Vivo Body Weight, Fat Mass, Fatty Liver and Plasma Glucose Levels Effect of ACC1/2 inhibitor on body weight, fat mass, fatty liver and plasma glucose level can be determined in either high fat diet induced obese or KKAy diabetic mice.

Male C57black/6J mice at approximately 6 weeks old are individually housed and maintained on chow diet for 2 weeks prior to the study. Then the mice are fed with a 60% fat diet for 5 weeks before dosing. The mice (n=8) on the high fat diet are orally dosed with either vehicle control (0.5% methylcellulose solution) or an ACC1/2 inhibitor (various doses) for 6 weeks. Body weight is determined on a daily basis and fat mass is measured by NMR every other week. Hepatic triglyceride content is determined at week 6. Effective ACC1/2 inhibitors result reduced body weight gain, reduced fat mass gain, and reduced hepatic triglyceride content in ACC1/2 inhibitor treated male C57black/6J mice in contrast to the vehicle control group.

Male KKAy mice at approximately 8 weeks old are individually housed and maintained on for 2 weeks prior to the study. The mice (n=10) are orally dosed with either vehicle control (0.5% methylcellulose solution) or an ACC1/2 inhibitor (various doses) for 2 weeks. At week 2, blood is collected at 23 hours post dose and plasma glucose concentration is determined. Effective ACC1/2 inhibitors result in reduced plasma glucose levels in ACC1/2 inhibitor treated KKAy mice in contrast to the vehicle control group.

C. Human Study for Effect on Food Intake and Glucose/Insulin Levels 800 people with a BMI≧30 who have impaired fasting plasma glucose levels, impaired glucose tolerance, or elevated serum insulin, indicative of a prediabetic insulin resistant state, and who may have elevated serum glucose levels, indicative of type II diabetes, are advised to diet and increase their physical activity. After a two-week placebo run-in period, which includes a standardized program of diet, physical activity, and lifestyle changes, the patients are randomized into 2 treatment groups: placebo; and an effective dose of a compound of formula (I). The compound of formula (I) is given once or more per day, as previously determined to be effective. Patients are treated for 6 months, body weights are measured biweekly, and appetite, hunger, satiety are measured weekly using standard questionnaires. Serum glucose, insulin levels and body weight are determined at day 0, monthly, and after the final dose.

Effective compounds result in body weight loss or an improvement in serum insulin levels, indicative of improved insulin sensitivity or lower fasting blood glucose levels.

Formulation Preparation Example 1

20.0 g of the compound of Example 1, 417 g of lactose, 80 g of crystalline cellulose and 80 g of partially-aliphatized starch are mixed in a V-shape mixer, and 3.0 g of magnesium stearate is added to it and mixed. The mixture powder is tableted according to an ordinary method to obtain 3000 tablets each having a diameter of 7.0 mm and a weight of 150 mg.

| Ingredients of Tablet (150 mg) | |
| --- | --- |
| Compound of Example 1 | 5.0 mg |
| Lactose | 104.25 mg |
| Crystalline cellulose | 20.0 mg |
| Partially-alphatized starch | 20.0 mg |
| Magnesium stearate | 0.75 mg |

Formulation Preparation Example 2

10.8 g of hydroxypropyl cellulose 2910 and 2.1 g of polyethylene glycol 6000 are dissolved in 172.5 g of pure water, and 2.1 g of titanium oxide is dispersed therein to prepare a coating liquid. Using a high-coater-mini, 2500 tablets of Preparation Example 1 that is prepared separately is sprayed with the coating liquid to obtain film-coated tables each having a weight of 155 mg.

| Ingredients of Tablet (155 mg) | |
| --- | --- |
| Tablet of Preparation Example 1 | 150 mg |
| Hydroxypropyl cellulose 2910 | 3.6 mg |
| Polyethylene glycol 6000 | 0.7 mg |
| Titanium dioxide | 0.7 mg |

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated obesity, diabetes, obesity-related disorders, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and embodiments of the present invention. It is intended, therefore, that the invention be limited only by the scope of the claims which follow and that such claims be interpreted as broadly as is reasonable.

What is claimed is:

1. A compound represented by a general formula (I-2):

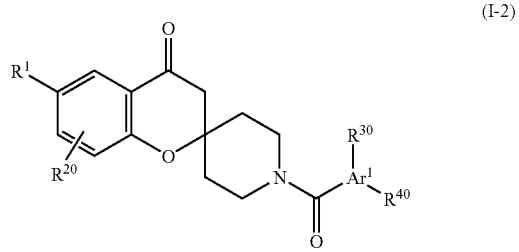

(I-2)

wherein,
Ar$^1$ represents a group formed from an aromatic ring selected from a group consisting of indole, 1H-indazole, 2H-indazole, 1H-thieno[2,3-c]pyrazole, 1H-pyrazolo[3,4-b]pyridine, benzo[b]furan, benzimidazole, benzoxazole, 1,2-benzisoxazole and imidazo[1,2-a]pyridine, having R$^{30}$ and R$^{40}$, and optionally having a substituent selected from a group consisting of a halogen atom, a nitro group, a cyano group, a hydroxyl group, a C1-C6 alkyl group, a halo-C1-C6 alkyl group, a hydroxy-C1-C6 alkyl group, a cyclo-C3-C6 alkyl group, a C2-C6 alkenyl group, a C1-C6 alkoxy group, a halo-C1-C6 alkoxy group, a C1-C6 alkylthio group, a carboxyl group and a carbamoyl group;

R$^1$ represents an aryl or heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N(R$^c$)R$^d$; or a C1-C6 alkyl group or a C2-C6 alkenyl group having the aryl or heterocyclic group;

R$^{20}$ represents a hydrogen atom, a halogen atom, a C1-C6 alkyl group, or a C1-C6 alkoxy group;

R$^{30}$ and R$^{40}$ each independently represent a halogen atom, a nitro group, a cyclo-C3-C6 alkyl group, a carbamoyl group optionally substituted with a C1-C6 alkyl or cyclo-C3-C6 alkyl group, or a group of —N(R$^e$)R$^f$; or a C2-C7 alkanoyl group, a C1-C6 alkoxy group, a C2-C7 alkoxycarbonyl group, a cyclo-C3-C6 alkyloxycarbonyl group, a C1-C6 alkylsulfonyl group, a C1-C6 alkylthio group, a cyclo-C3-C6 alkyloxy group, a cyclo-C3-C6 alkyl-C1-C6 alkoxy group, a cyclo-C3-C6 alkylsulfonyl group, a cyclo-C3-C6 alkylthio group or a cyclo-C3-C6 alkyl-C1-C6 alkylthio group, optionally substituted with a halogen atom or a hydroxyl group, wherein the cyclo-C3-C6 alkyl group in the cyclo-C3-C6 alkyloxycarbonyl group, the cyclo-C3-C6 alkyloxy group, the cyclo-C3-C6 alkyl-C1-C6 alkoxy group, the cyclo-C3-C6 alkylsulfonyl group, the cyclo-C3-C6 alkylthio group or the cyclo-C3-C6 alkyl-C1-C6 alkylthio group may be interrupted by an oxygen atom, a sulfur atom or an imino group; or
a C1-C6 alkyl group optionally having a substituent selected from a group consisting of a halogen atom, a hydroxyl group and a cyclo-C3-C6 alkyl group;

R$^c$ and R$^d$ each independently represent a hydrogen atom, a C1-C6 alkyl group, or a halo-C1-C6 alkyl group; and R$^e$ and R$^f$ each independently represent a hydrogen atom, a C1-C6 alkyl group, or a halo-C1-C6 alkyl group, or taken together, they may form a C2-C5 alkylene group optionally interrupted by an oxygen atom, a sulfur atom or an imino group;

or a pharmaceutically acceptable salt.

2. The compound as claimed in claim 1, wherein R$^{30}$ and R$^{40}$ each independently represent a nitro group, a cyclo-C3-C6 alkyl group, a carbamoyl group optionally substituted with a C1-C6 alkyl or cyclo-C3-C6 alkyl group, a C1-C6 alkoxy group optionally substituted with a hydroxyl group, or a C1-C6 alkyl group optionally substituted with a hydroxyl group; or a pharmaceutically acceptable salt or ester thereof.

3. The compound as claimed in claim 1, wherein R$^{30}$ is a C1-C6 alkoxy group optionally substituted with a hydroxyl group; and R$^{40}$ is a cyclo-C3-C6 alkyl group, a C1-C6 alkoxy group or a C1-C6 alkyl group; or a pharmaceutically acceptable salt.

4. The compound as claimed in claim 1, wherein $R^1$ is an aryl or a heterocyclic group optionally having a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$; or a pharmaceutically acceptable salt.

5. The compound as claimed in claim 4, wherein the aryl or heterocyclic group for $R^1$, which may have a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$, is a phenyl group optionally substituted with a carboxyl group, a C2-C7 alkoxycarbonyl group or a group of —CO—N($R^c$)$R^d$; a pyrazolyl group optionally substituted with a C1-C6 alkyl group; a 1,2,4-triazolyl group; a tetrazolyl group optionally substituted with a C2-C7 alkanoyloxy-C1-C6 alkyl group; a pyridyl group optionally substituted with a halogen atom, a C1-C6 alkyl group, a C1-C6 alkoxy group, a carboxyl group, a C2-C7 alkoxycarbonyl group or a group of —CO—N($R^c$)$R^d$; a pyrimidinyl group; a dihydro-1,2,4-triazolyl group optionally substituted with an oxo group; a dihydro-1,2,4-oxadiazolyl group optionally substituted with an oxo group; or a dihydropyridyl group optionally substituted with an oxo group; or a pharmaceutically acceptable salt.

6. The compound as claimed in claim 4, wherein the aryl or heterocyclic group for $R^1$, which may have a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$, is a phenyl group optionally substituted with a carboxyl group or a group of —CO—N($R^c$)$R^d$; a pyrazolyl group optionally substituted with a C1-C6 alkyl group; a 1,2,4-triazolyl group; a tetrazolyl group optionally substituted with a C2-C7 alkanoyloxy-C1-C6 alkyl group; a pyridyl group optionally substituted with a C1-C6 alkoxy group, a carboxyl group or a group of —CO—N($R^c$)$R^d$; a dihydro-1,2,4-triazolyl group optionally substituted with an oxo group; or a dihydro-1,2,4-oxadiazolyl group optionally substituted with an oxo group; or a pharmaceutically acceptable salt.

7. The compound as claimed in claim 4, wherein the aryl or heterocyclic group for $R^1$, which may have a substituent selected from a group consisting of a halogen atom, a hydroxyl group, an oxo group, a thioxo group, a C1-C6 alkyl group, a halo-C1-C6 alkyl group, a hydroxy-C1-C6 alkyl group, a C2-C7 alkanoyloxy-C1-C6 alkyl group, a C1-C6 alkoxy group, a halo-C1-C6 alkoxy group, a formyl group, a carboxyl group, a C2-C7 alkanoyl group, a C2-C7 alkoxycarbonyl group, a C1-C6 alkylsulfonyl group and a group of —CO—N($R^c$)$R^d$, is a phenyl group optionally substituted with a carboxyl group or a group of —CO—N($R^c$)$R^d$; a tetrazolyl group optionally substituted with a C2-C7 alkanoyloxy-C1-C6 alkyl group; a pyridyl group optionally substituted with a C1-C6 alkoxy group, a carboxyl group or a group of —CO—N($R^c$)$R^d$; or a dihydro-1,2,4-oxadiazolyl group optionally substituted with an oxo group; or a pharmaceutically acceptable salt.

8. The compound as claimed in claim 1, wherein $R^1$ is a pyridyl group substituted with a carboxyl group; or a pharmaceutically acceptable salt.

9. The compound as claimed in claim 1, which is selected from the following:

(1) 1-[(1-Ethyl-4-methoxy-1H-benzimidazol-6-yl)carbonyl]-6-(1H-tetrazol-5-yl)spiro[chroman-2,4'-piperidine]-4-one, (2) 1'-[(3-Cyclopropyl-8-methoxyimidazo[1,2-a]pyridin-6-yl)carbonyl]-6-(1H-tetrazol-5-yl)spiro[chroman-2,4'-piperidin]-4-one, (3) 1'-[(1-Cyclopropyl-4-methoxy-1H-indol-6-yl)carbonyl]-6-(5-oxo-4,5-dihydro-1,2,4-oxadiazol-3-yl)spiro[chroman-2,4'-piperidin]-4-one, (4) 1'-{[1-Ethyl-4-(2-hydroxyethoxy)-1H-indol-6-yl]carbonyl}-6-(1H-tetrazol-5-yl)spiro[chroman-2,4'-piperidin]-4-one, (5) Sodium 3-{1'-[(1-cyclopropyl-4-methoxy-1H-indol-6-yl)carbonyl]-4-oxospiro[chroman-2,4'-piperidin]-6-yl}benzoate, (6) 5-{1'-[(1-Cyclopropyl-4-methoxy-1H-indol-6-yl)carbonyl]-4-oxospiro[chroman-2,4'-piperidin]-6-yl}nicotinic acid, (7) 5-{1'-[(1-Cyclopropyl-4-methoxy-1H-indol-6-yl)carbonyl]-4-oxo-3,4-dihydrospiro[chroman-2,4'-piperidin]-6-yl}nicotinic acid sodium salt, (8) 1'-{[1,4-Dimethoxy-1H-indol-6-yl]carbonyl}-6-(1H-tetrazol-5-yl)spiro[chroman-2,4'-piperidin]-4-one, (9) 1'-{[1,4-Dimethoxy-1H-indol-6-yl]carbonyl}-6-(1H-tetrazol-5-yl)spiro[chroman-2,4'-piperidin]-4-one sodium salt,

(10) 1'-[(1-Ethyl-4-methoxy-1H-indazol-6-yl)carbonyl]-6-(1H-tetrazol-5-yl)spiro[chroman-2,4'-piperidin]-4-one,

(11) 1'-[(1-Cyclopropyl-4-methoxy-1H-indol-6-yl)carbonyl]-6-(1H-tetrazol-5-yl)spiro[chroman-2,4'-piperidin]-4-one,

(12) 1'-[(1-Cyclopropyl-4-methoxy-1H-indol-6-yl)carbonyl]-6-(1H-tetrazol-5-yl)spiro[chroman-2,4'-piperidin]-4-one sodium salt,

(13) 1'-[(1-Cyclopropyl-4-ethoxy-1H-indol-6-yl)carbonyl]-6-(1H-tetrazol-5-yl)spiro[chroman-2,4'-piperidin]-4-one,

(14) 1'-[(1-Cyclopropyl-4-ethoxy-1H-indol-6-yl)carbonyl]-6-(1H-tetrazol-5-yl)spiro[chroman-2,4'-piperidin]-4-one sodium salt,

(15) 1'-[(1,4-Diethoxy-1H-indazol-6-yl)carbonyl]-6-(1H-tetrazol-5-yl)spiro[chroman-2,4'-piperidin]-4-one,

(16) 1'-[(3-Chloro-1-cyclopropyl-4-ethoxy-1H-indol-6-yl)carbonyl]-6-(1H-tetrazol-5-yl)spiro[chroman-2,4'-piperidin]-4-one,

(17) 1'-[(1-Cyclopropyl-4-ethoxy-3-methyl-1H-indol-6-yl)carbonyl]-6-(1H-tetrazol-5-yl)spiro[chroman-2,4'-piperidin]-4-one,

(18) 3-(1'-{[1-Cyclopropyl-4-(2-hydroxyethoxy)-1H-indol-6-yl]carbonyl}-4-oxo-spiro[chroman-2,4'-piperidin]-6-yl)benzoic acid,

(19) 5-{1'-[(1-Cyclopropyl-4-ethoxy-1H-indol-6-yl)carbonyl]-4-oxo-spiro[chroman-2,4'-piperidin]-6-yl}nicotinic acid sodium salt,

(20) 2-{1'-[(1-Cyclopropyl-4-methoxy-1H-indol-6-yl)carbonyl]-4-oxo-spiro[chroman-2,4'-piperidin]-6-yl}isonicotinic acid sodium salt,

(21) 4-{1'-[(1-Cyclopropyl-4-methoxy-1H-indol-6-yl)carbonyl]-4-oxo-spiro[chroman-2,4'-piperidin]-6-yl}pyridine-2-carboxylic acid sodium salt,
(22) 5-{1'-[(1-Cyclopropyl-4-methoxy-1H-indol-6-yl)carbonyl]-4-oxo-spiro[chroman-2,4'-piperidin]-6-yl}pyridine-2-carboxylic acid sodium salt,
(23) 5-{1'-[(1-Cyclopropyl-4-methoxy-3-methyl-1H-indol-6-yl)carbonyl]-4-oxo-spiro[chroman-2,4'-piperidin]-6-yl}nicotinic acid sodium salt,
(24) 5-{1'-[(3-Chloro-1-cyclopropyl-4-methoxy-1H-indol-6-yl)carbonyl]-4-oxo-spiro[chroman-2,4'-piperidin]-6-yl}nicotinic acid sodium salt,
(25) 1'-[(4-Acetyl-7-methoxy-1-benzofuran-2-yl)carbonyl]-6-(1H-tetrazol-5-yl)spiro[chroman-2,4'-piperidin]-4-one,
(26) 1'-[(1-Ethyl-3-methyl-1H-thieno[2,3-c]pyrazol-5-yl)carbonyl]-6-(1H-tetrazol-5-yl)spiro[chroman-2,4'-piperidin]-4-one,
(27) 5-{1'-[(1-Cyclopropyl-4-methoxy-3-methyl-1H-indol-6-yl)carbonyl]-4-oxo-spiro[chroman-2,4'-piperidin]-6-yl}nicotinic acid,
(28) 1'-[(4-Methoxy-1-methyl-1H-pyrazolo[3,4-b]pyridin-6-yl)carbonyl]-6-(1H-tetrazol-5-yl)spiro[chroman-2,4'-piperidin]-4-one,
(30) 1'-[(3-Chloro-1-cyclopropyl-7-ethoxy-1H-indol-5-yl)carbonyl]-6-(1H-tetrazol-5-yl)spiro[chroman-2,4'-piperidin]-4-one,
(31) 1'-[(3-Cyclopropyl-7-ethoxy-1,2-benzisoxazol-5-yl)carbonyl]-6-(1H-tetrazol-5-yl)spiro[chroman-2,4'-piperidin]-4-one,
(32) 1'-[(2-Cyclopropyl-7-ethoxy-1,3-benzoxazol-5-yl)carbonyl]-6-(1H-tetrazol-5-yl)spiro[chroman-2,4'-piperidin]-4-one,
(33) 1-Cyclopropyl-4-ethoxy-6-{[4-oxo-6-(1H-tetrazol-5-yl)spiro[chroman-2,4'-piperidin]-1'-yl]carbonyl}-1H-indole-3-carboxamide,
(36) 1'-{[1-Cyclopropyl-4-(2-hydroxyethoxy)-1H-indol-6-yl]carbonyl}-6-(1H-tetrazol-5-yl)spiro[chroman-2,4'-piperidin]-4-one,
(37) 1-Cyclopropyl-4-ethoxy-N-methyl-6-{[4-oxo-6-(1H-tetrazol-5-yl)spiro[chroman-2,4'-piperidin]-1'-yl]carbonyl}-1H-indole-3-carboxamide,
(38) Methyl 3-(1'-{[3-carbamoyl-1-cyclopropyl-4-ethoxy-1H-indol-6-yl]carbonyl}-4-oxospiro[chroman-2,4'-piperidin]-6-yl)benzoate,
(39) 3-(1'-{[3-Carbamoyl-1-cyclopropyl-4-ethoxy-1H-indol-6-yl]carbonyl}-4-oxospiro[chroman-2,4'-piperidin]-6-yl)benzoic acid,
(40) 1-Cyclopropyl-4-ethoxy-6-{[4-oxo-6-(1H-pyrazol-4-yl)spiro[chroman-2,4'-piperidin]-1'-yl]carbonyl}-1H-indole-3-carboxylic acid,
(41) 1-Cyclopropyl-4-ethoxy-6-({6-[(1-methyl-1H-pyrazol-5-yl)amino]-4-oxospiro[chroman-2,4'-piperidin]-1'-yl}carbonyl)-1H-indole-3-carboxylic acid,
(42) 4-{1'-[(1-Cyclopropyl-4-methoxy-3-methyl-1H-indol-6-yl)carbonyl]-4-oxospiro[chroman-2,4'-piperidin]-6-yl}pyridine-2-carboxylic acid,
(43) 5-{1'-[(1-Cyclopropyl-4-methoxy-3-methyl-1H-indol-6-yl)carbonyl]-4-oxospiro[chroman-2,4'-piperidin]-6-yl}-2-methylnicotinic acid,
(44) 6-{1'-[(1-Cyclopropyl-4-methoxy-3-methyl-1H-indol-6-yl)carbonyl]-4-oxospiro[chroman-2,4'-piperidin]-6-yl}nicotinic acid,
(45) 5-{1'-[(1-Cyclopropyl-4-ethoxy-3-methyl-1H-indol-6-yl)carbonyl]-4-oxospiro[chroman-2,4'-piperidin]-6-yl}nicotinic acid,
(46) 4-{1'-[(1-Cyclopropyl-4-ethoxy-3-methyl-1H-indol-6-yl)carbonyl]-4-oxospiro[chroman-2,4'-piperidin]-6-yl}pyridine-2-carboxylic acid,
(47) 5-{1'-[(1-Cyclopropyl-4-ethoxy-3-methyl-1H-indol-6-yl)carbonyl]-4-oxo-spiro[chroman-2,4'-piperidin]-6-yl}nicotinic acid sodium salt,
(48) 5-{1'-[(1,4-Dimethoxy-3-methyl-1H-indol-6-yl)carbonyl]-4-oxospiro[chroman-2,4'-piperidin]-6-yl}nicotinic acid,
(49) 6-(5-Bromopyridin-3-yl)-1'-[(1-cyclopropyl-4-methoxy-3-methyl-1H-indol-6-yl)carbonyl]spiro[chroman-2,4'-piperidin]-4-one,
(50) Methyl 5-{1'-[(1-cyclopropyl-4-methoxy-3-methyl-1H-indol-6-yl)carbonyl]-4-oxospiro[chroman-2,4'-piperidin]-6-yl}nicotinate,
(51) 1'-[(1-Cyclopropyl-4-methoxy-1H-indol-6-yl)carbonyl]-6-(5-oxo-4,5-dihydro-1H-1,2,4-triazol-3-yl)spiro[chroman-2,4'-piperidin]-4-one,
(53) Sodium 5-{1'-[(1-cyclopropyl-4-ethoxy-3-methyl-1H-indol-6-yl)carbonyl]-4-oxospiro[chroman-2,4'-piperidin]-6-yl}-2-methylnicotinate,
(54) 1'-[(1-Ethyl-4-morpholin-4-yl-1H-indol-6-yl)carbonyl]-6-(1H-tetrazol-5-yl)spiro[chroman-2,4'-piperidin]-4-one,
(55) 1'-[(1-Cyclopropyl-4-methoxy-3-methyl-1H-indol-6-yl)carbonyl]-6-(1H-tetrazol-5-yl)spiro[chroman-2,4'-piperidin]-4-one,
(56) 1'-[(1-Ethyl-4-methoxy-1H-indol-6-yl)carbonyl]-6-(1H-tetrazol-5-yl)spiro[chroman-2,4'-piperidin]-4-one,
(57) 5-{1'-[(1-Cyclopropyl-4-methoxy-1H-indol-6-yl)carbonyl]-4-oxo-spiro[chroman-2,4'-piperidin]-6-yl}-4H-1,2,4-triazole-3-carboxamide,
(58) 1'-[(1,3-Diethyl-7-methoxy-2-oxo-2,3-dihydro-1H-benzimidazol-5-yl)carbonyl]-6-(1H-tetrazol-5-yl)spiro[chroman-2,4'-piperidin]-4-one,
(59) 5-{1'-[(6-Cyclopropyl-1-isopropyl-1H-pyrazolo[3,4-b]pyridin-4-yl)carbonyl]-4-oxo-spiro[chroman-2,4'-piperidin]-6-yl}nicotinic acid, or
(60) 1'-[(1-Cyclopropyl-4-methoxy-1H-benzimidazol-6-yl)carbonyl]-6-(1H-tetrazol-5-yl)spiro[chroman-2,4'-piperidin]-4-one;
or a pharmaceutically acceptable salt.

10. The compound of claim 1 which is 3-{1'-[(1-Cyclopropyl-4-methoxy-1H-indol-6-yl)carbonyl]-4-oxospiro[chroman-2,4'-piperidin]-6-yl}benzoic acid, or a pharmaceutically acceptable salt or ester thereof.

11. The compound of claim 1 which is 5-{1'-[(1-Cyclopropyl-4-methoxy-1H-indol-6-yl)carbonyl]-4-oxospiro[chroman-2,4'-piperidin]-6-yl}nicotinic acid, or a pharmaceutically acceptable salt or ester thereof.

12. The compound of claim 1 which is 1'-[(1-Cyclopropyl-4-methoxy-1H-indol-6-yl)carbonyl]-6-(1H-tetrazol-5-yl)spiro[chroman-2,4'-piperidin]-4-one, or a pharmaceutically acceptable salt thereof.

13. The compound of claim 1 which is 1'-[(1-Cyclopropyl-4-ethoxy-3-methyl-1H-indol-6-yl)carbonyl]-6-(1H-tetrazol-5-yl)spiro[chroman-2,4'-piperidin]-4-one, or a pharmaceutically acceptable salt thereof.

14. The compound of claim 1 which is 5-{1'-[(1-Cyclopropyl-4-methoxy-3-methyl-1H-indol-6-yl)carbonyl]-4-oxo-spiro[chroman-2,4'-piperidin]-6-yl}nicotinic acid, or a pharmaceutically acceptable salt.

15. A pharmaceutical composition comprising a therapeutically effective amount of the compound of formula (I) of claim 1 or a pharmaceutically acceptable salt, and a pharmaceutically acceptable additive.

* * * * *